United States Patent [19]
Sakamoto et al.

[11] Patent Number: 5,594,006
[45] Date of Patent: Jan. 14, 1997

[54] CARBOSTYRIL DERIVATIVES AS MATRIX METALLOPROTEINASES INHIBITORS

[75] Inventors: Makoto Sakamoto; Takeshi Imaoka; Masaaki Motoyama; Yoshihito Yamamoto; Hideki Takasu, all of Otsu, Japan

[73] Assignee: Otsuka Pharmaceutical Co., Ltd., Tokyo, Japan

[21] Appl. No.: 389,645

[22] Filed: Feb. 16, 1995

Related U.S. Application Data

[63] Continuation-in-part of Ser. No. 338,600, filed as PCT/JP94/00434, Mar. 17, 1994, abandoned.

[30] Foreign Application Priority Data

Mar. 18, 1993 [JP] Japan ................. 5-58264
Oct. 14, 1993 [JP] Japan ................. 5-256873
Sep. 12, 1994 [JP] Japan ................. 6-216890

[51] Int. Cl.$^6$ .............. C07D 215/227; C07D 215/38; A61K 31/47
[52] U.S. Cl. ............... 514/312; 546/155; 546/158
[58] Field of Search .................... 546/155, 158; 514/312

[56] References Cited

U.S. PATENT DOCUMENTS 4,599,361  7/1986  Dickens et al. ............ 514/575
4,692,522  9/1987  Parsons et al. ............ 540/523
4,996,358  2/1991  Handa ..................... 562/621

FOREIGN PATENT DOCUMENTS

WO9005719   5/1990   WIPO.
WO9005716   5/1990   WIPO.
WO9217460  10/1992   WIPO.
94/10990    5/1994   WIPO.

OTHER PUBLICATIONS

Chemical Abstracts, 122:230797, 1994.

Primary Examiner—C. Warren Ivy
Assistant Examiner—D. Margaret M. Mach
Attorney, Agent, or Firm—Sughrue, Mion, Zinn, Macpeak & Seas

[57] ABSTRACT

This invention provides a carbostyril derivative of the formula (1):

$$R^5-ONH-CO-CH(R^1)-CH(R^6)-CON-\text{(carbostyril with }R^2, R^3, (R^4)_n\text{)}$$

where $R^1$, $R^2$, $R^3$, $R^4$, $R^5$, $R^6$ and n are as defined, or its salt. This carbostyril derivative or its salt possess an excellent matrix metalloproteinases inhibitory action.

27 Claims, No Drawings

5,594,006

CARBOSTYRIL DERIVATIVES AS MATRIX METALLOPROTEINASES INHIBITORS

CROSS REFERENCE TO RELATED APPLICATION

This application is a Continuation-in-part of Ser. No. 08/338,600 filed Nov. 18, 1994, now abandoned which is a 371 of PCT/JP94/00434, filed Mar. 17, 1994.

TECHNICAL FIELD

The present invention relates to carbostyril derivatives, method of preparing the same, and extracellular matrix metalloproteinases inhibitor.

BACKGROUND ART

The extracellular matrix metalloproteinases are secreted from mammal animal cells, and decomposes extracellular matrix (collagen, type IV collagen, laminin proteoglican, fibronectin, elastin, gelatin, etc.). Abnormal promotion of secretion and activity of extracellular matrix metalloproteinases are considered to induce various diseases, including metastasis, infiltration and proliferation of cancer cells, rheumatoid arthritis, peridontal diseases, corneal ulcer, osteoporosis, other bone absorption diseases, multiple sclerosis, and the like. Substances showing inhibitory actions of extracellular matrix metalloproteinases include natural products such as TIMP-1, TIMP-2, and $\alpha_2$-macroglobulin. Compounds possessing such inhibitory action are disclosed in the Japanese Patent Laid-open Publication No. 62-230757, WO-905716 and WO-9217460. More specifically, the Japanese Patent Laid-open Publication No. 62-230757 discloses a compound expressed in a formula:

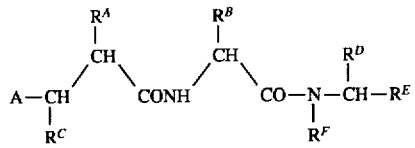

[where A denotes a group HN(OH)—CO— or HCO—NOH—; $R^A$ is an alkyl group with $C_2$ to $C_5$; $R^B$ is a characteristic group of a natural α-amino acid of which any existing functional group may be protected, any existing amino group may be acylated, or any existing carboxylic group may be formed into amide (however, excluding hydrogen atom or methyl group); $R^C$ is hydrogen atom, amino, hydroxy, mercapto, $C_1$ to $C_6$ alkyl, $C_1$ to $C_6$ alkoxy, $C_1$ to $C_6$ alkylamino, $C_1$ to $C_6$ alkylthio or aryl- ($C_1$ to $C_6$ alkyl) group, or amino- ($C_1$ to $C_6$ alkyl), hydroxy- ($C_1$ to $C_6$ alkyl), mercapto- ($C_1$ to $C_6$ alkyl) or carboxyl- ($C_1$ to $C_6$ alkyl) of which amino, hydroxy, mercapto or carboxyl group may be protected, amino group may be acylated, or carboxyl group may be formed into amide; $R^D$ is hydrogen atom or methyl group, $R^E$ is hydrogen atom, or $C_1$ to $C_6$ alkyl, $C_1$ to $C_6$ alkoxy-$C_1$ to $C_6$ alkyl, di($C_1$ to $C_6$ alkoxy)-methylene, carboxyl, ($C_1$ to $C_6$ alkyl)-carbonyl, ($C_1$ to $C_6$ alkoxy)-carbonyl, arylmethoxycarbonyl, ($C_1$ to $C_6$ alkyl)aminocarbonyl or arylaminocarbonyl; $R^F$ is hydrogen atom or methyl group, $R^B$ and $R^D$ may be combined together to form —(CH$_2$)m— group wherein p is 4 to 11; and $R^D$ and $R^F$ may be combined together to form trimethylene group].

WO-905716 discloses a compound expressed in a formula:

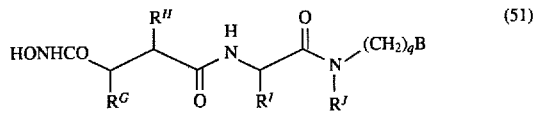

[where $R^G$ is hydrogen atom, $C_1$ to $C_6$ alkyl, $C_1$ to $C_6$ alkenyl, phenyl, phenyl ($C_1$ to $C_6$) alkyl, $C_1$ to $C_6$ alkylthiomethyl, phenylthiomethyl, substituted phenylthiomethyl, phenyl($C_1$ to $C_6$)alkylthiomethyl, or hexacyclic thiomethyl group; or $R^G$ denotes —SR$^X$, where $R^X$ denotes as follows:

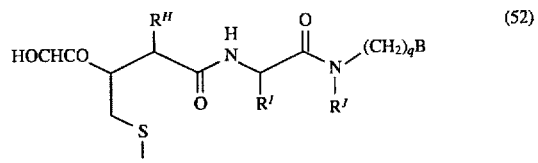

[where $R^H$ is hydrogen atom, $C_1$ to $C_6$ alkyl, $C_1$ to $C_6$ alkenyl, phenyl ($C_1$ to $C_6$) alkyl, cycloalkyl ($C_1$ to $C_6$) alkyl, or cycloalkenyl ($C_1$ to $C_6$) alkyl group; $R^I$ is amino acid side chain, $C_1$ to $C_6$ alkyl, benzyl, ($C_1$ to $C_6$) alkoxybenzyl, benzyloxy ($C_1$ to $C_6$) alkyl or benzyloxybenzyl group; $R^J$ is hydrogen atom or methyl group; q is an integer of 1 to 6; and B is —NH$_2$ group, substituted noncyclic amine or heterocyclic base].

WO-9217460 discloses a compound expressed in a formula:

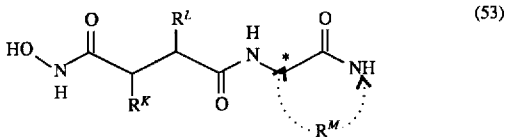

[where $R^K$ is hydrogen atom, $C_1$ to $C_6$ alkyl or —(CH$_2$)$_r$—D—R$^N$ group; r is 0 or an integer of 1 to 6; D is single bond, or oxygen or sulfur atom; $R^N$ is aryl which may be substituted or heteroaryl which may be substituted; $R^L$ is an alkyl group with $C_3$ to $C_6$; $R^M$ is —(CH$_2$)$_s$—E—(CH$_2$)$_t$— group; s is an integer of 1 to 9; t is an integer of 2 to 10; E is —NR$^O$— group ($R^O$ is hydrogen atom, $C_1$ to $C_6$ alkyl, $C_2$ to $C_6$ alkanoyl, $C_1$ to $C_6$ alkoxycarbonyl, aryl, aralkyl, or aralkyloxycarbonyl, in which each aryl group may possess a substituent); and —(CH$_2$)$_s$— is bonded to a carbon atom indicated by * in formula (53)].

At the present, however, a compound having a strong inhibitory action while low in toxicity has not been discovered yet.

DISCLOSURE OF THE INVENTION

It is hence a primary object of the invention to present a novel compound excellent in extracellular matrix metalloproteinases inhibitory action and also low in toxicity. According to the invention, there is provided a carbostyril derivative expressed in formula (1):

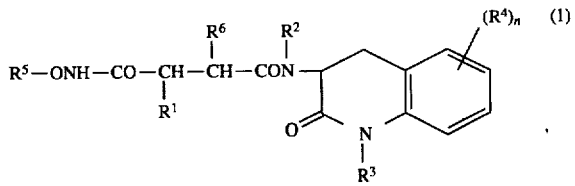

[where $R^1$ denotes hydrogen atom or group —A—$R^{1a}$ (A shows a lower alkylene group, $R^{1a}$ is hydrogen atom, amino group, phthalimido group, thienylthio group, lower alkanoylthio group, mercapto group, phenyl group which may possess one to three groups selected from the group consisting of halogen atom, hydroxyl group, lower alkyl group, lower alkoxy group, carboxy group, lower alkoxycarbonyl group and lower alkylenedioxy group as substituent, carboxy group, lower alkoxy carbonyl group, phenylthio group or lower alkylthio group);

$R^2$ is hydrogen atom or lower alkyl group;

$R^3$ is hydrogen atom, hydroxyl group, lower alkoxy group, lower alkoxy-lower alkoxy group, lower alkoxy-lower alkoxy-lower alkoxy group, lower alkoxy-lower alkoxy-lower alkoxy-lower alkoxy group or group: —B—$R^{3a}$ {B is lower alkylene group, lower alkenylene group or lower alkynylene group, $R^{3a}$ is hydrogen atom, hydroxy group, lower alkoxy group, lower alkoxy-lower alkoxy group, phenyl group which may possess one to three groups selected from the group consisting of halogen atom, cyano group, hydroxy group, lower alkyl group, lower alkoxy group, carboxy group and lower alkoxycarbonyl group as substituent, thienyl group which may possess halogen atom as substituent, phthalimido group, carboxy group, lower alkoxycarbonyl group or group: —CO—N($R^{3b}$)$R^{3c}$ (where $R^{3b}$ is hydrogen atom or lower alkyl group, $R^{3c}$ is hydrogen atom, lower alkyl group or lower alkoxy group, and group —N($R^{3b}$)—$R^{3c}$ may form a saturated heterocyclic ring with five or six members which may further possess one hetero atom selected from the group consisting of nitrogen atom, oxygen atom and sulfur atom)};

$R^4$ is hydrogen atom, halogen atom, hydroxyl group, lower alkyl group, lower alkoxy group, or lower alkylenedioxy group;

$R^5$ is hydrogen atom, benzoyl group, lower alkanoyl group, or phenyl-lower alkyl group;

$R^6$ is alkyl group with 1 to 12 carbon atoms, lower alkoxy-lower alkyl group, or phenyl-lower alkyl group which may possess lower alkylenedioxy group as substituent on the phenyl ring; and n is 1 or 2], and its salt.

The carbostyril derivative and its salt of the invention possess an excellent extracellular matrix metalloproteinases inhibitory action, in particular, the inhibitory action on Stromelysin purified from the culture supernatant of mouse colon cancer cell (Colon 26 Cell), inhibitory action on interstitial collagenase purified from the culture supernatant of human fibroblast cell (Detroit 551 Cell), and inhibitory action on type IV collagenase purified from the culture supernatant of human pulmonary fibrosarcoma cell (HT-1080 Cell), and are low in toxicity and superior in oral absorption.

That is, the compound of the invention is characterized by high inhibitory actions, low toxicity, excellent oral absorption, long duration of effect, high safety, and stability of pharmaceutical preparations.

The carbostyril derivative expressed in formula (1) of the invention and its salts are useful in clinical fields as prophylactic and therapeutic agents for diseases and episodes related with extracellular matrix metalloproteinases (interstitial collagenase, type IV collagenase, Stromelysin, etc.), such as metastasis, infiltration or proliferation of various cancer cells, rheumatoid arthritis, periodontal diseases, corneal ulcer, osteoporosis, other bone absorption diseases, multiple sclerosis, hypomyelination, diseases accompanied by vascularization, dermal and gastrointestinal ulceration, and wound healing and postoperative symptoms, for example, colon anastomosis characterized by elevation of collagenase level, increase of collagen destruction caused in relation with diabetes mellitus, atherosclerosis, proliferation due to suture of blood vessels, nephritis, and others.

DETAILED DESCRIPTION OF THE INVENTION

The groups disclosed in the specification are specifically as follows, whether they exist independently or among other groups.

Examples of lower alkylene group include methylene, methylmethylene, ethylene, dimethylmethylene, trimethylene, 1-methyltrimethylene, 2-methyltrimethylene, 2,2-dimethyltrimethylene, tetramethylene, pentamethylene, hexamethylene groups, and other alkylene groups of straight chain or branched chain with 1 to 6 carbon atoms.

Examples of thienylthio group include 2-thienylthio, 3-thienylthio and other thienylthio groups.

Examples of lower alkanoylthio group include formylthio, acetylthio, propanoylthio, butanoylthio, isobutanoylthio, pentanoylthio, hexanoylthio groups, and other alkanoylthio groups of which alkanoyl portion is an alkanoyl group of straight chain or branched chain with 1 to 6 carbon atoms.

Examples of lower alkyl group include methyl, ethyl, propyl, isopropyl, butyl, tertiary butyl, pentyl, hexyl groups, and other alkyl groups of straight chain or branched chain with 1 to 6 carbon atoms.

Examples of lower alkoxy group include methoxy, ethoxy, propoxy, isopropoxy, butoxy, tertiary butoxy, pentyloxy, hexyloxy groups, and other alkoxy groups of straight chain or branched chain with 1 to 6 carbon atoms.

Examples of lower alkenylene group include vinylene, allylene, isopropenylene, 2-butenylene, 3-pentenylene, 4-hexenylene, 2-methyl-butenylene groups, and other alkenylene groups of straight chain or branched chain with 2 to 6 carbon atoms.

Examples of lower alkynylene group include ethynylene, 1-propynylene, 2-propynylene, 2-butynylene, 3-pentynylene, 4-hexynylene, 2-methyl-2-butynylene groups, and other alkynylene groups of straight chain or branched chain with 2 to 6 carbon atoms.

Examples of halogen atom include fluorine atom, bromine atom, chlorine atom, and iodine atom.

Examples of lower alkoxycarbonyl group include methoxycarbonyl, ethoxycarbonyl, propoxycarbonyl, isopropoxycarbonyl, butoxycarbonyl, tertiary butoxycarbonyl, pentyloxycarbonyl, hexyloxycarbonyl groups, and other alkoxycarbonyl group of which alkoxy portion is an alkoxy group of straight chain or branched chain with 1 to 6 carbon atoms.

Examples of thienyl group which may possess a halogen atom as a substituent include 5-fluoro-2-thienyl, 5-bromo-2-thienyl, 3-bromo-2-thienyl, 5-chloro-2-thienyl, 5-chloro-3-thienyl, 4-chloro-2-thienyl, 4-chloro-3-thienyl, 5-iodo-2-thienyl groups, and other thienyl group which may possess a halogen atom as a substituent.

Examples of saturated heterocyclic group of five members or six members that may further possess one hetero atom selected from the group consisting of nitrogen atom, oxygen atom and sulfur atom include 1-pyrrolidinyl, 1-piperidinyl, 1-imidazolidinyl, 1-piperadinyl, morpholino, and thiomorpholino groups.

Examples of lower alkanoyl group include formyl, acetyl, propanoyl, butanoyl, isobutanoyl, pentanoyl, hexanoyl groups, and other alkanoyl groups of straight chain or branched chain with 1 to 6 carbon atoms.

Examples of phenyl-lower alkyl group include benzyl, 2-phenylethyl, 1-phenylethyl, 3-phenylpropyl, 4-phenylbutyl, 5-phenylpentyl, 6-phenylhexyl, 2-methyl-3-phenylpropyl, 2-phenylpropyl groups, and other phenyl-lower alkyl groups of which alkyl portion is an alkyl group of straight chain or branched chain with 1 to 6 carbon atoms.

Examples of lower alkylenedioxy group include methylenedioxy, ethylenedioxy, trimethylenedioxy groups, and other alkylenedioxy groups with 1 to 3 carbon atoms.

Examples of phenyl-lower alkyl group which may possess a lower alkylenedioxy group as a substituent on the phenyl ring include, aside from the phenyl-lower alkyl group presented above, 2,3-methylenedioxybenzyl, 3,4-methylenedioxybenzyl, 3,4-ethylenedioxybenzyl, 3,4-trimethylenedioxybenzyl, 2-(3,4-methylenedioxyphenyl)ethyl, 3-(3,4-methylenedioxyphenyl)propyl, 4-(3,4-methylenedioxyphenyl)butyl, 5-(3,4methylenedioxyphenyl)pentyl, 6-(3,4-methylenedioxyphenyl)hexyl groups, and other alkyl groups of which alkyl portion is a straight chain or branched chain with 1 to 6 carbon atoms, and further examples may also include phenylalkyl groups which may possess an alkylenedioxy group with 1 to 3 carbon atoms as a substituent on the phenyl ring.

Examples of phenyl group which may possess one to three groups selected from the group consisting of halogen atom, hydroxy group, lower alkyl group, lower alkoxy group, carboxy group, lower alkoxycarbonyl group and lower alkylenedioxy group as substituent include 4-chlorophenyl, 3-chlorophenyl, 2-chlorophenyl, 2,4-dichlorophenyl, 3,5-dichlorophenyl, 2,4,6-trichlorophenyl, 3-iodephenyl, 3,5-diiodephenyl, 2-bromophenyl, 3,5-dibromopheny, 2,4,6-tribromophenyl, 4-fluorophenyl, 2-fluorophenyl, 2,6-difluorophenyl, 2,4,6-trifluorophenyl, 4-hydroxyphenyl, 2,4-dihydroxyphenyl, 4-methylphenyl, 3-ethylphenyl, 2-methylphenyl, 3,5-dimethylphenyl, 2,4,6-trimethylphenyl, 4-propylphenyl, 3-isopropylphenyl, 2-butylphenyl, 4-pentylphenyl, 3-hexylphenyl, 4-t-butyl-2-methylphenyl, 4-methoxyphenyl, 3-ethoxyphenyl, 2-methoxyphenyl, 3,5-dimethoxyphenyl, 2,4,6-trimethoxyphenyl, 4-propoxyphenyl, 3-isopropoxyphenyl, 2-butoxyphenyl, 4-pentyloxyphenyl, 3-hexyloxyphenyl, 4-t-butoxy-2-methoxyphenyl, 4-butyl-2-methoxyphenyl, 2-carboxyphenyl, 4-carboxyphenyl, 3,4-dicarboxyphenyl, 4-methoxycarbonylphenyl, 2-propoxycarbonylphenyl, 4-methoxycarbonyl-3-carboxyphenyl, 3,4-methylenedioxyphenyl, 2-methyl-3,4-methylenedioxyphenyl.

Examples of lower alkylthio group include methylthio, ethylthio, isopropylthio, butylthio, tertiary butylthio, pentylthio, hexylthio group and other alkylthio groups of straight chain or branched chain with 1 to 6 carbon atoms.

Examples of lower alkoxy-lower alkoxy group include methoxymethoxy, methoxyethoxy, ethoxymethoxy, ethoxyethoxy, methoxypropoxy, propoxymethoxy, butoxymethoxy, t-butoxypropoxy, butoxyethoxy, isopropoxypropoxy, propoxyethoxy, t-butoxymethoxy, pentyloxymethoxy, methoxypentyloxy, hexyloxymethoxy, methoxyhexyloxy, hexyloxyexyloxy, and other alkoxy-alkoxy group of which each alkoxy portion is alkoxy group of straight chain or branched chain with 1 to 6 carbon atoms.

Examples of lower alkoxy-lower alkoxy-lower alkoxy group include methoxymethoxymethoxy, methoxymethoxyethoxy, methoxyethoxyethoxy, ethoxyethoxymethoxy, ethoxyethoxyethoxy, methoxyethoxypropoxy, propoxymethoxyethoxy, isopropoxypropoxypropoxy, butoxyethoxymethoxy, t-butoxymethoxypropoxy, butoxyethoxymethoxy, isopropoxymethoxypropoxy, propoxyethoxyethoxy, t-butoxymethoxymethoxy, pentyloxyethoxyethoxy, methoxypentyloxypentyloxy, hexyloxymethoxyethoxy, methoxymethoxyhexyloxy, hexyloxyhexyloxyethoxy, and other alkoxy-alkoxy-alkoxy group of which each alkoxy portion is alkoxy group of straight chain or branced chain with 1 to 6 carbon atoms.

Examples of lower alkoxy-lower alkoxy-lower alkoxy-lower alkoxy group include methoxymethoxymethoxymethoxy, methoxyethoxymethoxyethoxy, methoxyethoxypropoxyethoxy, ethoxyethoxymethoxymethoxy, methoxyethoxyethoxyethoxy, methoxyethoxypropoxyporopoxy, propoxymethoxyethoxymethoxy, isopropoxy(2-methyl)propoxyethoxypropoxy, butoxyethoxyethoxymethoxy, t-butoxyethoxymethoxypropoxy, butoxyethoxymethoxybutoxy, isopropoxymethoxypropoxyethoxy, propoxyethoxyethoxyethoxy, t-butoxymethoxymethoxymethoxy, pentyloxyethoxyethoxyethoxy, methoxypentyloxypentyloxymethoxy, hexyloxymethoxyethoxyhexyloxy, methoxymethoxyhexyloxymethoxy, hexyloxyhexyloxyethoxyethoxy, and other alkoxy-alkoxy-alkoxy-alkoxy group of which each alkoxy portion is alkoxy group of straight chain or branched chain with 1 to 6 carbon atoms.

Examples of alkyl group with 1 to 12 carbon atoms include methyl, ethyl, propyl, isopropyl, butyl, tertiary butyl, pentyl, 2,4-dimethylpentyl, hexyl, 3-methylhexyl, 2,3, 6-trimethylhexyl, heptyl, 4-isobutylheptyl, octyl, 2-ethyloctyl, nonyl, decyl, undecyl, dodecyl, and other alkyl groups of straight chain or branched chain with 1 to 12 carbon atoms.

Examples of lower alkoxy-lower alkyl group include methoxymethyl, ethoxymethyl, isopropoxyethyl, methoxyethyl, 3-ethoxypropyl, 2-methoxybutyl, tertiary butoxyethyl, 5-methoxypentyloxy, 3-methoxypentyloxy, 4-methoxyhexyloxy, 2-propoxyexyloxy, and other alkoxy-alkyl groups wherein each of alkoxy group and alkyl group is straight chain or branched chain with 1 to 6 carbon atoms.

Meanwhile, if n denotes 2, $R^4$ indicates a similar group or a different group.

Compounds expressed in formula (1) include all of stereoisomer, optical isomer, and geometrical isomer.

The compounds and material compounds of the invention may be manufactured in various methods, and for example, the compounds of the invention may be manufactured by the method shown in reaction scheme 1 or reaction scheme 2 below.

Reaction Scheme 1

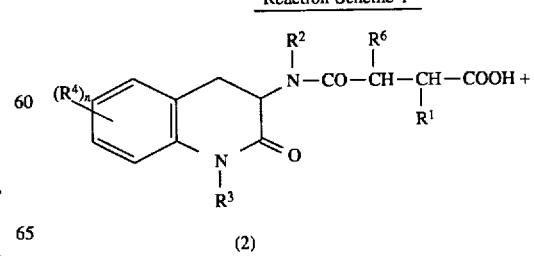

(2)

-continued
Reaction Scheme 1

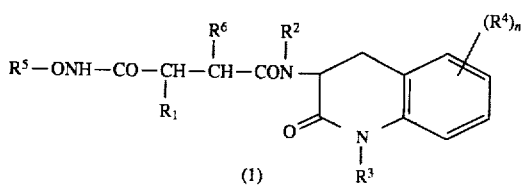

[where $R^1$, $R^2$, $R^3$, $R^4$, $R^5$, $R^6$ and n are same as defined above.]

The method shown in reaction scheme 1 is a method of reaction between the amine compound of formula (3) and the carboxylic acid of formula (2) by ordinary amide bond formation reaction.

In the amide bond formation reaction, the condition of the known amide bond formation reaction can be easily applied. For example, (i) a mixed acid anhydride method, that is, a method of reaction of carboxylic acid (2) with alkylhalocarboxylic acid to form a mixed acid anhydride, which is allowed to react with amine (3), (ii) an active ester method, that is, a method of changing carboxylic acid (2) into an active ester such as p-nitrophenyl ester, N-hydroxysuccinimide ester, and 1-hydroxybenzotriazole ester which is allowed to react with amine (3), (iii) a carbodiimide method, that is, a method of condensation reaction of carboxylic acid (2) with amine (3) in the presence of activator such as dicyclohexylcarbodiimide and carbonyldiimidazole, and (iv) other methods, such as a method of reaction of carboxylic acid (2) with dehydrating agent such as acetic anhydride to form carboxylic anhydride, which reacts with amine (3), a method of reaction of ester by carboxylic acid (2) and lower alcohol with amine (3), and a method of reaction of acid halide of carboxylic acid (2), that is, carboxylic halide with amine (3). Among these methods, the active ester method or mixed acid anhydride method is preferred.

The mixed acid anhydride used in the mixed acid anhydride method (i) is obtained by an ordinary Schotten-Baumann reaction, and by reacting with amine (3) without isolating, usually, the compound in formula (1) is obtained. The Schotten-Baumann reaction is conducted in the presence of an basic compound. Usable basic compounds are conventional compounds used in Schotten-Baumann reaction, including triethylamine, trimethylamine, pyridine, dimethyl aniline, N-methyl morpholine, 1,5-diazabicyclo[4,3,0] nonene-5 (DBN), 1.8-dizaibicyclo[5,4,0]undecene-7 (DBU), 1,4-diazabicyclo [2,2,2]-octane (DABCO), other organic bases, potassium carbonate, sodium carbonate, potassium hydrogencarbonate, sodium hydrogencarbonate, and other inorganic bases. The reaction is performed generally at about −20° to 100° C., preferably 0° to 50° C., and the reaction time is about 5 minutes to 10 hours, preferably 5 minutes to 2 hours. The reaction between the obtained mixed acid anhydride and amine (3) is usually conducted at about −20° to 150° C., preferably 10° to 50° C., and the reaction time is about 5 minutes to 10 hours, preferably 5 minutes to 5 hours. The mixed acid anhydride method is generally conducted in a solvent. The usable solvents are all conventional solvents used in mixed acid anhydride, and specific examples include chloroform, dichloromethane, dichloroethane and other halogenated hydrocarbons; benzene, toluene, xylene and other aromatic hydrocarbons; diethyl ether, diisopropyl ether, tetrahydrofurane, dimethoxyethane and other ethers; methyl acetate, ethyl acetate, other esters; N,N-dimethyl formamide, dimethyl sulfoxide, acetonitrile, hexamethylphosphoric acid triamide and other non-protonic polar solvent; and their mixed solvents. Examples of alkylhalocarboxylic acid to be used in mixed acid anhydride method include methyl chloroformate, methyl bromoformate, ethyl chloroformate, ethyl bromoformate, and isobutyl chloroformate. As the blending rate of the carboxylic acid (2) and alkylhalocarboxylic acid (3) used in this method, equal mols should be used generally, but the alkylhalocarboxylic acid and carboxylic acid (2) may be used in a range of 0.5 to 1 mol to amine (3).

Among other methods (iv), in the case of the method of reaction of carboxylic acid halide with amine (3), this reaction is carried out in the presence of a basic compound, in a proper solvent. As the basic compound, known compounds may be widely used, and for example, aside from the basic compound used in the Schotten-Baumann reaction, sodium hydroxide, potassium hydroxide, sodium hydride, and potassium hydride may be used. As the solvent, aside from the solvent used in the mixed acid anhydride method, for example, methanol, ethanol, propanol, butanol, 3-methoxy-1-butanol, ethyl cellosolve, methyl cellosolve and other alcohols; pyridine; acetone; and water may be used. The blending rate of amine (3) and carboxylic acid halide is not particularly limited, and may be selected in a wide range, and the latter should be used at least by equal mol to the former, preferably 0.5 to equal mol. The reaction is usually conducted at about −20° to 180° C., preferably 0° to 150° C., and the reaction is generally terminated in about 5 minutes to 30 hours.

In the case of the method of reaction of the ester obtained from carboxylic acid (2) and lower alcohol with amine (3), the reaction is conducted in a proper solvent, in the presence of a basic compound. Examples of the basic compound include sodium hydroxide, potassium hydroxide, sodium alcoholate, and potassium alcoholate. Examples of solvent include methanol, ethanol and other alcohols; tetrahydrofurane, dioxane and other ethers; and dimethyl formamide and other polar solvents. The blending rate of amine (3) and carboxylic acid ether is not particularly limited, and may be selected in a wide range, but usually the former should be used at least an equal mol of the latter, preferably 2 to 5 times mol. The quantity of use of the basic compound may be about 1 to 3 times mol of the carboxylic acid ester. The reaction is conducted usually at about −20° to 180° C., preferably about 0° to 40° C., and the reaction is usually terminated in about 5 minutes to 30 hours.

The amide bond formation reaction shown in reaction scheme 1 may be also executed by a method of reaction between carboxylic acid (2) and amine (3) in the presence of condensation agent, such as triphenylphosphine, diphenyl phosphinyl chloride, phenyl-N-phenyl phosphoramide chloridate, diethyl chlorophosphenite, diethyl cyanophosphate, azide diphenyl phosphate, bis (2-oxo-3-oxazolidinyl) phosphinic chloride, and other phosphorus compounds.

This reaction is conducted in the presence of the solvent and basic compound used in the method of reaction of carboxylic acid halide with amine (3), usually at about −20° to 150° C., preferably about 0° to 100° C., and the reaction is usually terminated in about 5 minutes to 30 hours. The content of the condensation agent and carboxylic acid (2) may be at least about an equal mol of amine (3), preferably about equal mol to double mol.

Reaction Scheme 2

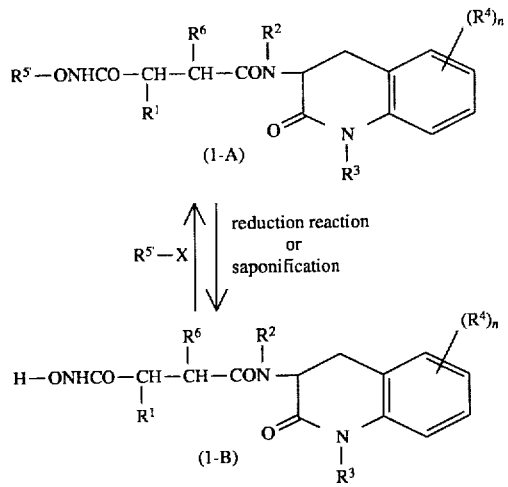

[where $R^1$, $R^2$, $R^3$, $R^4$, $R^6$, and n are same as defined above; $R^{5'}$ denotes benzoyl group, lower alkanoyl group or phenyl-lower alkyl group; and X is a halogen atom.]

The reaction of transforming the compound of formula (1-A) into the compound of formula (1-B) is effected by presenting the compound of formula (1-A) for ordinary reduction reaction or saponification reaction.

In the reduction reaction, the conditions of the known reduction reaction may be easily applied. For example, a catalytic reduction can be conducted in a proper solvent, in the presence of a catalyst. Ordinary solvents can be widely used, for example, methanol, ethanol, isopropanol and other alcohols; hexane, cyclohexane, other hydrocarbons; diethylene glycol dimethyl ether, dioxane, tetrahydrofurane, diethyl ether and other ethers; methyl acetate, ethyl acetate and other esters; N,N-dimethyl formamide and other polar solvents; water; acetic acid; and their mixed solvents. Examples of reducing catalyst include palladium, palladium-black, palladium-carbon, platinum, platinum oxide, copper chromite, and Raney nickel. The quantity of use of such catalyst may be about 0.001 to 2 times of the weight of the compound of formula (1-A). The reaction may be conducted under pressure, but when performing at ordinary pressure, the reaction temperature may be about 10° to 60° C., preferably 20° to 40° C., and the reaction is terminated generally in about 1 hour to 5 days. Besides, when a hydrogen supply source such as cyclohexene, cyclohexadiene, formic acid, ammonium formate, and isopropyl alcohol is used, it may be conducted in a proper solvent, in the presence of a catalyst. As the solvent, the same solvent as in the catalytic reduction may be used. Examples of catalyst include palladium, palladium-black, and palladium-carbon. The quantity of use of the catalyst may be about 0.01 to 2 times of the weight of the compound of formula (1-A), the reaction temperature is about 10° to 100° C. and the reaction is generally terminated in about 1 minute to 3 days.

In saponification reaction, the conditions of ordinary saponification may be widely applied. For example, using an ordinary basic compound, the reaction may be conducted. Examples of basic compound include sodium hydroxide, potassium hydroxide, sodium carbonate, potassium carbonate, and other inorganic bases. The quantity of use of such basic compound may be about 1 to 6 mols in 1 mol of the compound in formula (1-A). The reaction is usually conducted at about −10° to 50° C. and the reaction is generally terminated in about 30 minutes to 24 hours.

The reaction for transforming the compound in formula (1-B) into the compound in formula (1-A) is conducted in a proper solvent, in the presence of a basic compound, by reaction between the compound expressed in a formula $R^{5'}$-X or $(R^{5'})_2O$ [where $R^{5'}$ and X are same as defined above] and the compound in formula (1-B). Examples of solvent include polar solvents such as N,N-dimethyl formamide, and halogenated hydrocarbons such as dichloromethane. Examples of basic compound include pyridine, triethylamine, N-methylmorpholine, and other organic bases. The quantity of use of such basic compound may be about 1 to 3 times mol in 1 mol of the compound in formula (1-B). The reaction temperature may be −10° to 50° C. and the reaction is generally terminated in about 10 minutes to 24 hours.

The compound in formula (2) which is a starting material in reaction scheme 1 may be manufactured in various methods. For example, it may be manufactured in the methods shown in the reaction schemes 4, 6, 7, 8, and 9.

Reaction scheme 3

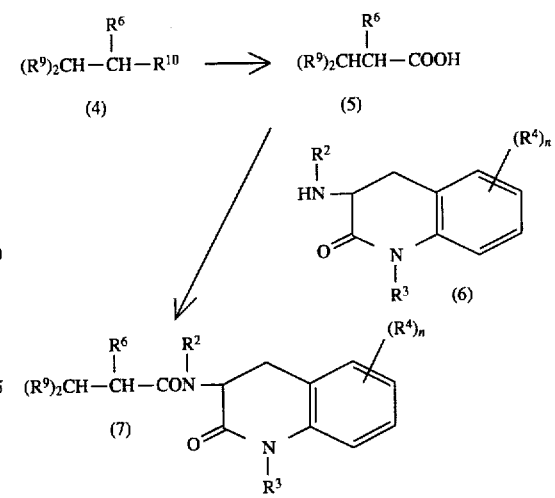

[where $R^2$, $R^3$, $R^4$, $R^6$ and n are same as defined above; and $R^9$ and $R^{10}$ denote selectively eliminatable ester groups such as phenyl-lower alkoxycarbonyl group and lower alkoxycarbonyl group.]

The compound in formula (5) is manufactured by eliminating the protective group of carboxyl group of the compound in formula (4). For elimination of protective group, the method of eliminating the protective group of ordinary carboxyl group may be widely applied, for example, the method of treating with acid, the method of using catalytic reduction, and the method by saponification.

In the case of the method of treating with acid, the compound in formula (5) may be manufactured by treating the compound in formula (4) in the presence of the acid, in a proper solvent or without using solvent. Examples of acid may include organic acid such as trifluoroacetic acid, and inorganic acid such as hydrogen fluoride and hydrogen chloride. The acid may be used excessively to 1 mol of the compound in formula (4). Ordinary solvents may be widely used, including halogenated hydrocarbons such as dichloromethane, ethers such as dioxane, esters such as ethyl acetate, acetic acid, and others. The reaction proceeds usually around −40° to 60° C., preferably −20° to 40° C., and the reaction is generally terminated in about 1 minute to 5 hours.

In the case of the method of using catalytic reduction, the conditions of known reduction reaction may be widely applied. For example, the reaction may be conducted in the same condition as in the reduction reaction shown in reaction scheme 2.

In the case of the method of using saponification, the conditions of the ordinary saponification may be widely applied. For example, an ordinary basic compound may be used. Examples of basic compound include sodium hydroxide, potassium hydroxide, sodium carbonate, potassium carbonate, and other inorganic bases. The quantity of use of such basic compound may be about 1 to 3 mols in 1 mol of the compound in formula (4). The reaction is generally conducted at about $-10°$ to $50°$ C. and the reaction is generally terminated in about 30 minutes to 24 hours.

The compound in formula (7) may be prepared by reaction between the compound in formula (5) and the compound in formula (6) by ordinary amide bond formation reaction. The amide bond formation reaction can be conducted in the same manner as in the method of reaction scheme 1.

Reaction scheme 4

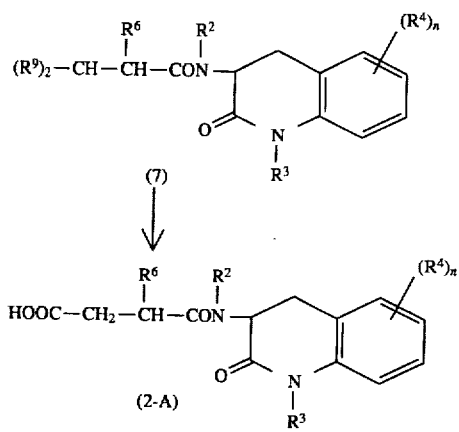

[where $R^2$, $R^3$, $R^4$, $R^6$, $R^9$, and n are same as defined above.]

The compound in formula (2-A) is manufactured by presenting the reaction in formula (7) for elimination reaction of carboxyl protective group in a proper solvent, and heating the reaction product after elimination reaction in a proper solvent.

In the elimination reaction of the carboxyl protective group, the conditions of known elimination reaction of carboxyl protective group may be widely applied. For example, the elimination reaction of the carboxyl protective group is conducted in the same manner as the elimination reaction of the carboxyl protective group shown in reaction scheme 3.

As the solvent when heating the reaction product after elimination reaction of carboxyl protective group, aromatic hydrocarbons such as toluene and benzene may be used. The reaction temperature is about $50°$ to $120°$ C. and it is preferred to react while refluxing. Generally, the reaction is terminated in about 1 minute to 3 days.

Reaction scheme 5

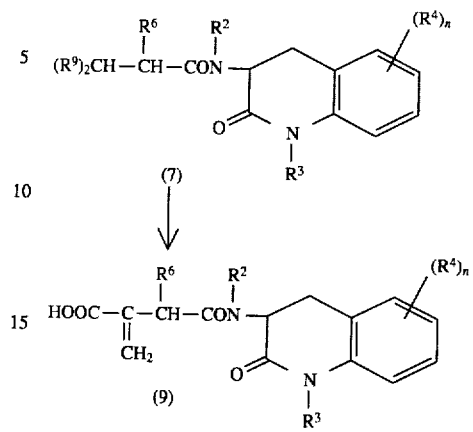

[where $R^2$, $R^3$, $R^4$, $R^6$, $R^9$ and n are same as defined above.]

The compound in formula (9) is manufactured by presenting the compound in formula (7) to elimination reaction of carboxyl protective group in a proper solvent, subjecting the reaction product after the elimination reaction to Mannich reaction with aliphatic secondary amine in a proper solvent, in the presence of formaldehyde, and heating the reaction product after the Mannich reaction.

In the elimination reaction of the carboxyl protective group, the conditions of known elimination reaction of carboxyl protective group may be widely applied. For example, the elimination reaction is conducted in the same manner as the elimination reaction of carboxyl protective group shown in reaction scheme 3. When presenting the reaction product after the elimination reaction of carboxyl protective group to Mannich reaction, as the solvent, for example, water, methanol, ethanol, isopropanol and other alcohols may be used, and as the aliphatic secondary amine, for example, dimethylamine, diethylamine, and piperidine may be used. The quantity of use of the aliphatic secondary amine may be about 1 to 2 times mol of the compound in formula (7). The quantity of use of formaldehyde is about 1 to 2 times mol of the compound in formula (7). The reaction temperature is $10°$ to $60°$ C., preferably about $20°$ to $40°$ C., and the reaction is generally terminated in about 1 hour to 3 days.

When heating the reaction product after the Mannich reaction, the reaction solution finishing the Mannich reaction may be heated or refluxed at reaction temperature of about $50°$ to $120°$ C. Generally, the reaction is terminated in about 1 minute to 1 day.

Reaction scheme 6

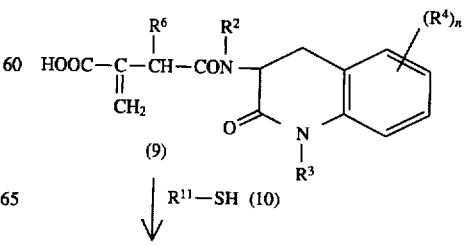

Reaction scheme 6

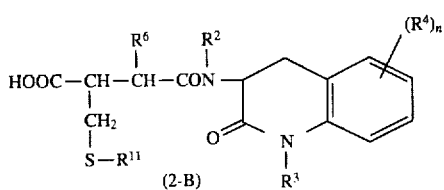

[where $R^2$, $R^3$, $R^4$, $R^6$, and n are same as defined above; and $R^{11}$ denotes thienyl group, lower alkanoyl group, phenyl group, or lower alkyl group.]

The compound in formula (2-B) is manufactured by reaction between the compound in formula (9) and the compound in formula (10) in a proper solvent or without using solvent. Examples of solvent include methanol, ethanol, and other alcohols. The quantity of use of the compound in formula (10) is excessive to 1 mol of the compound in formula (9) or equivalent to the solvent amount. The reaction is usually conducted at 10° to 120° C., preferably 20° to 100° C., and the reaction is generally terminated in about 1 hour to 10 days in a dark place.

The compound of which $R^1$ denotes a lower alkyl group in the compound in formula (2) is obtained by presenting the compound in formula (9) to ordinary reduction reaction. In this reduction reaction, the reaction conditions of ordinary reduction reaction may be widely employed, for example, same as in the reduction condition shown in reaction scheme 2.

Reaction scheme 7

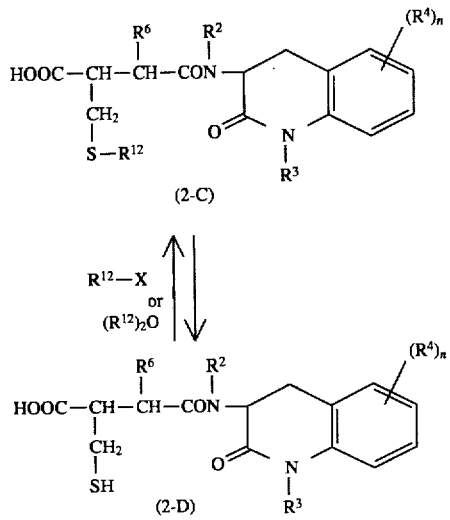

[where $R^2$, $R^3$, $R^4$, $R^6$, X and n are same as defined above; and $R^{12}$ denotes lower alkanoyl group or lower alkyl group.]

The reaction to obtain the compound in formula (2-D) from the compound in formula (2-C) is effected by saponification or in the presence of amine in a proper solvent. In the case of saponification, the reaction conditions of ordinary saponification reaction may be widely applied, and it may be performed same as in the saponification reaction in, for example, reaction scheme 3. When performing in the presence of amine, usable solvents include methanol, ethanol, and other alcohols. Examples of amine include methylamine, ethylamine, and other aliphatic amines. The quantity of use of amine may be excessive to 1 mol of the compound shown in formula (2-C). The reaction is usually conducted at about −20° to 100° C. and the reaction is generally terminated in about 1 minute to 24 hours.

The reaction to obtain the compound in formula (2-C) from the compound in formula (2-D) is effected by the reaction between the compound expressed in a formula $R^{12}$-X or $(R^{12})_2O$ [where $R^{12}$ and X are same as defined above] and the compound in formula (2-D) in a proper solvent, in the presence of a basic compound. Examples of the solvent include halogenated hydrocarbons such as chloroform, aromatic hydrocarbons such as benzene and toluene, ethers such as tetrahydrofurane, esters such as ethyl acetate, and polar solvents such as N,N-dimethyl formamide. Examples of the basic compound include organic bases such as triethyl amine, and inorganic bases such as potassium carbonate and sodium carbonate. The quantity of use of the basic compound is about 2 to 5 mols in 1 mol of the compound in formula (2-D). The reaction is conducted usually at about 0° to 100° C. and the reaction is generally terminated in about 1 minute to 24 hours.

Reaction scheme 8

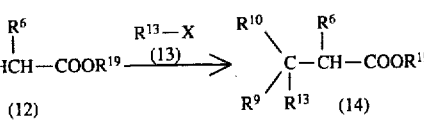

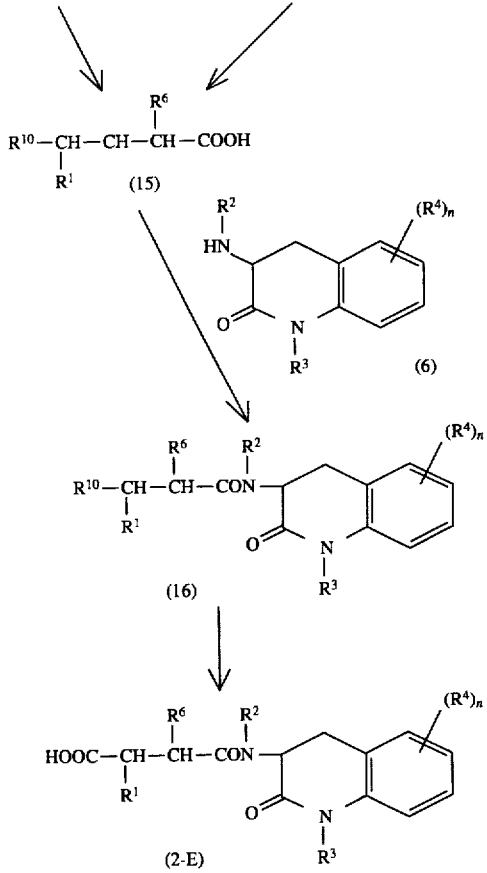

where $R^1$, $R^2$, $R^3$, $R^4$, $R^6$, $R^9$, $R^{10}$, X and n are same as defined above; $R^{13}$ denotes a group —A—$R^{1a}$ (A and $R^{1a}$ same as defined above); and $R^{19}$ shows lower alkyl group or phenyl-lower alkyl group.]

The compound in formula (14) is manufactured by reaction between the compound in formula (12) and the compound in formula (13) in a proper solvent, in the presence of a basic compound. Examples of the basic compound include sodium hydride, potassium hydride, lithium hydride, sodium methylate, and potassium ethylate. Examples of the solvent include ethers such as tetrahydrofurane, and polar solvents such as dimethyl formamide. The quantity of use of the basic compound is 1 to 3 times mol in 1 mol of the compound in formula (12), preferably an equivalent mol. The quantity of use of the compound in formula (13) is 1 to 3 times mol in 1 mol of the compound in formula (12), preferably an equivalent mol. The reaction temperature is usually about 0° to 120° C., preferably about 20° to 60° C. Generally, the reaction is terminated in about 1 hour to 5 days.

The compound in formula (15) is manufactured by presenting the compound in formula (12) or the compound in formula (14) for elimination reaction of carboxyl protective group in a proper solvent, and heating the reaction product after the elimination reaction in a proper solvent. In the elimination reaction of carboxyl protective group, the conditions of known elimination reaction of carboxyl protective group may be widely applied, and the elimination reaction may be conducted same as in the reaction shown in, for example, reaction scheme 3. The heating reaction of the reaction product after elimination reaction of carboxyl protective group may be conducted same as in the reaction shown in reaction scheme 4.

The compound in formula (16) is manufactured by reaction between the compound in formula (15) and the compound in formula (6) by an ordinary amide bond formation reaction. The amide bond formation reaction may be performed same as in the method of reaction scheme 1.

The compound in formula (2-E) is manufactured by presenting the reaction in formula (16) for elimination reaction of carboxyl protective group in a proper solvent. This reaction is conducted same as the elimination reaction of carboxyl protective group shown in reaction scheme 3.

The compound in formula (15) used in reaction scheme 8 may be manufactured in various methods. For example, by the method shown below, it is manufactured in the same reaction conditions as in the reactions corresponding to those disclosed in WO-9309097.

That is, $R^6CH_2COOH$ is first treated by halogenating reagent to obtain an acid halide, which is caused to react with an optically active oxazolidine-2-on in the presence of n-butyl lithium to obtain $R^6CH_2COZ$, which is then caused to react with α-haloacetate $XCH_2R^{10}$ to obtain $R^{10}CH_2CH(R^6)COZ$, and this compound is hydrolyzed to remove an optically active oxazolidine-2-on, thereby obtaining $R^{10}CH_2CH(R^6)COOH$ [where $R^6$, $R^{10}$, and X are same as defined above; and Z denotes an optically active 2-oxo-oxazolidyl group].

Reaction scheme 9

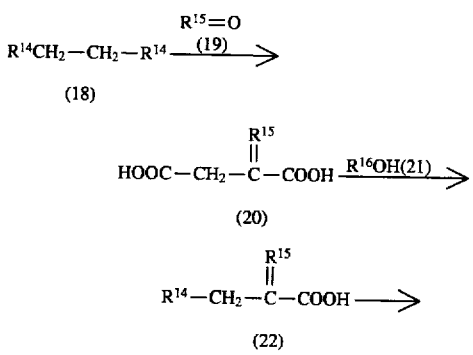

-continued
Reaction scheme 9

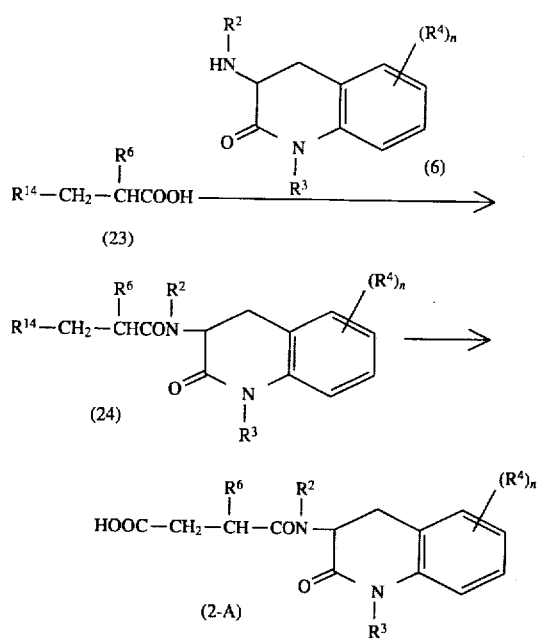

[where $R^2$, $R^3$, $R^4$, $R^6$, and n are same as defined above; $R^{14}$ denotes a lower alkoxycarbonyl group; $R^{15}$ is alkylidene group with 1 to 12 carbon atoms, lower alkoxy-lower alkylidene group, or phenyl-lower alkylidene group which may possess lower alkylenedioxy group on a phenyl ring as a substituent; and $R^{16}$ is a lower alkyl group.]

The compound in formula (20) is obtained by reaction between the compound in formula (18) and the compound in formula (19) in a proper solvent in the presence of a basic compound, and subsequent saponification (alkaline hydrolysis). Proper solvents may include methanol, ethanol, isopropyl alcohol, tert-butyl alcohol, and other alcohols. Examples of the basic compound include sodium hydride, potassium hydride, lithium hydride, sodium methylate, and potassium ethylate. The quantity of use of the compound in formula (19) is about 1 to 1.5 mol in 1 mol of the compound in formula (18). The quantity of use of the basic compound is about 1 to 1.5 mol in 1 mol of the compound in formula (18). The reaction is conducted usually at about 10° to 120° C. and the reaction is generally terminated in about 1 minute to 24 hours.

The subsequent saponification is performed by using, for example, an ordinary basic compound. Examples of the basic compound include sodium hydroxide, potassium hydroxide, sodium carbonate, potassium carbonate, and other inorganic bases. The quantity of use of the basic compound may be 2 to 6 mols in 1 mol of the compound in formula (18). The reaction is usually conducted at about 0° to 100° C. and the reaction is generally terminated in about 1 to 24 hours.

The compound in formula (22) is manufactured by causing the compound in formula (20) to react with dehydration condensation agent such as acetic anhydride and N,N'-dicyclohexyl carbodiimide (DCC), and presenting the reaction product for reaction with the compound in formula (21). In the reaction between the compound in formula (20) and acetic anhydride or DCC, the quantity of use of acetic anhydride or DCC may be 1 mol or excessive to 1 mol of the compound in formula (20). The reaction proceeds at about 20° to 120° C., and the reaction is generally terminated in about 1 minute to 10 hours. In the reaction between the reaction product and the compound in formula (21), the quantity of use of the compound in formula (21) may be excessive to 1 mol of the compound in formula (20). The reaction is usually conducted at 10° to 100° C. and the reaction is generally terminated in about 1 to 24 hours.

The compound in formula (23) is obtained by presenting the compound in formula (22) to an ordinary reduction reaction. In this reduction reaction, the conditions of the known reduction reaction may be widely applied. For example, the reaction may be conducted in the same manner as in reaction scheme 2.

The compound in formula (24) is obtained by the reaction between the compound in formula (23) and the compound in formula (6) by ordinary amide bond formation reaction. The amide bond formation reaction is done in the same manner as in reaction scheme 1.

The compound in formula (2-A) is manufactured by treating the compound in formula (24) in a proper solvent, in the presence of a basic compound. Examples of the proper solvent include methanol, ethanol, and other alcohols. Examples of the basic compound include inorganic bases such as sodium hydroxide and potassium hydroxide, and organic bases such as triethyl amine. The quantity of use of the basic compound may be about 1 to 3 mols of 1 mol of the compound in formula (24). The reaction is usually performed at about 0° to 40° C. and the reaction is generally terminated in about 1 to 24 hours.

The compound in formula (4) used as a starting material in reaction scheme 3 is manufactured in various methods. For example, it may be manufactured in the method shown in reaction scheme 10.

Reaction scheme 10

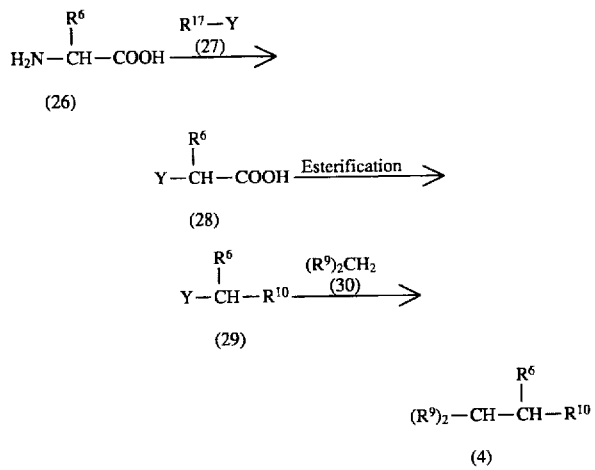

[where $R^6$, $R^9$ and $R^{10}$ are same as defined above; $R^{17}$ is an alkaline metal such as sodium, potassium or the like; and Y denotes a halogen atom.]

The compound in formula (28) is manufactured by presenting the compound in formula (26) and the compound in formula (27) for an ordinary diazo coupling reaction in a proper solvent in the presence of a nitrite.

Examples of the nitride include sodium nitrite and potassium nitrite. The quantity of use of the nitride is about 1 to 1.5 mol in 1 mol of the compound in formula (26), and the quantity of use of the compound in formula (27) is about 1 to 1.5 mol in 1 mol of the compound in formula (26). Examples of the solvent may include water, hydrochloric acid, sulfuric acid, other acidic solvents, and their mixed solvents. The reaction is usually conducted at about −10° to 100° C. and the reaction is generally terminated in about 1 minute to 1 day.

The compound in formula (29) is manufactured by presenting the compound in formula (28) for an ordinary esterification reaction in a proper solvent.

The compound in formula (4) is manufactured by reaction between the compound in formula (29) and the compound in formula (30) in a proper solvent, in the presence of a basic compound. Examples of the solvent include polar solvents such as dimethylformamide, and halogenated hydrocarbons such as dichloromethane. Examples of the basic compound include sodium hydride and potassium t-butoxide. The quantity of use of the basic compound is about 1 to 3 mols in 1 mol of the compound in formula (29). The reaction is conducted usually at about −20° to 70° C. and the reaction is generally terminated in about 1 hour to 10 days.

The compound in formula (12) used as a starting material in reaction scheme 8 is manufactured in various methods. For example, it is manufactured in the method shown in reaction scheme 11 below.

Reaction scheme 11

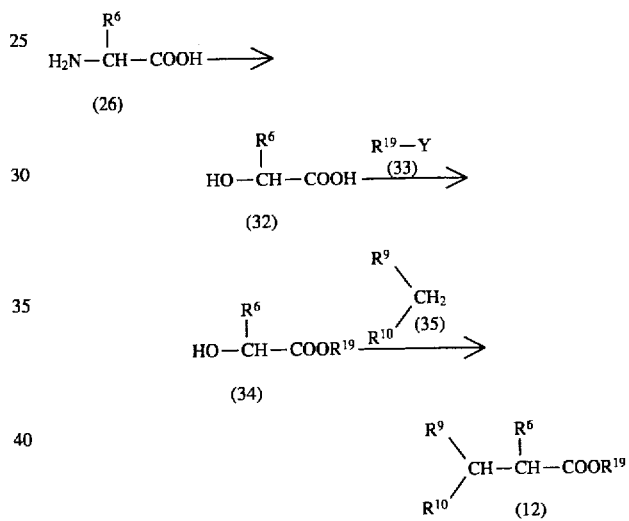

[where $R^6$, $R^9$, $R^{10}$, $R^{19}$, and Y are same as defined above.]

The compound in formula (32) is manufactured by presenting the compound in formula (26) for an ordinary diazo coupling reaction in a proper solvent in the presence of a nitrite. The diazo coupling reaction is conducted in the same reaction conditions as in manufacture of the compound in formula (28) in reaction scheme 10.

The compound in formula (34) is manufactured by reaction between the compound in formula (32) and the compound in formula (33) in a proper solvent, in the presence of a basic compound. Examples of the solvent include ethers such as tetrahydrofurane, and aromatic hydrocarbons such as benzene and toluene. Examples of the basic compound include organic bases such as triethyl amine and N-methylmorpholine. The quantity of use of the basic compound is about 1 to 2 mols of 1 mol of the compound in formula (32), and the quantity of use of the compound in formula (33) is about 1 to 2 mols of 1 mol of the compound in formula (32). The reaction temperature is about 0° to 100° C. and the reaction is generally terminated in about 1 to 24 hours. The compound in formula (34) may be also manufactured by presenting for an ordinary esterification reaction in a proper solvent.

The compound in formula (12) is manufactured by transforming the compound in formula (34) into sulfonate ester, and reacting with the compound in formula (35) in the presence of a basic compound. The reaction of transforming the compound in formula (34) into sulfonate ester is realized by reaction with acid anhydride such as sulfonic anhydride and acid halide such as sulfonyl halide, in a proper solvent, in the presence of a basic compound. Examples of the solvent include halogenated hydrocarbons such as dichloromethane, and ethers such as tetrahydrofurane. Examples of the basic compound include organic bases such as pyridine, triethylamine, and N-methylmorpholine. The quantity of use of the basic compound is about 1 to 1.5 mol of 1 mol of the compound in formula (34). The quantity of use of acid anhydride or acid halide is about 1 to 1.5 mol of 1 mol of the compound in formula (34). The reaction temperature is about –50° to 50° C. and the reaction is generally terminated in about 1 minute to 1 day.

The reaction between the sulfonate ester of the compound in formula (34) and the compound in formula (35) is conducted in a proper solvent, in the presence of a basic compound. Examples of the solvent include polar solvent such as dimethyl formamide and halogenated hydrocarbons such as dichloromethane. Examples of the basic compound include sodium hydride, potassium hydride, lithium hydride, sodium methylate, and potassium ethylate. The quantity of use of the basic compound is about 1 to 2 mols in 1 mol of the compound in formula (34), and the quantity of use of the compound (35) is about 1 to 2 mols in 1 mol of the compound in formula (34). The reaction temperature is about –10° to 50° C. and the reaction is generally terminated in about 1 hour to 10 days.

The compound in formula (6) used in reaction schemes 3, 8 and 9 is a novel or known compound, which may be easily manufactured in a method disclosed, for example, in J. Med. Chem., 1972, 15, 325, or J. Org. Chem., 1989, 54, 3394. The compound in formula (6) is manufactured in methods shown in the following reaction schemes 12 and 13.

Reaction scheme 12

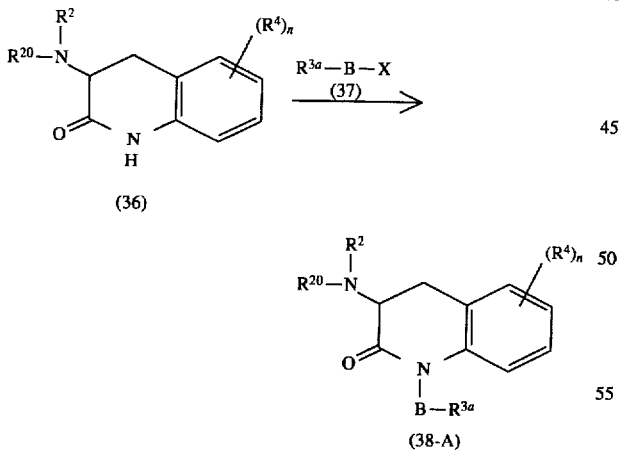

[where $R^2$, $R^4$, $R^{3a}$, B, X, and n are same as defined above; and $R^{20}$ denotes acyl group or amino group protective group.]

The reaction between the compound in formula (36) and the compound in formula (37) is conducted in a proper solvent, in the presence of a basic compound. Examples of the solvent are dioxane, tetrahydrofurane, diethyl ether, ethylene glycol dimethyl ether and other ethers; dimethyl formamide, dimethyl sulfoxide, hexamethylene phosphoric acid triamide and other polar solvents. Examples of the basic compound include sodium hydride, potassium hydride, lithium hydride, sodium methylate, potassium ethylate, and other inorganic bases. The quantity of use of such basic compound is usually about 0.5 to 2 times mol of the compound in formula (36), preferably an equivalent mol. The blending rate of the compound in formula (36) and the compound in formula (37) is 1 to 3 times the mol of the latter to the former, preferably about an equivalent mol. The reaction temperature is usually about –20° to 120° C., preferably about 0° to 60° C., and the reaction is generally terminated in about 10 minutes to 5 days.

Reaction scheme 13

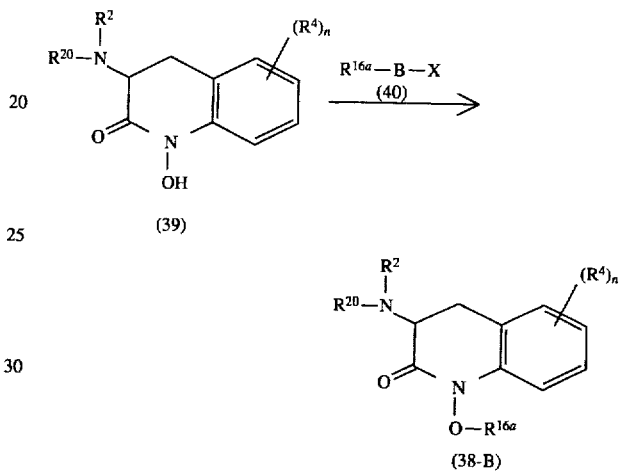

[where $R^2$, $R^4$, $R^{20}$, X and n are same as defined above; and $R^{16a}$ denotes lower alkyl group, lower alkoxy-lower alkyl group, lower alkoxy-lower alkoxy-lower alkyl group, or lower alkoxy-lower alkoxy-lower alkoxy-lower alkyl group.]

The reaction between the compound in formula (39) and the compound in formula (40) can be conducted in the same reaction conditions as in the reaction between the compound in formula (36) and the compound in formula (37) in reaction scheme 12.

The compound in formula (38-A) and the compound in formula (38-B) are transformed into the compound in formula (6) by an ordinary de-protection reaction.

The compound in formula (15) used in reaction scheme 8 is manufactured in various methods. For example, it is manufactured in the method shown in the following reaction scheme 14.

Reaction scheme 14

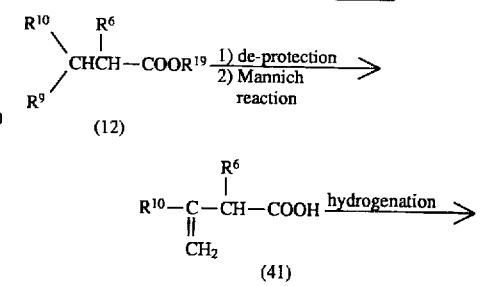

-continued
Reaction scheme 14

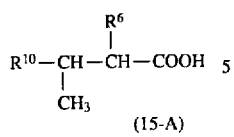

(15-A)

[where $R^6$, $R^9$, $R^{10}$, and $R^{19}$ are same as defined above.]

The de-protection of the compound in formula (12) can be effected in the same conditions as in the reaction for obtaining the compound in formula (5) from the compound in formula (4) in reaction scheme 3. The subsequent Mannich reaction can be effected in the reaction conditions same as the reaction for obtaining the compound in formula (9) from the compound in formula (7) in reaction scheme 5. The hydrogenation of the compound in formula (41) can be effected in the same conditions as in the reaction for reducing the compound in formula (1-A) to transform into the compound in formula (1-B) in reaction scheme 2.

The amino group, hydroxyl group or other substituent in the intermediate compound shown in the foregoing reaction schemes can be properly protected by an ordinary method not affecting the reaction, and the protective group may be properly eliminated in an ordinary method after reaction.

The compound in formula (1) of the invention, and the intermediate compounds shown in the reaction schemes for its manufacture may be variously changed in the types of $R^1$, $R^3$, $R^5$, and others contained therein, but they are not limited to them alone, and various changes as effected ordinarily may be applicable.

For example, as the elimination reaction of the protective group of the hydroxyl group, there is an example of de-silylation reaction for obtaining the compound in formula (1-B) from the compound in formula (42) in reaction scheme 15.

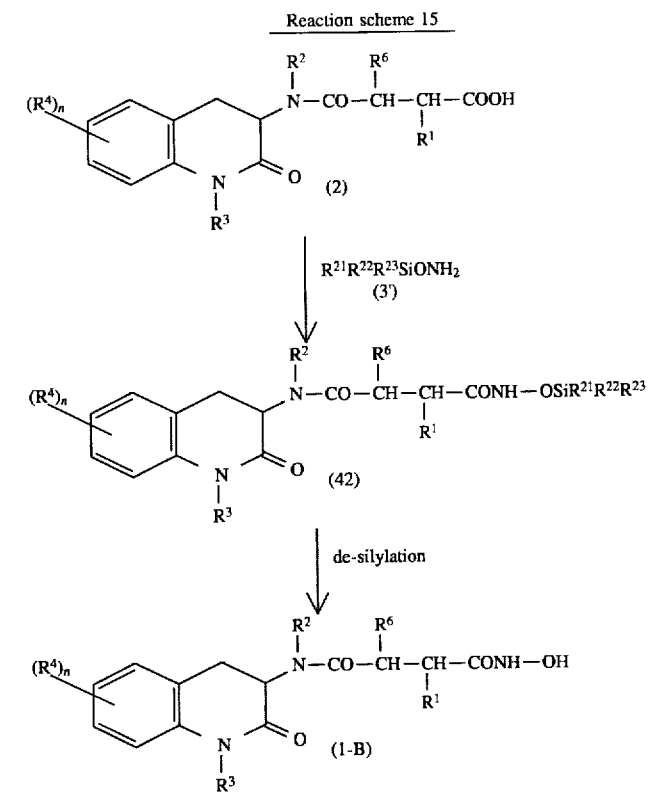

[where $R^1$, $R^2$, $R^3$, $R^4$, $R^6$ and n are same as defined above; and $R^{21}$, $R^{22}$, and $R^{23}$ are lower alkyl groups.]

The reaction between the compound in formula (2) and the compound in formula (3') can be effected in the same reaction conditions as in the reaction between the compound in formula (2) and the compound in formula (3) in reaction scheme 1.

In the reaction for leading the compound in formula (42) into the compound in the formula (1-B), the reaction conditions in ordinary de-silylation may be applied. For example, this de-silylation reaction is effected by using a proper catalyst customarily used in this kind of de-silylation reaction, for example, a proper amount of hydrochloric acid, sulfuric acid, perchloric acid and other inorganic acids; formic acid, acetic, acid, propionic acid and other lower alkane acids; benzoic acid, methane sulfonic acid, ethane sulfonic acid, benzene sulfonic acid, 4-methylbenzene sulfonic acid and other organic sulfonic acid; and other organic acids, usually in a solvent. Examples of the solvent include ordinary inert solvents, such as water, methanol, ethanol, isopropanol and other lower alcohols; acetone, methyl ethyl ketone and other ketones; dioxane, tetrahydrofurane, diethyl ether, ethylene glycol dimethyl ether and other ethers; benzene, toluene, xylene, chlorobenzene and aromatic hydrocarbons; acetic acid, propionic acid, and lower alkane acid; and their mixed solvents. The catalyst may be used in the range from an ordinary catalyst amount to excessive amount, preferably an excessive amount. The reaction temperature is usually about 0° to 100° C., preferably from room temperature to about 80° C. and the reaction is terminated in about 3 minutes to 20 hours.

As the elimination reaction of protective group of amino group, for example, the following hydrazine decomposition reaction may be presented. For example, when $R^1$ is a phthalimido-lower alkyl group, by presenting to the hydrazine decomposition for reacting with hydrazine or hydrazine derivative without solvent or in an inert solvent, $R^1$ may be transformed into an amino-lower alkyl group. As the inert solvent used in this reaction, for example, dichloromethane, dichloroethane, chloroform, carbon tetrachloride and halogenated hydrocarbons; methanol, ethanol, and other alcohols may be known. Examples of the hydrazine derivative include methyl hydrazine, ethyl hydrazine, other lower alkyl-substituted hydrazines, phenyl hydrazine and other aryl-substituted hydrazines. The quantity of use of hydrazine or hydrazine derivative to the starting material compound of which $R^1$ corresponds to a phthalimido-lower alkyl group is usually at least equivalent mol, or preferably equivalent mol to 10 times mol. The reaction is conducted usually at 0° to 100° C., preferably 0° to 80° C., and the reaction is generally terminated in about 1 to 40 hours.

The compound of the formula (13) used as starting material in reaction scheme 8 is a known compound disclosed, for example, in J. Gen. Chem., 2.2, 267–269 (1952), and Khim. Geterotsikl. Soedin., 3, 344–345 (1975), among others, and can be easily manufactured according to the method mentioned in these literatures.

The compound of the invention may contain an additional salt of a pharmaceutically permitted acid or base compound. The salt may be easily formed by acting the acid or the base. Examples of the acid used in salt formation include inorganic acids such as hydrochloric acid, sulfuric acid, phosphoric acid, and hydrobromic acid, and, if necessary, organic acids such as oxalic acid, maleic acid, fumaric acid, malic acid, tartaric acid, citric acid, and benzoic acid. The base compound used in the salt formation may include, among others, sodium hydroxide, potassium hydroxide, calcium hydroxide, sodium carbonate, and potassium hydrogencarbonate.

The compound of formula (1) manufactured in the foregoing methods and its salt are easily isolated and refined from the reaction system by ordinary separation means, such as distillation method, recrystallization method, column chromatography, preparative thin layer chromatography, and solvent extraction method.

The extracellular matrix metalloproteinases inhibitor of the invention is used generally in a form of an ordinary pharmaceutical preparation. The pharmaceutical preparation is adjusted by ordinary filler, thickener, binder, humidifier, disintegrating agent, surface active agent, lubricant, and other diluents and vehicles. As the pharmaceutical preparations, various forms can be selected depending on the purpose of treatment, and representative examples include tablets, pills, powders, liquid, suspension, emulsion, granules, capsules, suppositories, injections (liquid, suspension, etc.), and ointment. To form into tablets, carriers are used, for example, lactose, sucrose, sodium chloride, glucose, urea, starch, calcium carbonate, kaolin, crystal cellulose, silicic acid and other vehicles; water, ethanol, propanol, single syrup, glucose liquid, starch liquid, gelatin solution, carboxy methyl cellulose, shellac, methyl cellulose, potassium phosphate, polyvinyl pyrrolidone and other binders; dry starch, sodium alginate, agar powder, laminaran powder, sodium hydrogencarbonate, calcium carbonate, polyoxy ethylene sorbitan fatty acid esters, sodium lauryl sulfate, monoglyceride stearate, starch, lactose and other disintegrating agent; sucrose, stearin, cacao butter, hydrogenated oil and other disintegration suppressors; quaternary ammonium base, sodium lauryl sulfate and other absorption promoters; glycerin, starch and other moisture retainers; starch, lactose, kaolin, bentonite, colloidal silicic acid and other absorbents; refined talc, stearate, boric acid powder, polyethylene glycol and other lubricants. Tablets may be manufactured in ordinary coated tables as required, for example, sugar coated tablet, gelatin coated tablet, enteric coated tablet, film coated tablet, double tablet, or multilayer tablet. When forming into pills, carriers are used, such as glucose, lactose, starch, cacao butter, hardened vegetable oil, kaolin, talc and other vehicles; arabic gum powder, tragacanth powder, gelatin, ethanol and other binder; laminaran, agar and other disintegrating agents. When forming into suppositories, carriers are used, such as polyethylene glycol, cacao butter, higher alcohol, esters of higher alcohol, gelatin, and semisynthetic glyceride. Capsules are manufactured according to the conventional manner, and various carriers listed above and the compound of the invention are blended, and put into hard gelatin capsule, hard capsule, etc. When prepared as injections, liquids, emulsions, and suspensions should be sterilized, and isotonic with the blood. When manufacturing in such forms, diluents are used, such as water, aqueous solution of lactic acid, ethyl alcohol, propylene glycol, ethoxy isostearyl alcohol, and polyoxyethylene sorbitan fatty acid ester. In this case, salt, glucose or glycerin enough for preparing an isotonic solution may be contained in the pharmaceutical preparations, or ordinary dissolution aid, desiccant, soothing agent or the like may be added. As required, further, coloring matter, preservative, perfume, flavor, sweetener, and other medicines may be contained in the pharmaceutical preparations. When manufacturing into paste, cream or gel, diluents are used, for example, white vaseline, paraffin, glycerin, cellulose derivative, polyethylene glycol, silicon, and bentonite.

The quantity of the compound of the invention to be contained in the pharmaceutical preparation of the invention is not particularly defined, but may be selected from a wide range, and it may be usually in a range of 1 to 70% by weight of the pharmaceutical preparation.

The method of administration of the pharmaceutical preparation of the invention is not particularly limited, and determined properly depending on the age, sex and other conditions of the patients, severity of disease, and dosage forms, and usually it is administered systematically or locally, orally or parenterally. For example, tablets, pills, liquid, suspensions, emulsions, granules, and capsules are administered orally, injections are administered intravenously, intramuscularly, intradermally, subcutaneously, or intraperitoneally by mixing with ordinary fluid replacement if necessary. Suppositories are administered intrarectally, and ointments are applied externally.

The dose of the pharmaceutical preparation of the invention may be properly selected depending on the age, body weight, symptom, therapeutic effect, route of administration, treating time and others, and it is usually administered in a range of about 0.1 to 100 mg per 1 kg of body weight, and the daily dose may be administered once daily or in several divided portions. Since the dose varies with various conditions, it may be enough at a smaller dose or a larger dose beyond the specified range may be needed, depending on the individual cases.

EXAMPLES

Manufacturing examples of compounds used in the invention are shown below, being followed the pharmacological study results of these compounds and pharmaceutical examples.

Reference Example 1

(a) Preparation of 2R-bromo-4-methyl-pentanoic acid 50.0 g of D-leucine was dissolved in a mixed solvent of 112 ml of sulfuric acid and 380 ml of water, and 158 g of potassium bromide is added, and the reaction solution was cooled to −2° C. A solution dissolving 343.8 g of sodium nitrite in 100 ml of water was dripped in 1 hour so as to keep the reaction solution at −1° to −2° C., and after dripping, the solution was stirred for 2 hours in an ice bath. Adding 300 ml of chloroform to the reaction solution, insoluble matter was filtered off, an organic layer was separated, and the water layer was extracted five times in 100 ml of chloroform. Combining with the chloroform layer, after drying with magnesium sulfate, the solvent was evaporated in vacuum, and the captioned compound was obtained in a yellow oil form. Yield: 58.5 g.

(b) Preparation of tert-butyl 2R-bromo-4-methyl-pentanoate 58.5 g of 2R-bromo-4-methyl pentanoic acid was dissolved in 150 ml of dichloromethane, this solution was cooled to −40° C., and about 50 ml of isobutene was collected. Keeping at −40° C., 1.5 ml of concentrated sulfuric acid was dripped while stirring, and the tube was sealed and stirred overnight at room temperature. The reaction vessel was cooled again to −40° C. or less, the tube was opened, and let stand at room temperature, and when the reaction solution exceeded 10° C., it was evaporated in vacuum until the reaction solution was consumed to about half. Adding 200 ml of chloroform to the residue, the chloroform layer was washed with aqueous solution of saturated sodium hydrogen carbonate (100 ml×2 times) and 100 ml of brine, and dried over magnesium sulfate and evaporated in vacuum, then the captioned compound was obtained in a yellow oil form. Yield: 67.2 g.

(c) Preparation of benzyl 2-benzyloxycarbonyl-3R-tert-butoxycarbonyl-5-methyl hexanoate 76.2 g of dibenzyl malonate was dissolved in 100 ml of dry dimethyl formamide, and 30.0 g of potassium t-butoxide was added while chilling in ice, and the solution was stirred at room temperature until potassium t-butoxide is dissolved completely. Cooling again in an ice bath, 120 ml of dimethyl formamide of 67.2 g of tert-butyl 2R-bromo-4-methyl-penanoate was dripped in 1 hour, and the solution was stirred for 4 days at 4° C. Pouring the reaction solution into 500 ml of saturated ammonium chloride, and after extracting with ethyl acetate (300 ml×3 times), the organic layer was evaporated in vacuum. Adding 600 ml of diethyl ether to the residue, and after washing in brine (500 ml×2 times), the solution was dried with magnesium sulfate, and the solvent was evaporated in vacuum. The oily residue was purified by column chromatography (silica gel 900 g, hexane/ethyl acetate=20/1 v/v), and the captioned compound was obtained in a colorless oil form. Yield: 71.6 g.

Reference Example 2

Preparation of 3S-(4-benzyloxy-3-benzyloxycarbonyl-2R-isobutylsuccinyl)amino-3,4-dihydrocarbostyril To 4.06 g of benzyl 2-benzyloxycarbonyl-5-methyl-3R-tert-butoxycarbonylhexanoate, 10 ml of trifluoroacetic acid was added, and after letting stand for 1 hour at room temperature, the trifluoroacetic acid was evaporated in vacuum. To the residue, 35 ml of chloroform was added, and it was washed with brine (10 ml×2 times), and dried with magnesium sulfate anhydride, and evaporated in vacuum. The obtained residue was dissolved in 15 ml of dimethyl formamide, 1.45 g of 3S-amino-3,4-dihydrocarbostyril was added, and while cooling in a water bath, 1.21 g of 1-hydroxybenzotriazole and 1.84 g of N,N'-dicyclohexyl carbodiimide were added, and the pH was adjusted to 8 by N-methylmorpholine, and the solution was stirred for 20 hours at room temperature. After filtering off the sediment, the solution was evaporated in vacuum. To the residue, 100 ml of ethyl acetate was added, and the mixture was washed with 1N hydrochloric acid (20 ml×2 times), saturated aqueous solution of sodium hydrogencarbonate (15 ml×3 times), and brine (10 ml), dried with magnesium sulfate anbydride, and evaporated in vacuum. The oily residue was purified by column chromatography (silica gel 90 g, eluted in 33% ethyl acetate/hexane, and then in 40% ethyl acetate/hexane), the captioned compound was obtained in a colorless oily matter. Yield: 3.54 g.

NMR (270 MHz, CDCl$_3$) δ ppm: 8.08 (1H, s), 7.31 (10H, s), 6.96–7.30 (3H, m), 6.74–6.79 (2H, m), 5.03–5.26 (4H, m), 4.52 (1H, dt, J=14.6 Hz), 3.85 (1H, dd, J=16, 10 Hz), 3.36 (1H, dd, J=16.6 Hz), 2.92–3.15 (1H, m), 2.63 (1H, t, J=15 Hz), 1.50–1.80 (2H, m), 0.95–1.15 (1H, m), 0.75–1.00 (6H, m)

Reference Example 3

Preparation of 3S-(3-hydroxycarbonyl-2R-isobutylpropanoyl)-amino-3,4-dihydrocarbostyril 3.50 g of 3S-(4-benzyloxy-3-benzyloxycarbonyl-2R-isobutylsuccinyl)amino-3,4-dihydrocarbostyril was dissolved in 35 ml of methanol, and 35 mg of 10% palladium-carbon was added, and the solution was saturated with hydrogen. After stirring for a day at ordinary pressure, the catalyst was filtered off, and the filtrate was concentrated in vacuo. To this residue, 20 ml of toluene was added, and the mixture was heated for 20 minutes in reflux. The reaction solution was concentrated in vacuo, and 10 ml of ethyl acetate was added to the residue, and the mixture was heated and dissolved, and 2 ml of hexane was added, and after letting stand at room temperature for a day, the precipitating crystals were filtered, and the captioned compound was obtained in a white solid form. Yield: 500 mg.

NMR (270 MHz, DMSO-d$_6$) δ ppm: 8.19 (1H, d, J=8 Hz), 7.15–7.30 (1H, m), 7.16 (2H, t, J=7 Hz), 6.90 (2H, dt, J=8, 7 Hz), 4.46 (1H, dt, J=12, 8 Hz), 2.60–3.00 (3H, m), 2.43 (1H, dd, J=16, 8 Hz), 2.24 (1H, dd, J=16, 6 Hz), 1.05–1.80 (3H, m), 0.88 (6H, dd, J=16, 6 Hz)

Reference Example 4

Preparation of
3S-(4-hydroxy-2R-isobutyl-3-methylenesuccinyl)-
amino-3,4-dihydrocarbostyril 10.8 g of 3S-(4-benzyloxy-3-benzyloxycarbonyl-2R-isobutylsuccinyl)amino-3,4-dihydrocarbostyril was dissolved in 100 ml of methanol, 1.0 g of 10% palladium-carbon was added, and the solution was saturated with hydrogen. After stirring for a day at ordinary pressure, the catalyst was filtered off. To the reaction solution, 2.2 ml of piperidine was added, and after stirring for 15 minutes, 4.9 ml of 37% formaldehyde liquid was added, and the solution was stirred for 7 hours at room temperature, and heated for an hour in reflux. The reaction solution was concentrated in vacuo, dissolved in 200 ml of saturated aqueous solution of potassium carbonate, and washed with chloroform (20 ml×3 times). The water layer was cooled in an ice bath, and the pH was adjusted to 1 by concentrated hydrochloric acid, and after extracting with chloroform (50 ml×2 times), it was washed with brine (20 ml), dried over magnesium sulfate, and evaporated in vacuum, and the captioned compound was obtained in a white solid form. Yield: 1.98 g.

NMR (270 MHz, CDCl$_3$) δ ppm:8.69 (1H, s), 7.19 (2H, dd, J=14, 7 Hz), 7.03 (1H, d, J=7 Hz), 6.82 (1H, d, J=7 Hz), 6.46 (1H, s), 5.89 (1H, s), 4.58 (1H, dt, J=13, 6 Hz), 3.61 (1H, t, J=7 Hz), 3.51 (1H, dt, J=15, 6 Hz), 2.76 (1H, t, J=15 Hz), 1.50–2.00 (3H, m), 0.91 (6H, dd, J=10, 6 Hz)

Reference Example 5

Preparation of
3S-(4-hydroxy-2R-isobutyl-3S-acetylthiomethyl-
succinyl)amino-3,4-dihydroxycarbostyril 840 mg of 3S-(4-hydroxy-2R-isobutyl-3S-methylenesuccinyl)amino-3,4-dihydrocarbostyril was dissolved in 8 ml of thioacetic acid, and stirred for 4 days in a dark place at 30° C. Diethyl ether was added to the reaction solution, and the precipitating crystals were filtered, and the captioned compound was obtained in a white solid form. Yield: 330 mg.

NMR (270 MHz, CDCl$_3$) δ ppm:8.70 (1H, brs), 6.80–7.30 (4H, m), 4.45–4.60 (1H, m), 3.59 (1H, dd, J=15.6 Hz), 2.80–3.40 (4H, m), 2.68 (1H, t, J=15 Hz), 2.36 (3H, s), 1.10–1.80 (3H, m), 0.95 (6H, dd, J=13, 7 Hz)

Reference Example 6

(a) Preparation of D-leucic acid

While heating and stirring 100 ml of aqueous solution of 14 g of sodium nitrite at 90° C., 400 ml aqueous solution of 0.5N sulfuric acid of 25 g of D-leucine was added over 45 minutes. After dripping, the solution was stirred for 15 minutes until foams were no longer generated. The reaction solution was concentrated to 200 ml in vacuo, and the obtained residue was extracted with diethyl ether. The diethyl ether layer was washed one with 1N hydrochloric acid, and twice with saturated brine sequentially, and dried over sodium sulfate anhydride, and concentrated in vacuo. The obtained oily residue was left over, crystallized, and the captioned compound was obtained. Yield: 14.50 g.

(b) Preparation of D-leucic acid benzyl ester

To 150 ml of tetrahydrofurane of 14.50 of D-leucic acid, 15.2 g of triethylamine and then 14.4 ml of benzyl bromide are added, and the solution was stirred for 3 hours while refluxing. The insoluble matter produced from the reaction solution was filtered off, and the filtrate was concentrated in vacuo. The obtained residue was dissolved and extracted in 150 ml of ethyl acetate. The ethyl acetate layer was washed twice with saturated bicarbonate water, twice with 1N hydrochloric acid, and twice with saturated brine sequentially, and dried over sodium sulfate anhydride, and concentrated in vacuo. The obtained oily residue was dried, and the captioned compound was obtained. Yield: 18.34 g.

(c) Preparation of 1,2-dibenzyl-1-t-butyl-4-methyl-1,1,2(R)-pentane-tricarboxylate To 140 ml of N,N-dimethyl formamide solution of 20.65 g of benzyl t-butylmalonate, 3.30 g of sodium hydride (content 60%) was added, and the solution was stirred for 1 hour at room temperature. On the other hand, to 100 ml solution of dichloromethane of 18.34 g of D-leucic acid benzyl ester, 6.66 ml of pyridine was added, and stirred in ice, and 100 ml of dichloromethane of 13.53 ml of anhydrous trifluoromethane sulfonic acid was dripped thereon in 30 minutes. After dripping, the solution was further stirred for 1 hour in ice. The reaction solution was washed once with water, and one with saturated brine sequentially, and dried with sodium sulfate anhydride. Filtering off the sodium sulfate anhydride, the filtrate was dripped in 30 minutes on the N,N-dimethyl formamide solution above prepared while stirring in ice. After dripping, the solution was stirred overnight at room temperature. The reaction solution was concentrated in vacuo, and dripped in 30 minutes. After dripping, the solution was stirred overnight at room temperature. The reaction solution was concentrated in vacuo, and the obtained residue was extracted in 300 ml of ethyl acetate. The ethyl acetate layer was washed twice with saturated aqueous solution of sodium hydrogencarbonate, twice with 1N hydrochloric acid, and twice with saturated brine sequentially, and dried with sodium sulfate anhydride, and concentrated in vacuo. The obtained oily residue was purified by the silica gel column chromatography, and eluted in ethyl acetate/petroleum ether (1:20), and the captioned compound was obtained in an oily matter. Yield: 19.0 g.

Reference Example 7

Preparation of
1,2-dibenzyl-1-tert-butyl-1-phthalimidomethyl-4-
methyl-1,1,2(R)-pentane-tricarboxylate In a 50 ml solution of dimethyl formamide of 6.00 g of 1,2-dibenzyl-1-tert-butyl-4-methyl-1,1,2(R)-pentanetricarboxylate, 653 g (60% content) of sodium hydride was added while stirring in ice, and stirred for 30 minutes. The reaction solution was returned to room temperature, and 4.04 g of N-bromomethylphthalimide was added, and stirred for 3 days at room temperature. After neutralizing the reaction solution by adding a small amount of acetic acid, it was concentrated in vacuo. The obtained oily residue was extracted in 100 ml of ethyl acetate, and the ethyl acetate layer was washed once with water and twice with saturated brine, and dried with sodium sulfate anhydride, and concentrated in vacuo. The obtained oily residue was purified by silica gel column chromatography, and eluted in chloroform, and the captioned compound was obtained in an oily form. Yield: 4.00 g.

Reference Example 8

Preparation of 4-tert-butoxy-2R-isobutyl-3-(R or S)-phthalimidomethylsuccinic acid To a 30 ml solution of methanol of 4.00 g of 1,2-dibenzyl-1-tert-butyl-1-phthalimidomethyl-4-methyl-1,1,2(R)-pentane-tricarboxylate, 200 mg of 10% palladium-carbon was added, and hydrogen gas was introduced in vacuo, and the solution was stirred for 2 days. From the reaction solution, the catalyst was filtered off by using celite, and the filtrate was concentrated in vacuo. The obtained residue was dissolved in 30 ml of toluene, and 0.70 ml of N-methylmorpholine was added, and the solution was stirred for 7 hours while refluxing. To the reaction solution, 70 ml of toluene was added, and the organic layer was washed twice with 1N hydrochloric acid, and three times with saturated brine, and dried with sodium sulfate anhydride, and concentrated in vacuo. The obtained oily residue was purified by the silica gel column chromatography, and eluted in 2% methanol/chloroform, and the captioned compound was obtained in a oily form. Yield: 1.00 g.

Reference Example 9

Preparation of 3S-(4-tert-butoxy-2R-isobutyl-3(R or S)-phthalimidomethylsuccinyl)amino-3,4-dihydrocarbostyril To a 10 ml suspension of dimethyl formamide of 500 mg of 4-tert-butoxy-2R-isobutyl-3(R or S)-phthalimidomethyl-succinic acid, 190 mg of 1-hydroxybenzotriazole, and 228 mg of 3S-amino-3,4-dihydroxycarbostyril, 290 g of N,N'-dicyclohexyl carbodiimide was added while stirring in ice, and was stirred for 2 hours in ice and 18 hours at room temperature. The reaction solution was concentrated in vacuo, and 60 ml of ethyl acetate was added to the residue, and the insoluble matter was filtered off. The ethyl acetate layer of the filtrate was sequentially washed with saturated aqueous solution of sodium hydrogencarbonate (2 times), 1N hydrochloric acid (2 times), and saturated brine (2 times), and dried with sodium sulfate anhydride, and concentrated in vacuo. The obtained oily residue was purified by silica gel column chromatography, and eluted in 0.5% methanol/chloroform, and the captioned compound was obtained in a powder form. Yield: 390 mg.

NMR (270 MHz, CDCl$_3$) δ ppm: 8.52 (1H, s), 7.87–7.79 (2H, m), 7.75–7.69 (2H, m), 7.53 (1H, d, J=5 Hz), 7.24–7.19 (2H, m), 7.02 (1H, t, J=7 Hz), 6.89 (1H, d, J=8 Hz), 4.66–4.58 (1H, m), 4.19 (1H, dd, J$_1$=9 Hz, J$_2$=14 Hz), 3.80 (1H, dd, J$_1$=5 Hz, J$_2$=14 Hz) 3.63 (1H, dd J$_1$=6 Hz, J$_2$=15 Hz), 3.50–3.47 (1H, m), 2.98–2.80 (2H, m), 1.73–1.58 (3H, m), 0.92 (6H, dd, J$_1$=7 Hz, J$_2$=14 Hz)

Reference Example 10

Preparation of 3,4-methylenedioxybenzylidenesuccinic acid

Dissolving 19.14 g of metal sodium in 400 ml of ethanol, 110.8 ml of diethyl succinate and 100 g of piperonal were added, and the solution was heated and refluxed for 3 hours. The reaction solution was concentrated in vacuo, and the residue was dissolved in 700 ml of water, and washed with 300 ml of diethyl ether. The water layer was stirred in ice, adjusted to pH 1 by concentrated hydrochloric acid, and extracted with 300 ml of diethyl ether. The diethyl ether layer was washed once with saturated brine, and dried over magnesium sulfate anhydride, and concentrated in vacuo. The obtained oily residue was dissolved by 181.4 g in 350 ml of ethanol, and 400 ml of 5N sodium hydroxide was added to stir overnight at room temperature. The reaction solution was concentrated in vacuo, and the residue was washed with 200 ml of diethyl ether. The water layer was stirred in ice, adjusted to pH 1 by concentrated hydrochloric acid, and extracted with 400 ml of ethyl acetate. The ethyl acetate layer was washed with saturated brine, dried over magnesium sulfate anhydride, and concentrated in vacuo. To the obtained residue, 300 ml of diethyl ether was added to solidify, and the captioned compound was obtained. Yield: 67.34 g.

Reference Example 11

Preparation of 4-ethoxy-2-(3,4-methylenedioxybenzylidene)succinic acid

To 23.5 g of 3,4-methylenedioxybenzylidenesuccinic acid, 200 ml of acetic anhydride was added, and heated in reflux for 2 hours. The reaction solution was concentrated in vacuo, and 200 ml of ethanol was added to the residue, and the mixture was heated in reflux overnight. The reaction solution was concentrated in vacuo, and the residue was extracted with 300 ml of ethyl acetate. The ethyl acetate layer was washed twice with saturated brine, and dried over magnesium sulfate anhydride, and concentrated in vacuo. To the obtained crystalline residue, diethyl ether was added to wash, and the captioned compound was obtained. Yield: 17.76 g.

Reference Example 12

Preparation of 4-ethoxy-2-piperonylsuccinic acid

To a 100 ml solution of ethanol of 9.70 g of 4-ethoxy-2-(3,4-methylenedioxybenzylidene) succinic acid, 970 mg of 10% palladium-carbon was added, and catalytic hydrogenation was carried out overnight at room temperature. The catalyst was filtered off from the reaction solution by using celite, and the filtrate was concentrated in vacuo. The obtained oily residue was dried, and the captioned compound was obtained. Yield: 10.36 g.

Reference Example 13

Preparation of 3-(4-ethoxy-2-piperonylsuccinyl)-amino-3,4-dihydrocarbostyril

To a 3 ml solution of dimethyl formamide of 260 mg of 3-amino-3,4-dihydrocarbostyril, a 5 ml solution of dichloromethane of 500 mg of 4-ethoxy-piperonylsuccinic acid and 240 mg of 1-hydroxybenzotriazole were added, and while stirring in ice, 360 mg of N,N'-dicyclohexylcarbodi-imide was added, and the mixture was stirred for 2 hours in ice and for 3 days at room temperature. Insoluble matter was filtered off from the reaction solution, and the filtrate was concentrated in vacuo. To the obtained filtrate, 30 ml of chloroform was added to extract, and the chloroform layer was washed sequentially with saturated aqueous solution of sodium hydrogencarbonate, 1N hydrochloric acid, and saturated brine, and dried over magnesium sulfate anhydride and concentrated in vacuo. The obtained residue was purified by silica gel column chromatography, and eluted in ethyl acetate/hexane (1:1), and the captioned compound was obtained. Yield: 100 mg.

Reference Example 14

Preparation of 4-t-butoxy-3-methylene-2R-isobutylsuccinate

To a 200 ml solution of isopropanol of 40.0 g of 1,2-dibenzyl-1-t-butyl-4-methyl-1,1,2(R)-pentane-tricarboxylate, 3.50 g of 10% palladium-carbon was added, and hydrogen gas was introduced in vacuo to stir overnight at room temperature. The catalyst was filtered off from the reaction solution by using celite. To the obtained filtrate, 23.72 ml of piperidine and 108.2 ml of 37% aqueous solution of formaldehyde were added, and the mixture was stirred for 2 days at room temperature. The reaction solution was concentrated in vacuo, and the obtained residue was dissolved in 350 ml of ethyl acetate and extracted. The ethyl acetate layer was washed sequentially with 1N hydrochloric acid (300 ml×1 time and 200 ml×1 time) and twice with saturated brine, and dried over sodium sulfate anhydride, and concentrated in vacuo. The obtained oily residue was purified by silica gel column chromatography (eluted in 2% methanol/chloroform), and the captioned compound was obtained in an oily form. Yield: 13.81 g.

NMR (270 MHz, CDCl$_3$) δ ppm: 11.00 (1H, bs), 6.29 (1H, s), 5.67 (1H, s), 3.55 (1H, t, J=8 Hz), 1.76 (1H, dd, J$_1$=6 Hz, J$_2$=14 Hz), 1.63–1.49 (2H, m), 1.49 (9H, s), 0.92 (6H, dd, J$_1$=6 Hz, J$_2$=9 Hz)

Reference Example 15

Preparation of 4-t-butoxy-2R-isobutyl-3S-methylsuccinate

To a 100 ml solution of ethyl acetate of 13.81 g of 4-t-butoxy-3-methylene-2R-isobutylsuccinate, 970 mg of 10% palladium-carbon was added, and hydrogen gas was introduced in vacuo to stir overnight at room temperature. The catalyst was filtered off from the reaction solution by using celite, and 11.35 ml of dicyclohexylamine was added while stirring in ice. Immediately, a white sediment was formed, and was filtered, and washed with a small amount of diethyl ether. The obtained white sediment was recrystallized from 150 ml of ethyl acetate, and 13.50 g of while solid matter was obtained.

The obtained compound (8.20 g) was suspended in 200 ml of ethyl acetate, and the ethyl acetate layer was washed sequentially with 0.5M sulfuric acid (100 ml×2 times) and saturated brine (100 ml×3 times), and dried over magnesium sulfate anhydride, and concentrated in vacuo. The obtained residue was dried, and the captioned compound was obtained in an oily form. Yield: 4.60 g.

NMR (270 MHz, CDCl$_3$) δ ppm: 10.00 (1H, bs), 2.73–2.68 (1H, m), 2.61–2.55 (1H, m), 1.72–1.63 (2H, m), 1.45 (9H, s), 1.29–1.19 (1H, m), 1.17 (3H, d, J=7 Hz), 0.91 (6H, dd, J$_1$=2 Hz, J$_2$=7 Hz)

Reference Example 16

Preparation of 3S-t-butoxycarbonylamino-3,4-dihydrocarbostyril 10 g of 3S-amino-3,4-dihydrocarbostyril was dissolved in 100 ml of N,N-dimethylformamide, and, after ice-cooling, 14.8 g of t-butoxycarboxylic anhydride was added, and the pH was adjusted to 8 by triethylamine. After stirring for i hour at 0° C., returning to room temperature, the pH was adjusted again to 8 by triethylamine, and the solution was stirred for 1 hour. The reaction solution was concentrated in vacuo, and 300 ml of ethyl acetate was added to the residue, and the mixture was washed sequentially with 1N hydrochloric acid (100 ml×2 times), aqueous solution of saturated sodium hydrogencarbonate (100 ml×2 times), and saturated brine (100 ml), and dried over magnesium sulfate anhydride, and evaporated in vacuum. The oily residue was purified by column chromatography (silica gel 200 g, eluted in 33% ethyl acetate/hexane), and the obtained oily matter was dried in vacuum, and crystallized, and the captioned compound was obtained. Yield: 14.38 g.

NMR (270 MHz, CDCl$_3$) δ ppm: 8.20 (1H, brs), 7.18–7.26 (2H, m), 7.02 (1H, dt, J=1.7 Hz), 6.80 (1H, d, J=8 Hz), 5.62 (1H, brs), 4.36 (1H, dt, J=15, 6 Hz), 3.49 (1H, dd, J=15.6 Hz), 2.85 (1H, t, J=15 Hz), 1.53 (9H, s)

Reference Example 17

Preparation of 3S-benzyloxycarbonylamino-3,4-dihydrocarbostyril 10 g of 3S-amino-3,4-dihydrocarbostyril was suspended in 100 ml of N,N-dimethylformamide, and 17.6 ml of benzyloxycarbonyl chloride was dripped while stirring in ice, and the pH was adjusted to 8 by triethylamine. After stirring for 1 hour at 0° C., returning to room temperature, the pH was adjusted again to 8 by triethylamine, and the solution was stirred for 1 hour. The reaction solution was concentrated in vacuo, and 300 ml of ethyl acetate was added to the residue, and the insoluble matter was filtered off, and the filtrate was sequentially washed with 1N hydrochloric acid (100 ml×2 times), aqueous solution of saturated sodium hydrogencarbonate (100 ml×2 times), and saturated brine (100 ml), and dried over magnesium sulfate anhydride. The organic layer was evaporated in vacuum, and 5 ml of ethyl acetate was added to the obtained oily residue, and further 50 ml of hexane was added, and the precipitating crystals were filtered, and the captioned compound was obtained. Yield: 7.5 g.

NMR (270 MHz, CDCl$_3$) δ ppm: 8.16 (1H, brs), 7.30–7.40 (5H, m), 7.18–7.24 (2H, m), 7.03 (1H, dt, J=1.7 Hz), 6.80 (1H, dd, J=1, 8 Hz), 5.88 (1H, brs), 5.16 (2H, s), 4.42 (1H, dt, J=15, 6 Hz), 3.52 (1H, dd, J=15, 6 Hz), 2.87 (1H, t, J=15 Hz)

Reference Example 18

Preparation of 3S-t-butoxycarbonylamino-7-chloro-3,4-dihydrocarbostyril

Using a corresponding starting material, the captioned compound was obtained in the same manner as in Reference Example 16.

NMR (270 MHz, CDCl$_3$) δ ppm: 8.04 (1H, bs), 7.13 (1H, d, J=8 Hz) 7.00 (1H, dd, J$_1$=2 Hz, J$_2$=8 Hz), 6.81 (1H, d, J=2 Hz), 5.56 (1H, bs), 4.38–4.29 (1H, m), 3.48 (1H, dd, J$_1$=6 Hz, J$_2$=15 Hz), 2.80 (1H, t, J=15 Hz), 1.48 (9H, s)

Reference Example 19

Preparation of 3S-t-butoxycarbonylamino-7-chloro-1-hydroxy-3,4-dihydrocarbostyril To a 30 ml solution of dimethyl formamide of 4.00 g of 3S-amino-7-chloro-1-hydroxy-3,4-dihydrocarbostyril hydrochloride, while stirring in ice, 1.64 ml of N-methylmorpholine was added, and a 10 ml solution of dimethyl formamide of 3.90 g of di-t-butyldicarbonate was added and stirred for 2 hours at room temperature. The reaction solution was concentrated in vacuo, and 50 ml of water was added to the residue to solidify and filter. The crude product was washed with diethyl ether, and the captioned compound was obtained. Yield: 1.84 g.

NMR (270 MHz, DMSO-$d_6$) δ ppm: 10.63 (1H, s), 7.27 (1H, d, J=8 Hz), 7.25 (1H, d, J=9 Hz), 7.16 (1H, d, J=2 Hz), 7.06 (1H, dd, $J_1$=2 Hz, $J_2$=8 Hz), 4.28–4.24 (1H, m), 3.00 (1H, s), 2.97 (1H, d, J=4 Hz), 1.41 (9H, s)

Reference Example 20

Preparation of
3S-t-butoxycarbonylamino-1-hydroxy-3,4-dihydrocarbostyril

Using a corresponding starting material, the captioned compound was obtained in the same manner as in Reference Example 19.

NMR (270 MHz, CDCl$_3$) δ ppm: 8.85 (1H, bs), 7.20 (2H, t, J=8 Hz), 7.01 (1H, dt, $J_1$=1 Hz, $J_2$=8 Hz), 6.85 (1H, d, J=8 Hz), 5.66 (1H, d, J=5 Hz), 4.39–4.31 (1H, m), 3.48 (1H, dd, $J_1$=6 Hz, $J_2$=15 Hz), 2.85 (1H, t, J=15 Hz), 1.49 (9H, s)

Reference Example 21

Preparation of
3S-t-butoxycaronylamino-1-hexyloxy-3,4-dihydrocarbostyril

To a 5 ml solution of dimethyl formamide of 700 mg of 3S-t-butoxycarbonylamino-1-hydroxy-3,4-dihydrocarbostyril, 110 mg of sodium hydride (60% content) was added while stirring in ice-cooling, and 15 minutes later, 641 mg of iodo hexane was added, and the solution was stirred for 2 hours at room temperature. The reaction solution was concentrated in vacuo, and the obtained residue was extracted with 30 ml of ethyl acetate. The ethyl acetate layer was washed sequentially twice with 1N hydrochloric acid and twice with saturated brine, and dried with magnesium sulfate anhydride, and concentrated in vacuo. The obtained oily residue was purified by silica gel column chromatography, and eluted in chloroform, and the captioned compound was obtained. Yield: 630 mg.

NMR (270 MHz, CDCl$_3$) δ ppm: 7.30 (1H, t, J=8 Hz), 7.21 (2H, d, J=9 Hz), 7.07 (1H, td, $J_1$=1 Hz, $J_2$=7 Hz), 5.60 (1H, bs), 4.37–4.32 (1H, m), 4.12 (1H, q, J=7 Hz), 4.02 (1H, q, J=7 Hz), 3.43 (1H, dd, $J_1$=5 Hz, $J_2$=15 Hz), 2.80 (1H, t, J=15 Hz), 1.82–1.70 (2H, m), 1.48 (9H, s), 1.54–1.30 (6H, m), 0.90 (3H, t, J=7 Hz)

Reference Example 22

Preparation of
3S-(4-t-butoxy-2R-isobutyl-3S-methylsuccinyl)amino-1-hexyloxy-3,4-dihydrocarbostyril To 630 mg of 3S-t-butoxycarbonylamino-1-hexyloxy-3,4-dihydrocarbostyril, 5 ml of trifluoroacetic acid was added to dissolve, and the solution was let stand at room temperature for 30 minutes. The reaction solution was concentrated in vacuo, and the obtained residue was dissolved in 10 ml of tetrahydrofurane. To this solution, while stirring in ice-cooling, triethylamine was added to neutralize, and a 10 ml solution of tetrahydrofurane of 247 mg of 1-hydroxybenzotriazole and 446 mg of 4-t-butoxy-2R-isobutyl-3S-methylsuccinate was added, and 130 μl of triethylamine and 377 mg of dicyclohexylcarbodiimide were added, and the mixture was stirred for 2 hours in ice-cooling and overnight at room temperature. The formed insoluble matter was filterated off from the reaction solution, and the filtrate was concentrated in vacuo. The obtained oily residue was dissolved and extracted with 50 ml of ethyl acetate. The ethyl acetate layer was washed sequentially twice with saturated aqueous solution of sodium hydrogencarbonate, twice with 1N hydrochloric acid, and twice with saturated brine, and dried over magnesium sulfate anhydride, and concentrated in vacuo. The obtained oily residue was purified by the silica gel column chromatography, and eluted in chloroform, and the captioned compound was obtained. Yield: 740 mg.

NMR (270 MHz, CDCl$_3$) δ ppm: 7.30 (1H, t, J=8Hz), 7.21 (2H, d, J=9 Hz), 7.07 (1H, dt, $J_1$=1Hz, $J_2$=8 Hz), 6.70 (1H, d, J=5 Hz), 4.63–4.50 (1H, m), 4.13 (1H, q, J=8 Hz), 4.02 (1H, q, J=8 Hz), 3.51 (1H, dd, $J_1$=6 Hz, $J_2$=15 Hz), 2.73 (1H, t, J=15 Hz), 2.56–2.53 (2H, m), 1.81–1.69 (4H, m), 1.52–1.30 (6H, m), 1.46 (9H, s) 1.18–1.09 (4H, m), 0.95–0.86 (9H, m)

Reference Example 23

Preparation of
3S-(4-benzyloxyamino-2R-isobutyl-3S-methylsuccinyl)amino-1-hexyloxy-3,4-dihydrocarbostyril To 740 mg of 3S-(4-t-butoxy-2R-isobutyl-3S-methylsuccinyl)amino-1-hexyloxy-3,4-dihydrocarbostyril, 5 ml of trifluoroacetic acid was added to dissolve, and the solution was let stand at room temperature for 90 minutes. The reaction solution was concentrated in vacuo, and the obtained oily residue was dissolved in 50 ml of ethyl acetate to extract. The ethyl acetate layer was washed three times with saturated brine, and dried over magnesium sulfate anhydride, and concentrated in vacuo. The obtained oily residue was dried, and dissolved in 10 ml of dimethyl formamide, and while stirring in ice-cooling, a 5 ml dimethyl formamide solution of 306 mg of 1-hydroxybenzotriazole and 362 mg of benzyloxyamine hydrochloride with 231 μl of N-methyl morpholine was added, and further 120 μl of N-methyl morpholine and 434 mg of 1-ethyl-3-(3-dimethylaminopropyl)carbodiimide hydrochloride were added, and the mixture was stirred for 2 hours in ice-cooling and overnight at room temperature. The reaction solution was concentrated in vacuo, and 50 ml of ethyl acetate was added to the obtained oily residue to extract. The ethyl acetate layer was washed sequentially twice with saturated aqueous solution of sodium hydrogencarbonate, twice with 1N hydrochloric acid, and twice with saturated brine, and dried over magnesium sulfate anhydride, and concentrated in vacuo. Adding diethyl ether to the obtained crystalline residue, it was filtered and dried, and the captioned compound was obtained. Yield: 430 mg.

NMR (270 MHz, DMSO-$d_6$) δ ppm: 11.10 (1H, s), 8.57 (1H, d, J=8 Hz), 7.40–7.35 (6H, m), 7.30 (1H, t, J=8 Hz), 7.14 (1H, d, J=7 Hz), 7.06 (1H, t, J=7 Hz), 4.79 (2H, s), 4.63–4.54 (1H, m), 4.01–3.95 (2H, m), 3.05 (1H, t, J=13 Hz), 2.93 (1H, dd, $J_1$=7 Hz, $J_2$=15 Hz), 2.52–2.49 (1H, m), 2.17–2.13 (1H, m), 1.71–1.29 (10H, m), 0.97 (3H, d, J=7 Hz), 0.90–0.79 (10H, m)

Reference Example 24

Preparation of
3S-t-butoxycarbonylamino-1-(4-cyanobenzyl)-3,4-dihydrocarbostyril To a 5 ml solution of dimethyl formamide of 600 mg of 3S-t-butoxycarbonylamino-3,4-dihydrocarbostyril, while stirring in ice-cooling, 96 mg of sodium hydride (60% content) was added, and 150 minutes later, 494 mg of α-bromo-p-tolunitrile was added, and the mixture was stirred for 2 hours at room temperature. To the reaction solution, 30 ml of ethyl acetate was added to extract. The ethyl acetate layer was washed once with 1N hydrochloric acid, and three times with saturated brine, and dried over magnesium sulfate anhydride, and concentrated in vacuo. The obtained oily residue was purified by silica gel column chromatography (eluted in chloroform), and the captioned compound was obtained. Yield: 760 mg.

NMR (270 MHz, CDCl$_3$) δ ppm: 7.62 (2H, d, J=8 Hz), 7.32 (2H, d, J=9 Hz), 7.25 (1H, d, J=8 Hz), 7.17 (1H, t, J=8 Hz), 7.05 (1H, td, J$_1$=1 Hz, J$_2$=7 Hz), 6.77 (1H, dd, J$_1$=1 Hz, J$_2$=8 Hz), 5.71 (1H, bs), 5.46 (1H, d, J=17 Hz), 4.97 (1H, d, J=16 Hz), 4.50–4.40 (1H, m), 3.48 (1H, dd J$_1$=6 Hz, J$_2$=15 Hz), 2.88 (1H, t, J=15 Hz), 1.48 (9H, s)

Reference Example 25

Preparation of
3S-t-butoxycarbonylamino-1-(5-chloro-2-thienylmethyl)-3,4-dihydrocarbostyril Using 5-chloro-2-chloromethylthiophene and a corresponding starting material, the captioned compound was obtained in the same manner as in Reference Example 24.

NMR (270 MHz, CDCl$_3$) δ ppm: 7.28–7.20 (2H, m), 7.11–7.02 (2H, m), 6.79 (1H, d, J=4 Hz), 6.72 (1H, d, J=4 Hz), 5.75 (1H, bs), 5.32 (1H, d, J=16 Hz), 5.03 (1H, d, J=16 Hz), 4.34–4.29 (1H, m), 3.43 (1H, dd, J$_1$=5 Hz, J$_2$=15 Hz), 2.80 (1H, t, J=15 Hz), 1.48 (9H, s)

Reference Example 26

Preparation of
1-benzyloxy-3S-t-butoxycarbonylamino-3,4-dihydrocarbostyril

Using benzyl bromide and a corresponding starting material, the captioned compound was obtained in the same manner as in Reference Example 24.

NMR (270 MHz, CDCl$_3$) δ ppm: 7.52–7.47 (2H, m), 7.40–7.35 (3H, m), 7.31–7.18 (3H, m), 7.06 (1H, td, J$_1$=2 Hz, J$_2$=7 Hz), 5.59 (1H, bs), 5.13 (1H, d, J=10 Hz), 5.03 (1H, d, J=9 Hz), 4.40–4.35 (1H, m), 3.42 (1H, dd, J$_1$=6 Hz, J$_2$=15 Hz), 2.78 (1H, t, J=15 Hz), 1.48 (9H, s)

Reference Example 27

Preparation of
3S-t-butoxycarbonylamino-7-chloro-1-ethoxy-3,4-dihydrocarbostyril Using iodoethane and a corresponding starting material, the captioned compound was obtained in the same manner as in Reference Example 21.

NMR (270 MHz, CDCl$_3$) δ ppm: 7.21 (1H, d, J=2Hz), 7.13 (1H, d, J=8 Hz), 7.04 (1H, dd, J$_1$=2Hz, J$_2$=8 Hz), 5.56 (1H, bs), 4.35–4.29 (1H, m), 4.18 (2H, qd, J$_1$=7 Hz, J$_2$=16 Hz), 3.42 (1H, dd, J$_1$=5 Hz, J$_2$=15 Hz), 2.76 (1H, t, J=15 Hz), 1.47 (9H, s), 1.40 (3H, t, J=7 Hz)

Reference Example 28

Preparation of
3S-amino-1-isobutoxy-3,4-dihydrocarbostyril

Using isobutoxy amine, the captioned compound was obtained according to the method described in J. Org. Chem. 1989, 54, 3394.

NMR (270 MHz, CDCl$_3$) δ ppm: 7.15–7.35 (3H, m), 7.05 (1H, t, J=7 Hz), 3.93 (1H, t, J=7 Hz), 3.78 (1H, t, J=7 Hz), 3.62 (1H, dd, J=13.6 Hz), 3.10 (1H, dd, J=15.6 Hz), 2.83 (1H, t, J=15 Hz), 2.05–2.25 (1H, m), 1.08 (3H, d, J=5 Hz), 1.05 (3H, d, J=5 Hz)

Reference Example 29

Preparation of 3S -t-butoxycarbonylamino-1-ethoxy-3,4-dihydrocarbostyril

Using iodoethane and a corresponding starting material, the captioned compound was obtained in the same manner as in Reference Example 21.

NMR (270 MHz, CDCl$_3$) δ ppm: 7.20–7.23 (3H, m), 7.07 (1H, dt, J=1, 7 Hz), 5.59 (1H, brs), 4.34 (1H, dt, J=14.6 Hz), 4.16 (1H, q, J=7 Hz), 4.13 (1H, q, J=7 Hz), 3.42 (1H, dd, J=6, 14Hz), 2.81 (1H, t, J=14 Hz), 1.48 (9H, s), 1.39 (3H, t, J=7 Hz)

Reference Example 30

Preparation of 3S -benzyloxycarbonylamino-1-ethoxymethyl-3,4-dihydrocarbostyril

Using ethoxymethyl chloride and a corresponding starting material, the captioned compound was obtained in the same manner as in Reference Example 24.

NMR (270 MHz, CDCl$_3$) δ ppm: 7.39–7.28 (7H, m), 7.21 (1H, d, J=7 Hz), 7.09 (1H, td, J$_1$=1 Hz, J$_2$=7 Hz), 5.95 (1H, bs), 5.78 (1H, d, J=11 Hz), 5.15 (2H, s), 4.95 (1H, d, J=11 Hz), 4.42–4.37 (1H, m), 3.61 (2H, qd, J$_1$=7 Hz, J$_2$=3 Hz), 3.46 (1H, dd, J$_1$=5 Hz, J$_2$=14 Hz), 2.82 (1H, t, J=15 Hz), 1.21 (3H, t, J=7 Hz)

Reference Example 31

Preparation of
3S-benzyloxycarbonylamino-1-hexyloxymethyl-3,4-dihydrocarbostyril Using a starting material corresponding to hexyloxymethyl chloride, the captioned compound was obtained in the same manner as in Reference Example 24.

NMR (270 MHz, CDCl$_3$) δ ppm: 7.39–7.28 (7H, m), 7.21 (1H, d, J=7 Hz), 7.09 (1H , td, J$_1$=1 Hz, J$_2$=7 Hz), 5.96 (1H, bs), 5.77 (1H, d, J=11 Hz), 5.15 (2H, s), 4.95 (1H, d, J=11 Hz), 4.42–4.37 (1H, m), 3.57–3.42 (3H, m), 2.82 (1H, t, J=15 Hz), 1.58–1.51 (2H, m), 1.33–1.21 (6H, m), 0.85 (3H, t, J=7 Hz)

Reference Example 32

Preparation of
3S-benzyloxycarbonylamino-1-methoxymethyl-3,4-dihydrocarbostyril

Using methoxymethyl chloride and a corresponding starting material, the captioned compound was obtained in the same manner as in Reference Example 24.

NMR (270MHz, CDCl$_3$) δ ppm: 7.15–7. 50 (8 H, m), 7.09 (1H, t, J=7 Hz), 5.95 (1 H, brs), 5.70 (1H, d, J=10 Hz), 5.15 (2H, s), 4.95 ([H, d, J=10 Hz), 4.41 (1H, dt, J=14, 5Hz), 3.46 (1H, dd, J=14, 5Hz), 3.39 (3H, s), 2.83 (1H, t, J=14 Hz)

Reference Example 33

Preparation of 1-banzyl-3S-t-butoxycarbonylamino-3,4dihydrocarbostyril

Using benzyl bromide and a corresponding starting material, the captioned compound was obtained in the same manner as in Reference Example 24.
NMR (270 MHz, CDCl$_3$) δppm: 7.36-7.12 (7 H, m), 7.0 1 (1H, td, J$_1$=7 Hz, J$_2$=1 Hz), 6.90 (1H, d, J=8 Hz), 5.81 (1H, bs), 5.44 (1H, d, J=16 H z), 4.91 (1H, d, J=16 Hz), 4.44-4.39 (1 H, m), 3.48 (1H, dd, J$_1$=6Hz, J$_2$=15Hz), 2.86 (1H, t, J=15 Hz), 1.48 (9H, s)

Reference Example 34

Preparation of 3S-t-butoxycarbonylamino-1-(4-methoxycarbonylbenzyl)-3,4-dihydrocarbostyril Using 4-methoxycarbonylbenzyl bromide and a corresponding starting material, the captioned compound was obtained in the same manner as in Reference Example 24.
NMR (270 MHz, CDCl$_3$) δppm: 7.9 9 (2 H, d, J=8 Hz), 7.2 7 (2 H, d, J=7 Hz), 7.2 3 (1 H, d, J=7 Hz), 7.14 (1H t J=7 Hz) 7.02 (1H, td, J$_1$=1 Hz, J$_2$=8 Hz), 6.82 (1H, d, J=8 Hz), 5.77 (1H, bs), 5.48 (1H, d, J=17 Hz), 4.97 (1H, d, J=17 Hz), 4.48-4.39 (1H, m), 3.90 (3H, s), 3.49 (1H, dd, J$_1$=5 Hz J$_2$=14 Hz), 2.88 (1H, t, J=1.5 Hz), dd, J$_1$=5 Hz, J$_2$=14 Hz), 2.88 (1H, t, J=15 Hz), 1.49 (9H, s)

Reference Example 35

Preparation of 3S-t-butoxycarbonylamino-1-(4-methoxybenzyl)-3,4-dihydrocarbostyril Using 4-methoxybenzyl chloride and a corresponding starting material, the captioned compound was obtained in the same manner as in Reference Example 24.
NMR (270 MHz, CDCl$_3$) δppm: 7.28-7.13 (4H, m), 7.03-6.91 (2H, m), 6.84 (2H, d, J=9 Hz), 5.81 (1H, bs), 5.34 (1H, d, J=16 Hz), 4.88 (1 H, d, J=16 Hz), 4.41-4.36 (1 H, m), 3.77 (3H, s), 3.46 (1H, dd, J$_1$=7 Hz, J$_2$=16 Hz), 2.84 (1H, t, J=1.5 Hz), 1.48 (9H, s)

Reference, Example 36

Preparation of 3S-t-butoxycarbonylamino-1-phthalimidomethyl-3,4-dihydrocarbostyril Using N-bromomethyl phthalimide and a corresponding starting material, the captioned compound was obtained in the same manner as in Reference Example 24.
NMR (270 MHz, CDCl$_3$) δppm: 7.81 (2H, dd, J=6.3 Hz), 7.01 (2H, dd, J=6.3 Hz), 7.10–7.35 (3H, m), 7.02 (1H, t, J=7 Hz), 6.24 (1H, d, J=14 Hz), 5.75–5.90 (1 H, m), 5.74 (1H, d, J=14 Hz), 4.31 (1H, dt, J=14.5 Hz), 3.37 (1H, dd, J=14.5 Hz), 2.8 (1H, t, J=14 Hz), 1.47 (9H, s)

Reference Example 37

Preparation of 3S-t-butoxycarbonylamino-1-ethoxycarbonylmethyl-3,4-dihydrocarbostyril Using ethyl iodoacetate or ethyl bromoacetate and a corresponding starting material, the captioned compound was obtained in the same manner as in Reference Example 24.

NMR (270 MHz, CDCl$_3$) δ ppm: 7.23 (2H, d, J=8 Hz), 7.06 (1H, t, J=8 Hz), 6.79 (1H, d, J=8 Hz), 5.68 (1H, brs), 4.88 (1H, d, J=17 Hz), 4.47 (1H, d, J=1.7 Hz), 4.36 (1H, dt, J=14, 5 Hz), 4.21 (2H, q, J=7Hz), 3.44 (1H, dd, J=14, 5 Hz), 2.81 (1H, t, J=14 Hz), 1.47 (9H, s), 1.26 (3H, t, J=7 Hz)

Reference Example 38

Preparation of 3S-t-butoxycarbonylamino-7-chloro-1-ethoxycarbonylmethyl-3,4-dihydrocarbostyril Using ethyl bromoacetate and a corresponding starting material, the captioned compound was obtained in the same manner as in Reference Example 24.
NMR (270 MHz, CDCl$_3$) δ ppm:7.16 (1H, d, J=8 Hz, 7.04 (1H, dd, J=8, 2 Hz), 6.78 (1H, d, J=2 Hz), 5.64 (1H, brs), 4.82 (1H, d. J=18 Hz), 4.45 (1H, d, J=18 Hz), 4.25–4.45 (1H, m), 4.24 (2H, q, J=7 Hz), 3.43 (1H, dd, J=15, 5 Hz), 2.82 (1H, t, J=15 Hz), 1.47 (9H, s), 1.28 (3H, t, J=7 Hz)

Reference Example 39

Preparation of 1-benzyloxycarbonylmethyl-3S-t-butoxycarbonylamino-3,4-dihydrocarbostyril Using benzyl bromoacetate and a corresponding starting material, the captioned compound was obtained in the same manner as in Reference Example 24.
NMR (270 MHz, CDCl$_3$) δppm: 7.10–7.40 (7H, m), 7.05 (1H, t, J=8 Hz), 6.75 (1H, d, J=8 Hz), 5.67 (1H, brs), 5.18 (2H, s), 4.90 (1H, d, J=18 Hz), 4.56 (1H, d, J=18 Hz), 4.38 (1H, dt, J=14, 5Hz), 3.42 (1H, dd, J=14, 5 Hz), 2.83 (1H, t, J=14 Hz), 1.47 (9H, s)

Reference Example 40

Preparation of 3S-t-butoxycarbonylamino-1-carboxy-methyl-3,4-dihydrocarbostyril 2.98 g of 1-benzyloxycarbonylmethyl-3S-t-butoxy-carbonylamino-3,4-dihydrocarbostyril obtained in Reference Example 39 was dissolved in 10 ml of methanol, and 200 mg of 10% palladium-carbon suspended in 10 ml of methanol was added, and the mixture was saturated with hydrogen. After stirring for 1 day at ordinary pressure, the catalyst was filtered off, and the filtrate was evaporated in vacuum, and the captioned compound was obtained in a white solid form. Yield: 2.0 g.
NMR (270 MHz, CDCl$_3$) δ ppm: 7.20–7.26 (2H, m), 7.05 (1H, t, J=7 Hz), 6.81 (1H, d, J=8 Hz), 5.69 (1H, brs), 4.89 (1H, d, J=18 Hz), 4.45 (1H, d, J=18 Hz), 4.31–4.38 (1H, m), 3.37–3.43 (1H, m), 2.86 (1H, t, J=18 Hz), 1.46 (9H, s)

Reference Example 41

Preparation of 3S-t-butoxycarbonylamino-1-propoxy-carbonylmethyl-3,4-dihydrocarbostyril 600 mg of 3S-t-butoxycarbonylamino-1-carboxymethyl-3,4-dihydrocarbostyril obtained in Reference Example 40 was dissolved in 10 ml of dichloromethane, and 420 µl of propanol was added and cooled in an ice bath, and 247 µl of N-methylmorpholine, 430 mg of 1-ethyl-3-(3-dimethylaminopropyl) carbodiimide hydrochloride, and 11 mg of dimethylaminopyridine were added, and the mixture was stirred for 20 hours at room temperature. The reaction solution was evaporated in vacuum, and 40 ml of ethyl acetate was added to the residue, which was sequentially washed with 15 ml of 1N hydrochloric acid, 15 ml of aqueous solution of saturated sodium hydrogencarbonate, and 10 ml of saturated brine, and dried over magnesium sulfate, and evaporated in vacuum, and the captioned compound was obtained in a colorless oil form. Yield: 600 mg.

NMR (270 MHz, CDCl$_3$) δ ppm: 7.23 (2H, d, J=7 Hz), 7.06 (1H, t, J=7 Hz), 6.79 (1H, d, J=7 Hz), 5.68 (1H, brs), 4.87 (1H, d, J=17 Hz), 4.50 (1H, d, J=17 Hz), 4.35 (1H, dt, J=14, 5 Hz), 4.11 (2H, t, J=7 Hz), 3.45 (1H, dd, J=14, 5 Hz), 2.86 (1H, t, J=14 Hz), 1.83 (2H, dq, J=7, 7 Hz), 1.48 (9H, s), 0.88 (3H, t, J=7 Hz)

Reference Example 42

Preparation of 3S-t-butoxycarbonylamino-1isopropoxycarbonylmethyl-3,4-dihydrocarbostyril Using 2-propanol and a corresponding starting material, the captioned compound was obtained in the same manner as in Reference Example 41.

NMR (270 MHz, CDCl$_3$) δppm: 7.23 (2H, d, J=8 Hz), 7.06 (1H, t, J=8 Hz), 6.78 (1H, d, J=8 Hz) 5.69 (1H, brs), 4.95–5.15 (1H. m), 4.81 (1H, d, J=17 Hz), 4.47 (1H, d, J=17 Hz), 4.35 (1H, H, dt, J=14, 5 Hz), 3.45 (1H, dd, J=14, 5 Hz), 2.86 (1H, t, J=14 Hz), 1.47 (9H, s), 1.20–1.30 (6H, m)

Reference Example 43

Preparation of 3S-benzyloxycarbonylamino-1-t-butoxycarbonylmethyl-3,4-dihydrocarbostyril Using t-butyl bromoacetate and a corresponding starting material, the captioned compound was obtained in the same manner as in Reference Example 24.

NMR (270 MHz, CDCl$_3$) δppm: 7.23–7.39 (5H, m), 7.07 (2H, t, J=8 Hz), 6.79 (2H, d, J=8 Hz), 5.97 (1H, brs), 5.14 (2H, s), 4.74 (1H, d, J=17 Hz), 4.34–4.45 (2H, m), 3.47 (1H, dd, J=14, 6 Hz), 2.88 (1H, t, J=14 Hz), 1.42 (9H, s)

Reference Example 44

Preparation of 1-aminocarbonylmethyl-3S-t-butoxy-carbonylamino-3,4-dihydrocarbostyril Using iodoacetamide and a corresponding starting material, the captioned compound was obtained in the same manner as in Reference Example 24.

NMR (270 MHz, CDCl$_3$) δppm: 7.15–7.35 (2H, m), 7.05–7.15 (2H, m), 6.13 (1H, brs), 5.60 (1H, brs), 5.44 (1H, brs), 4. 95 (1H, d, J=16 Hz), 4.38 (1H, dt, J=14, 6 Hz), 4.19 (1H, d, J=16 Hz), 3.30–3.50 (1H, m), 2.88 (1H, t, J=14 Hz), 1.47 (9H, s)

Reference Example 45

Preparation of 3S-t-butoxycarbonylamino-1-(N-methyl-aminocarbonylmethyl)-3,4-dihydrocarbostyril 500 mg of 3S-t-butoxycarbonylamino-1-carboxymethyl-3,4-dihydrocarbostyril was dissolved in 10 ml of dichloromethane, and while stirring in ice-cooling, 240 mg of 1-hydroxybenzotriazole, 0.21 ml of N-methylmorpholine, and 358 mg of 1-ethyl-3-(3-dimethylaminopropyl)carbodiimide hydrochloride were added, and the mixture was stirred for 10 minutes, and 0.34 ml of N-methylmorpholine and 210 mg of methylamine hydrochloride were added, and the mixture was stirred overnight at room temperature. The reaction solution was concentrated in vacuo, and 30 ml of dichloromethane was added to the residue, and it was washed sequentially with 15 ml of 1N hydrochloric acid, 15 ml of aqueous solution of saturated sodium hydrogencarbonate, and 15 ml of saturated brine, and dried over magnesium sulfate anhydride. Evaporated in vacuum, the captioned compound was obtained in a white solid form. Yield: 540 mg.

NMR (270 MHz, CDCl$_3$) δppm: 7.06–7.32 (4H, m), 6.12 (1H, brs), 5.59 (1H, brs), 4.94 (1H, d, J=16 Hz), 4.34–4.44 (1H, m), 4.10 (1H, d, J=16 Hz), 3.41 (1H, dd, J=15, 8 Hz), 2.87 (1H, t, J=15 Hz), 2.82 (3H, d, J=5 Hz), 1.48 (9H, m)

Reference Example 46

Preparation of 3S-t-butoxycarbonylamino-1(N-propylaminocarbonylmethyl)-3,4-dihydrocarbostyril Using 1-propylamine and a corresponding starting material, the captioned compound was obtained in the same manner as in Reference Example 45.

NMR (270 MHz, CDCl$_3$) δppm: 7.06–7.32 (4H, m), 6.01 (1H, brs), 5.60 (1H, brs), 4.92 (1H, d, J=16 Hz), 4.34–4.42 (1H, m), 4.14 (1H, d, J=16 Hz), 3.43 (1H, dd, J=15, 8 Hz), 3.22 (2H, dq, J=2, 7 Hz), 2.86 (1H, t, J=15 Hz), 1.42–1.53 (11H, m), 0.86 (3H, t, J=7 Hz)

Reference Example 47

Preparation of 3S-t-butoxycarbonylamino-1-(N-methoxyaminocarbonylmethyl)-3,4-dihydrocarbostyril Using methoxyamine and a corresponding starting material, the captioned compound was obtained in the same manner as in Reference Example 45.

NMR (270 MHz, CDCl$_3$) δppm: 9.06 (1H, s), 7.15–7.40 (3H, m), 7.09 (1H, t, J=8 Hz), 5.55 (1H, brs), 4.75–4.95 (1H, m), 4.38 (1H. dt, J=14, 6 Hz), 4.00–4.20 (1H, m), 3.78 (3H, s), 3.39 (1H, dd, J=14, 5 Hz), 2.88 (1H, n, J=14 Hz), 1.48 (9H, s)

Reference Example 48

Preparation of 3S-t-butoxycarbonylamino-1-(N,N-dimethylaminocarbonylmethyl)-3,4-dihydrocarbostyril Using dimethylamine and a corresponding starting material, the captioned compound was obtained in the same manner as in Reference Example 45.

NMR (270 MHz, CDCl$_3$) δppm: 7.20–7.26 (2H, m), 7.03 (1H, t, J=8 Hz), 6.78 (1H, d, J=8 Hz), 5.78 (1H, brs), 4.93 (1H, d, J=17 Hz), 4.50 (1H, d, J=17 Hz), 4.34–4.43 (1H, m), 3.39–3.46 (1H, m), 3.13 (3H, s), 2.99 (3H, s), 2.90 (1H, t, J=14 Hz), 1.47 (9H, s)

Reference Example 49

Preparation of 3S-t-butoxycarbonylamino-1-morpholinocarbonylmethyl-3,4-dihydrocarbostyril Using morpholine and a corresponding starting material, the captioned compound was obtained in the same manner as in Reference Example 45.

NMR (270 MHz, CDCl$_3$) δppm: 7.22 (2H, d, J=7 Hz), 7.05 (1H, t, J=7 Hz), 6.80 (1H, d, J=7 Hz), 5.66 (1H, brs), 4.92 (1H, d, J=16 Hz), 4.52 (1H, d, J=16 Hz), 4.39 (1H, ds, J=14, 5 Hz), 3.73 (4H, dd, J=15, 4 Hz), 3.61 (4H, dd, J=15, 4 Hz), 3.43 (1H, dd, J=14, 5 Hz), 2.90 (1 H, J=14 Hz), 1.47 (9H, s)

Reference Example 50

Preparation of 1-allyl-3S-t-butoxycarbonylamino-3,4dihydrocarbostyril

Using allyl bromide and a corresponding starting material, the captioned compound was obtained in the same manner as in Reference Example 24.

NMR (270 MHz, CDCl₃) δppm: 7.23 (1H, d, J=8 Hz), 7.21 (1H, d, J=7 Hz), 7.06–6.99 (2H, m), 5.94–5.82 (1H, m), 5.75 (1H, bs), 5.23-5.12 (2H, m), 4.88-4.78 (1H, m), 4.35-4.26 (2H, m), 3.44 (1H, dd, J$_1$=5 Hz, J$_2$=15 Hz), 2.81 (1H, t, J=15 Hz), 1.48 (9H, s)

Reference Example 51

Preparation of 3S-t-butoxycarbonylamino-1-cinnamyl-3,4-dihydrocarbostyril

Using a starting material corresponding to cinnamyl bromide, the captioned compound was obtained in the same manner as in Reference Example 24.

NMR (270 MHz, CDCl₃) δppm: 7.36-7.19 (7H, m), 7.10-7.01 (2H, m), 6.54 (1H, d, J=16 Hz), 6.24 (1H, td, J$_1$=16 Hz, J$_2$=6 Hz), 5.76 (1H, b s), 4.99 (1H, ddd, J$_1$=2 Hz, J$_2$=6 Hz, J$_3$=17 Hz), 4.46 (1H, ddd, J$_1$=1 Hz, J$_2$=6 Hz, J$_3$=16 Hz), 4.37-4.31 (1H, m), 3.45 (1H, dd, J$_1$=5 Hz, J$_2$=1.5 Hz) 2.83 (1H t, J=15 Hz) 1 48 (9H, s)

Reference Example 52

Preparation of 3S-t-butoxycarbonylamino-1-methyl-3,4dihydrocarbostyril

Using iodomethane and a corresponding starting material, the captioned compound was obtained in the same manner as in Reference Example 24.

NMR (270 MHz, CDCl₃) δppm: 7.20–7.32 (2H, m), 6.98–7.08 (2H, m), 5.71 (1H, brs), 4.19–4.28 (1H, m), 3.48–3.50 (1H, m), 2.78 (1H, t, J=15 Hz), 1.48 (9H, s)

Reference Example 53

Preparation of 3S-t-butoxycarbonylamino-1-ethyl-3,4-dihydrocarbostyril

Using iodoethane and a corresponding starting material, the captioned compound was obtained in the same manner as in Reference Example 24.

NMR (270 MHz, CDCl₃) δppm: 7.15–7.35 (2H, m), 7.03 (2H, t, J=7 Hz), 5.74 (1H, brs), 4.24 (1H, dt, J=14.5 Hz), 3.85–4.20 (2H, m), 3.41 (1H, dd, J=14.5 Hz), 2.75 (1H, t, J=14 Hz), 1.47 (9H, s), 1.26 (3H, t, J=7 Hz)

Reference Example 54

Preparation of 1-benzyloxyethyl-3S-t-butoxycarbonylamino-3,4-dihydrocarbostyril

Using 1-benzyloxy-2-iodoethane and a corresponding starting material, the captioned compound was obtained in the same manner as in Reference Example 24.

NMR (270 MHz, CDCl₃) δppm: 7.15–7.40 (8H, m), 6.95–7.10 (1H, m), 5.71 (1H, brs), 4.52 (2H, s), 4.15–4.35 (2H, m), 3.95–4.15 (1H, m), 3.73 (2H, t, J=6 Hz), 3.39 (1H, dd, J=14, 6 Hz), 2.76 (1H, t, J=14 Hz), 1.47 (9H, s)

Reference Example 55

Preparation of 3S-t-butoxycarbonylamino-1-(2-hydroxyethyl)-3,4-dihydrocarbostyril 1.50 g of 1-benzyloxyethyl-3S-t-butoxycarbonylamino-3,4-dihydrocarbostyril was dissolved in 10 ml of ethanol, and 100 mg of 20% palladium hydroxide-on-carbon (wet) was added, and the mixture was saturated with hydrogen. After stirring for 1 day at ordinary pressure, the catalyst was filtered away, the filtrate was concentrated in vacuo, and the captioned compound was obtained. Yield: 1.05 g.

NMR (270 MHz, CDCl₃) δppm: 7.00–7.40 (4H, m), 5.70 (1H, brs), 4.15–4.40 (2H, m), 3.80–4.15 (3H, m), 3.40 (1H, dd, J=15, 7 Hz), 2.81 (1H, t, J=15 Hz), 2.23 (1H, brs), 1.47 (9H, s)

Reference Example 55

Preparation of 3S-t-butoxycarbonylamino-1(2-propynyl)-3,4-dihydrocarbostyril

Using propalgyl bromide and a corresponding starting material, the captioned compound was obtained in the same manner as in Reference Example 24.

NMR (270 MHz, CDCl₃) δppm: 7.21–7.35 (3H, m), 7.08 (1H, dt, J=1.7 Hz), 5.68 (1H, brs), 4.95 (1H, dd, J=17, 2 Hz), 4.47 (1H, dd, J=17, 2 Hz), 4.25–4.44 (1H, m), 3.42 (1H, dd, J=15, 5 Hz), 2.80 (1H, t, J=15 Hz), 2.54 (1H, t, J=2 Hz), 1.47 (9H, s)

Reference Example 57

Preparation of 7-chloro-3S-phthalimido-3,4-d dihydrocarbostyril 2.82 g of 3S-amino-7-chloro-3,4-dihydrocarbostyril was suspended in 40 ml of dimethylformamide, and 3.46 g of N-carboethoxyphthalimide and 1.52 g of sodium carbonate were added, and the mixture was stirred overnight at room temperature. The reaction solution was concentrated in vacuo, and 50 ml of water was added to the residue, and the precipitates were filtered. The crude product was washed with 30 ml of ethyl acetate and 30 ml of methanol, and the captioned compound was obtained in a pale brown powder form.

Yield: 4.02 g.

NMR(270 MHz, DMSO-d₆)δppm:10.69(1H, brs), 7.89–7.97(4H, m), 7.25(1H, d, J=8Hz), 7.04(1H, dd, J=8,2 Hz), 6.95(1H, d, J=2 Hz), 5.06(1H, dd, J=15, 7 Hz), 3.66(1H, t, J=15 Hz), 3.15(1H, dd, J=15, 7 Hz)

Reference Example 58

Preparation of 3S-triphenylmethylamino-3,4-dihydrocarbostyril 2.26 g of 3S-amino-3,4-dihydrocarbostyril was suspended in 40 ml of dimethyl formamide, and while stirring in ice-cooling, 5.03 g of triphenylmethyl chloride was added, and the pH was adjusted to 8 by triethylamine. After stirring for 1 hour at 0° C., returning to room temperature, the pH was adjusted again to 8 by triethylamine, and the solution was stirred for 1 hour. The reaction solution was concentrated in vacuo, and 100 ml of ethyl acetate was added, and it was washed sequentially with 1N hydrochloric acid (80 ml), aqueous solution of saturated sodium hydrogencarbonate (50 ml×2 times), and saturated brine (50 ml×2 times), and dried over magnesium sulfate anhydride, and evaporated in vacuum. To the residue, n-hexane was added, precipitates were filtered, and the captioned compound was obtained. Yield: 5.34 g.

NMR(270 MHz, CDCl₃)δppm:7.52–7.57(6H, m), 7.44(1H, br), 7.19–7.32(9H, m), 7.10(1H, %, J=8 Hz), 6.87(1H, t, J=8 Hz), 6.69(1H, d, J=8 Hz), 6.64(1H, d, J=8 Hz), 3.4! (1H, dd, J=6.15Hz), 2.46(1H, t, J=15Hz), 1.65(1H, dd, J=6.15 Hz)

Reference Example 59

Preparation of 3S-(tert-butoxycarbonyl)amino-7-chloro-1-methoxy-3,4-dihydrocarbostyril Using iodomethane and a corresponding starting material, the captioned compound was obtained in the same manner as in Reference Example 21.

NMR(270 MHz, CDCl$_3$)δppm:7.22(1H, d, J=2 Hz), 7.14(1H, d, J=8 Hz), 7.05(1H, dd, J=2,8 Hz), 5.55(1H, br), 4.34(1H, dt, J=14,6 Hz), 3.94(3H, s), 3.42(1H, dd, J=14,6 Hz), 2.77(1H, t, J=14 Hz), 1.48(9H, s)

Reference Example 60

Preparation of 3S-(4-hydroxy-2R-isobutyl-3S-methylsuccinyl)amino-1-methoxymethyl-3,4-dihydrocarbostyril 3S-(4-hydroxy-2R-isobutyl-3-ethenysuccinyl)amino-1-methoxymethyl-3,4-dihydrocarbostyril (800 mg, 2.14 mmol) obtained in the same manner as in Reference Example 4 was dissolved in ethanol (10 ml), and 10% palladium-carbon (100 mg) was added, and the mixture was saturated with hydrogen. After stirring for 1 day at ordinary pressure, the catalyst was filtered off, and the solvent was evaporated in vacuo, and the captioned compound was obtained. Yield: 790 mg.

NMR(270 MHz, DMSO-d$_6$)δppm:8.50(1H, d, J=8 Hz), 7.15–7.35(3H, m), 7.06(1H, t, J=7 Hz), 5.48(1H, d, J=10 Hz ), 5.02(1H, d, J=10 Hz), 4.57(1H, dt, J=14,7 Hz), 3.26(3H, s), 3.05(1H, t, J=14 Hz), 2.94(1H, dd, J=14,7 Hz), 2.80–3.20(1H, m), 2.20–2.45(1H, m), 1.40–1.70(2H, m), 0.90–1.20(1H, m), 1.04(3H, d, J=7 Hz), 0.90(3H, d, J=7 Hz), 0.83(3H, d, J=7 Hz)

Reference Example 61

Preparation of 3S-benzyloxycarbonylamino-1-methoxyethoxymethyl-3,4-dihydrocarbostyril Using methoxyethoxymethyl chloride and a corresponding starting material, the captioned compound was obtained in the same manner as in Reference Example 24.

NMR(270 MHz, CDCl$_3$)δppm:7.20–7.50(7H, m), 7.20(1H, d, J=7 Hz), 7.09(1H, t, J=7 Hz), 5.92(1H, brs), 5.82(1H, d, J=11 Hz), 5.15(2H, s), 5.01(1H, d, J=11 Hz), 4.40(1H, dt, J=14,6 Hz), 3.72(2H, dd, J=5.3 Hz), 3.53(2H, t, J=5 Hz), 3.41(1H, dd, J=14,6 Hz), 3.37(3H, s), 2.83(1H, t, J=14 Hz)

Reference Example 62

Preparation of 4-t-butoxy-2R-isobutyl-3-propylsuccinic acid

Using aryl bromide and a corresponding starting material, the captioned compound was obtained in the same manner as in Reference Example 8.

NMR(270 MHz, CDCl$_3$) δppm:2.68(1H, dt, J$_1$=3 Hz, J$_2$=9 Hz), 2.50(1H, dt, J$_1$=2 Hz, J$_2$=10 Hz), 1.74-1.12(16H, m), 1.45(9H, s), 0.96-0.87(9H, m)

Reference Example 63

Preparation of 3-benzyl-4-t-butoxy-2R-isobutylsuccinic acid

Using benzyl bromide and a corresponding starting material, the captioned compound was obtained in the same manner as in Reference Example 8.

NMR(270 MHz, CDCl$_3$)δppm:7.26-7.16( 5H, m), 2.91-2.74(4H, m), 1.77-1.60(2H, m), 1.29-1.18(10H, m), 1.26(9H, s), 0.91(6H, dd, J$_1$=3 Hz, J$_2$=7 Hz)

Reference Example 64

Preparation of 4-t-butoxy-2R-isobutyl-3-(4-methoxybenzyl)succinic acid

Using 4-methoxybenzyl chloride and a corresponding starting material, the captioned compound was obtained in the same manner as in Reference Example 8.

NMR(270 MHz, CDCl$_3$)δppm:7.09(2H, d, J=9 Hz), 6.79(2H, d, J=9 Hz), 3.77(3H, s), 2.87-2.72(4H, m), 1.72-1.59(2H, m), 1.33-1.21(10H, m), 1.28(9H, s), 0.90(6H, dd, J$_1$=3 Hz, J$_2$=7 Hz)

Reference Example 65

Preparation of benzyl 2-benzyloxycarbonyl-3S-tert-butoxycarbonyl-5-methylhexanoate Using L-leucin, the captioned compound was obtained in the same manner as in Reference Example 1.

Reference Example 66

Preparation of 3S-benzyloxycarbonylamino-1-methoxymethoxyethyl-3,4-dihydrocarbostyril Using 1-iodo-2-methoxymethoxyethane and a corresponding starting material, the captioned compound was obtained in the same manner as in Reference Example 24.

NMR(270 MHz, CDCl$_3$)δppm:7.15–7.45(8H, m), 7.06(1H, t, J=7 Hz), 6.01(1H, brs), 5.15(2H, s), 4.59(2H, q, J=6 Hz), 4.25–4.40(1 H, m), 4.25(1H, dt, J=14,5 Hz), 4.08(1H, dt, J=14,7 Hz), 3.78(2H, t, J=5 Hz), 3.44(1H, dd, J=15,6 Hz), 3.29(3H, s), 2.81(1H, t, J=15 Hz)

Reference Example 67

Preparation of 4-t-butoxy-2R-isobutyl-3-(Sphenylpropyl)succinic acid

Using cinnamyl bromide and a corresponding starting material, the captioned compound was obtained in the same manner as in Reference Example 8.

NMR(270 MHz, CDCl$_3$)δppm:7.29-7.13(5H, m), 2.71-2.50 (4H, m), 1.74-1.42(15H, m), 1.43(9H, s), 1.20-1.12(1H, m), 0.90(6H, d, J=7 Hz)

Reference Example 68

Preparation of 4-t-butoxy-2R-isobutyl-3-(2-methylbenzyl)succinic acid

Using α-bromo-o-xylene and a corresponding starting material, the captioned compound was obtained in the same manner as in Reference Example 8.

NMR( 270 MHz, CDCl$_3$)δppm:7.12-7.06(4H, m), 2.91-2.79(4H, m), 2.29(3H, s), 1.77-1.60(2H, m), 1.29-1.17(10H, m), 1.25(9H, m), 0.92(6H, dd, J$_1$=1 Hz, J$_2$=6 Hz)

Reference Example 69

Preparation of 4-t-butoxy-2R-isobutyl-S-(3-methylbenzyl)succinic acid

Using α-bromo-m-xylene and a corresponding starting material, the captioned compound was obtained in the same manner as in Reference Example 8.

NMR(270 MHz, CDCl$_3$)δppm:7.17-6.95(4H, m), 2.89-2.73(4H, m), 2.29(3H, s), 1.79-1.54(2H, m), 1.31-1.20(10H, m), 1.27(9H, s), 0.91(6H, dd, J$_1$=3 Hz, J$_2$=7 Hz)

Reference Example 70

Preparation of 4-t-butoxy-2R-isobutyl-3-(4-methylbenzyl)succinic acid

Using α-bromo-p-xylene and a corresponding starting material, the captioned compound was obtained in the same manner as in Reference Example 8.

NMR(270 MHz, CDCl$_3$)δppm:7.05(4H, s), 2.88–2.70(4H, m), 2.29(3H, s), 1.76–1.59(2H, m), 1.33–1.17(10H, m), 1.28(9H, s), 0.90(6H, dd, J$_1$=4 Hz, J$_2$=7 Hz)

Reference Example 71

Preparation of 4S-isopropyl-3-(1-oxononyl)-2-oxazolidinone

4S-Isopropyl-2-oxazolidinone (1.02 g, 7.90 mmol) was dissolved in tetrahydrofurane (25 ml) in nitrogen atmosphere, and cooled to −78° C. Dripping n-butyl lithium (1.63M hexane solution) (5.09 ml, 8.30 mmol), the solution was stirred for 30 minutes. Adding pelargonyl chloride (5.09 ml, 8.67 mmol), the solution was stirred for 1.5 hours at −78° C. The reaction solution was poured into 5% aqueous solution of ammonium chloride (30 ml), and extracted with ethyl acetate (30 ml×2 times), and the organic layer was washed with water (10 ml) and saturated brine (20 ml), and dried over magnesium sulfate. The solvent was evaporated in vacuo, and the captioned compound was obtained in a colorless oily form. Yield: 2.10 g.

NMR(270 MHz, CDCl$_3$)δppm:4–40(1H, dt, J=8.4 Hz), 4.26(1H, t, J=9 Hz), 4.19(1H, dd, J=9.3 Hz), 2.75–3.05(2H, m), 2.25–2.50(1H, m), 1.50–1.75(2H, m), 1.15–1.50(10H, m), 0.91(3H, d, J=7 Hz), 0.86(3H, d, J=7 Hz), 0.80–1.00(3H, m)

Reference Example 72

Preparation of 4S-isopropyl-3-(2R-t-butoxycarbonyl-methyl-1-oxononyl)-2-oxazolidinone Tetrahydrofurane (2.5 ml) was added to diisopropylamine (1.38 ml, 9.85 mmol), being ice-cooling, n-butyl lithium (1.63M hexane solution) (5.50 ml, 8.97 mmol) was dripped, and the solution was stirred for 15 minutes, and cooled to −78° C., and tetrahydrofurane (5 ml) solution of 4S-isopropyl-3-(1-oxononyl)-2-oxazolidinone (2.30 g, 8.54 mmol) was dripped, and the solution was stirred for 30 minutes at −78° C. Adding t-butylbromoacetate (1.66 ml, 10.28 mmol), the temperature was gradually raised to −5° C. while stirring for 7 hours. The reaction solution was poured into 5% aqueous solution of ammonium chloride, and extracted with ethyl acetate (20 ml×2 times), and the organic layer was washed sequentially with water (20 ml) and saturated brine (20 ml), and dried over magnesium sulfate. The solvent was evaporated in vacuo, and purified by silica gel chromatography (eluted in hexane:ethyl acetate=14:1), and the captioned compound was obtained.

Yield: 2.19 g.

NMR(270 MHz, CDCl$_3$) δppm: 4.43 (1H, dt, J=8,4 Hz), 4.10–4.35(3H, m), 2.74(1H, dd, J=16,10 Hz), 2.42(1H, dd, J=16,4 Hz), 2.30–2.55 (1H, m), 1.41(9H, s), 1.10–1.75(12H, m), 0.93(3H, d, J=6 Hz), 0.88(3H, d, J=6 Hz), 0.80–1.10(3H, m)

Reference Example 73

Preparation of 3S-[(2R-t-butoxycarbonylmethyl)-(1oxononyl)]-(1-oxononyl)]amino-1-methoxy-3,4-dihydrocarbostyril 4S-Isopropyl-3-(2R-t-butoxycarbonylmethyl-1-oxononyl)-2-oxazolidinone (2.19 g, 5.71 mmol) was dissolved in a mixed solvent of tetrahydrofurane-water (3:1, 120 ml), and cooled to 0° C. Adding sequentially lithium hydroxide hydrate (479 mg, 11.42 mmol) and 30% aqueous solution of hydrogen peroxide (2.94 ml), the solution was stirred for 1.5 hours at 0° C. Adding 1.5N aqueous solution of sodium sulfite (21.5 ml), the solution was stirred for several minutes, and the mixture was poured into methylene chloride (150 ml), and washed sequentially with 1N hydrochloric acid (50 ml) and saturated brine (20 ml), and dried over magnesium sulfate. After evaporating the solvent in vacuo, adding dimethyl formamide (10 ml), the solution was ice-cooled, and 3S-amino-1-methoxy-3,4-dihydrocarbostyril hydrochloride (1.30 g, 5.71 mmol), N-methylmorpholine (628 µl, 5.71 mmol), 1-hydroxybenzotriazole (873 mg, 5.71 mmol), and dicyclohexylcarbodiimide (1.18 g, 5.71 mmol) were sequentially added, and the mixture was stirred for 15 hours at room temperature. The solvent was evaporated in vacuo, ethyl acetate (50 ml) was added, and the mixture was sequentially washed with 1N hydrochloric acid (20 ml), saturated aqueous solution of sodium hydrogencarbonate (20 ml×2), and saturated brine (30 ml), and dried over magnesium sulfate. After evaporating the solvent in vacuo, it was purified by silica gel column chromatography (eluted in hexane:ethyl acetate=3:1), and the captioned compound was obtained. Yield: 2.70 g.

NMR(270 MHz, CDCl$_3$)δppm:7.15–7.40(3H, m), 7.08(1H, t, J=7 Hz) 6.63(1H, d, J=6 Hz), 4.60(1H, dt, J=14,6 Hz), 3.94(3H, s), 3.49(1H, dd, J=15, 6 Hz), 2.76(1H, t, J=15 Hz), 2.55–2.80(2H, m), 2.30–2.50(1H, m), 1.45(9H, s), 1.20–1.80(12H, m), 0.87(3H, t, J=7 Hz)

Reference Example 74

Preparation of 7-chloro-1-methoxymethyl-3S-phthalimido-3,4-dihydrocarbostyril

Using methoxymethyl chloride and a corresponding starting material, the captioned compound was obtained in the same manner as in Reference Example 24.

NMR(270 MHz, CDCl$_3$)δppm:7.86–7.93(2H, m), 7.73–7.79(2H, m), 7.39(1H, d, J=2 Hz), 7.06–7.14(2H, m), 5.68(1H, d, J=11 Hz), 5.15(1H, dd, J=15, 6Hz), 4.99(1H, d, J=11 Hz), 4.02(1H, t, J=6 Hz), 3.41(3H, s), 2.97(1H, dd, J=14,6 Hz)

Reference Example 75

Preparation of 3(R,S)-benzyloxycarbonylamino-1-tert-butoxyethyl-3,4-dihydrocarbostyril Using 1-iodo-2-tert-butoxyethane and a corresponding starting material, the captioned compound was obtained in the same manner as in Reference Example 24.

NMR(270 MHz, CDCl$_3$)δppm:6.99–7.40(9H, m), 6.00(1H, br), 5.12–5.17(2H, m), 4.08–4.35(2H, m), 3.87(1H, dt, J=14,7 Hz), 3.55–3.64(3H, m), 2.80(1H, t, J=14 Hz), 1.12(9H, s)

Reference Example 76

Preparation of 1-methoxyethyl-3S-triphenylmethyl-amino-3,4-dihydrocarbostyril

Using 1-iodo-2-methoxyethane and a corresponding starting material, the captioned compound was obtained in the same manner as in Reference Example 24.

NMR(270 MHz, CDCl$_3$)δppm:7.49–7.54(6H, m), 7.08–7.31(11H, m), 6.88(1H, dt, J=2,8 Hz), 6.66(1H, d, J=8 Hz), 4.20(1H, dt, J=14, 5 Hz), 3.98(1H, dt, J=14,7 Hz), 3.59(1H, dd, J=7,5 Hz), 3.37(1H, dd, J=14,5 Hz), 3.34(3H, s), 2.36(1H, t, J=14 Hz), 1.56(1H, dd, J=14, 5 Hz)

Reference Example 77

Preparation of 3(R,S)-benzyloxyamino-1-methoxyethyl-3,4-dihydrocarbostyril

Using 1-iodo-2-methoxyethane and a corresponding starting material, the captioned compound was obtained in the same manner as in Reference Example 24.
NMR(270 MHz, CDCl$_3$)δppm:7.19–7.40(8H, m), 7.05(1H, t, J=7 Hz), 5.99(1H, br), 5.15(2H, s), 4.33(1H, dt, J=14,5 Hz), 4.25(1H, dt, J=14, 5 Hz), 4.00(1H, dt, J=14,7Hz), 3.59–3.68(2H, m), 3.44(1H, dd, J=14,5 Hz), 3.35(1H, s), 2.81(1H, t, J=14Hz), 1.12(9H, s)

Reference Example 78

Preparation of 4-t-butoxy-2R-isobutyl-3-(4-methoxycarbonylbenzyl)succinic acid

Using 4-methoxycarbonylbenzyl bromide and a corresponding starting material, the captioned compound was obtained in the same manner as in Reference Example 8.
NMR(270 MHz, CDCl$_3$)δppm:7.94(2H, d, J=8 Hz), 7.25(2H, d, J=8 Hz), 3.90(3H, s), 2.97-2.74(4H, m), 1.78-1.60(2H, m), 1.29–1.18 (10H, m), 1.26(9H, s), 0.91(6H, dd, J$_1$=3 Hz, J$_2$=6 Hz)

Reference Example 79

Preparation of 4-t-butoxy-3-hexyl-2R-isobutylsuccinic acid

Using 1-iodohexane and a corresponding starting material, the captioned compound was obtained in the same manner as in Reference Example 8.
NMR(270 MHz, CDCl$_3$)δppm:2.71(1H, dt, J$_1$=4 Hz, J$_2$=9 Hz), 2.52(1H, dt, J$_1$=4 Hz, J$_2$=9 Hz), 1.76-1.55(2H, m), 1.49(9H, s), 1.30–1.15(11H, m), 0.99–0.88(9H, m)

Reference Example 80

Preparation of benzyl 2-benzyloxycarbonyl-3R-t-butoxycarbonyl-pentanoate

Using D-norleucine and a corresponding starting material, the captioned compound was obtained in the same manner as in Reference Example 1.

Reference Example 81

Preparation of 4-t-butoxy-2R-isobutyl-3-(3,4-methylenedioxybenzyl)succinic acid

Using 3,4-methylenedioxybenzyl chloride and a corresponding starting material, the captioned compound was obtained in the same manner as in Reference Example 8.
NMR(270 MHz, CDCl$_3$)δppm:6.71-6.60(3H, m), 5.91(2H, s), 2.83-2.69(4H, m), 1.75-1.56(2H, m), 1.32(9H, s), 1.25-1.16(1H, m), 0.90(6H, dd, J$_1$=3 Hz, J$_2$=7 Hz)

Reference Example 82

Preparation of 4-t-butoxy-3-(3-ethoxycarbonylpropyl)-2R-isobutylsuccinic acid

Using ethyl 4-bromocrotonate and a corresponding starting material, the captioned compound was obtained in the same manner as in Reference Example 8.
NMR(270 MHz, CDCl$_3$)δppm:4.12(2H, q, J=7 Hz ), 2.73-2.63 (1H, m), 2.53-2.46 (1H, m ), 2.34-2.29 ( 2H, m), 1.73-1.51(6H, m), 1.46(9H, s), 1.28-1.16(4H, m), 1.25(3H, t, J=7 Hz ), 0.90 ( 6H, d, J=6 Hz)

Reference Example 83

Preparation of 1-ethoxymethyl-3S-triphenylmethylamino-3,4-dihydrocarbostyril

Using ethoxymethyl chloride and a corresponding starting material, the captioned compound was obtained in the same manner as in Reference Example 24.
NMR(270 MHZ, CDCl$_3$)δppm:7.52(6H, d, J=7 Hz), 7.10–7.40(11H, m), 6.93(1H, dt, J=1.7 Hz), 6.68(1H, d, J=7 Hz), 5.76(1H, d, J=10 Hz), 4.94(1H, d, J=10 Hz), 3.45–3.60(2H, m), 3.43(1H, dd, J=14.5 Hz), 2.44(1H, t, J=14 Hz), 1.67(1H, dd, J=14.5 Hz), 1.19(3H, t, J=17 Hz)

Reference Example 84

Preparation of O-butyl-D-serine

To a mixed solution of 60% sodium hydride (28.8 g), imidazole (1.08 g, 15.9 mmol), and dry tetrahydrofurane (270 ml), a mixed solution of N-trityl-D-serine (25.0 g, 72.0 mmol) and dry tetrahydrofurane (150 ml) was dripped in 15 minutes at −15° C., and the mixture was stirred for 45 minutes at −15° C. Further, butyl iodide (65.5 ml, 576 mmol) was added, and the mixture was stirred for 2 hours at −15° C. Moreover, at −15° C., adding 60% sodium hydride (12.0 g) and butyl iodide (129 ml, 1.13 mol), the mixture was stirred for 1 day at −20° C. Adding water (1 liter) to the reaction solution, it was extracted with ether (300 ml×2), and the organic layer was washed with 5% aqueous solution of citric acid (200 ml) and saturated brine (100 ml), and dried over magnesium sulfate. The solvent was evaporated in vacuo, and 50% acetic acid-ethanol solution (100 ml) was added to the obtained oily matter, and the mixture was stirred for 15 hours at room temperature. The sediment was filtered, and washed with ethanol and ether, and O-butyl-D-serine (6.11 g, 53%) was obtained.
NMR(270 MHz, D$_2$O)δppm:3.75–4.00(3H, m), 3.50–3.70(2H, m), 1.57(2H, dt, J=14.7 Hz), 1.33(2H, dt, J=14.7 Hz), 0.90(3H, t, J=7 Hz)

Reference Example 85

Preparation of benzyl 2-benzyloxycarbonyl-3S-tert-butoxycarbonyl-4-butoxy-butylate Using O-butyl-D-serine and a corresponding starting material, the captioned compound was obtained in the same manner as in Reference Example 1.

Reference Example 86

Preparation of O-nitrophenyl-L-alanine

To N-acetyl-O-nitrophenyl-DL-alanine (324 g, 1.28 mol), aqueous solution (1.8 liters) of 1N sodium hydroxide was added to dissolved, and acylase (9.0 g) and cobalt (II) chloride hexahydrate (100 mg) were sequentially added, and the mixture was stirred for 2 days at 37° C. After filtering the insoluble matter, the filtrate was evaporated in vacuo, and precipitating crystals were filtered and washed with a small amount of water, and the captioned compound (99.6 g, 37%) was obtained.

Reference Example 87

Preparation of 3S-(4-hydroxy-2-isobutyl-3-methylthiomethylsuccinyl)amino-3,4-dihydrocarbostyril A mixed liquid of 3S-(4-hydroxy-2-isobutyl-3-acetylthiomethylsuccinyl)amino-3,4-dihydrocarbostyril (800 mg, 1.97 m mol) and methanol (10 ml) was chilled in ice. An aqueous solution (8 ml) of 1N sodium hydroxide was added, and the mixture was stirred for 40 minutes in ice-cooling. Methyl iodide (430 μl, 6.91 m mol) was added, and further the mixture was stirred for 2 hours in ice-cooling. Then, 1N-hydrochloric acid (10 ml) was added, the precipitating crystals were filtered, and the captioned compound was obtained in a yellow solid (330 mg, 44%).
NMR(270 MHz, DMSO-$d_6$)δppm:10.22(1H, s), 8.47(1H, d, J=8 Hz), 7.18(2H, q, J=8 Hz), 6.89(2H, dd, J=11.8 Hz), 4.43(1H, dt, J=14.7 Hz), 2.80–3.20(3H, m), 2.40–2.80(3H, m), 2.04(3H, s), 1.35–1.70(2H, m), 0.90–1.05(1H, m), 0.87(3H, d, J=7 Hz), 0.83(3H, d, J=7 Hz)

Reference Example 88

Preparation of 3S-amino-1-ethoxyethoxy-3,4-dihydrocarbostril

Sodium hydride, oilhess (186 mg) was washed twice with hexane (2 ml), suspended in dimethyl formamide (14 ml), and 3S-amino-1-hydroxy-3,4-dihydrocarbostyril hydrochloride (500 mg, 2.33 m mol) was added. The mixture was stirred for 20 minutes in ice-cooling and then for 1 hour in room temperature.

The mixture was chilled in ice again, and 2-iodoethylethylether (513 mg, 256 m mol) was added. The mixture was stirred for 20 minutes in ice-cooling and for 1 hour in room temperature. The solvent was evaporated in vacuo, and to the obtained residue, water (30 ml) was added. The mixture was extracted twice with dichloromethane (30 ml), and the organic layers were combined, washed with saturated saline water (30 ml) and dried over magnesium sulfate. The solvent. was evaporated in vacuo to obtained the captioned compound (522 mg, 90%).
NMR(270 MHz, CDCl$_3$)δppm:7.40(1H, t, J=8 Hz), 7.10–7.35(2H, m), 7.05(1H, t, J=8 Hz), 4.20–4.35(2H, m), 3.60–3.80((2H, m), 3.65(1H, dd, J=13,6 Hz), 3.53(2H, q, J=7 Hz), 3.10(1H, dd, J=15.6 Hz), 2.86(1H, t, J=15 Hz), 1.23(3H, t, J=7 Hz)

Reference Example 89

Preparation of 3S-amino-1-methoxymethoxyethoxy-3,4-dihydrocarbostyril

Using 1-iodo-2-methoxymethoxyethane, the captioned compound was obtained in the same manner as in Reference Example 88.
NMR(270 MHz, CDCl$_3$)δppm:7.37(1H, d, J=7 Hz), 7.33(1H, d, J=7 Hz), 7.20(1H, d, J=7 Hz), 7.05(1H, td, J=7.1 Hz), 4.68(2H, s), 4.20–4.40 (2H, m), 3.75–3.95(2H, m), 3.64(1H, dd, J=13,6 Hz), 3.38(3H, s), 3.11(1H, dd, J=15, 6 Hz), 2.85(1H, t, J=15 Hz)

Reference Example 90

Preparation of 3S-t-butoxycarbonylamino-1-methoxy-7-methoxy-3,4-dihydrocarbostyril Using a corresponding starting material, the captioned compound was obtained in the same manner as in Reference Example 21.
NMR(270 MHz, CDCl$_3$)δppm:7.11(1H, d, J=8 Hz), 6.79(1H, d, J=2 Hz), 6.60(1H, dd, J=8,2 Hz), 5.57(1H, brs), 4.33(1H, dt, J=14,6 Hz), 3.92(3H, s), 3.82(3H, s), 3.36(1H, dd, J=14,4 Hz), 2.73(1H, t, J=14 Hz), 1.48(9H, s)

Reference Example 91

Preparation of 3S-t-butoxycarbonylamino-1-ethoxy-7-methoxy-3,4-dihydrocarbostyril Using ethyl iodide and a corresponding starting material, the captioned compound was obtained in the same manner as in Reference Example 21.
NMR(270 MHz, CDCl$_3$)δppm:7.11(1H, d, J=8 Hz), 6.79(1H, d, J=3 Hz), 6.59(1H, dd, J=8,3 Hz), 5.57(1H, brs), 4.31(1H, dt, J=14,6 Hz), 4.05–4.25(2H, m), 3.82(3H, s), 3.37(1H, dd, J=15, 6 Hz), 2.72 ( 1H, t, J=15 Hz), 1.49(9H, s), 1.38(3H, t, J=7 Hz)

Reference Example 92

Preparation of 3S-t-butoxycarbonylamino-1-methoxyethyl-6,7-methylenedioxy-3,4-dihydrocarbostyril Using 1-iodo-2-methoxyethane and a corresponding starting material, the captioned compound was obtained in the same manner as in Reference Example 24.
NMR(270 MHz, DMSO-$d_6$)δppm:6.89(1H, s), 6.65(1H, s), 5.94(2H, dd, J$_1$=1 Hz, J$_2$=2 Hz), 5.70(1H, bs), 4.25-4.14(2H, m), 3.93–3.82(1H, m), 3.62-3.60(2H, m), 3.34(3H, s), 3.29-3.23(1H, dd, J$_1$=5 Hz, J$_2$14 Hz), 2.67(1H, t, J=15 Hz), 1.47(9H, s)

Reference Example 93

Preparation of 3-benzyloxycarbonylamino-6,7-dimethoxy-1-methoxymethyl-3,4-dihydrocarbostyril Using methoxymethyl chloride and a corresponding starting material, the captioned compound was obtained in the same manner as in Reference Example 24.
NMR(270 MHz, CDCl$_3$)δppm:7.30–7.34(5H, m), 6.96(1H, s), 6.71(1H, s), 5.96(1H, brs), 5.71(1H, d, J=11 Hz), 5.15(2H, s), 4.89(1H, d, J=11 Hz), 4.38(1H, dt, J=14,5 Hz), 3.88(3H, s), 3.86(3H, s), 3.40(3H, s), 3.36(1H, dd, J=14,5 Hz), 2.76(1H, t, J=14 Hz)

Reference Example 94

Preparation of 3-amino-6,7-dimethoxy-3,4-dihydrocarbostyril hydrochloride

Using 2-nitro-4,5-dimethoxybenzyl chloride, the captioned compound was obtained in accordance with a method described in J. Med. Chem. 1972, 15, 325.
NMR( 270 MHz, DMSO$_6$)δppm:10.49(1H, s), 8.52(3H, s), 6.92( 1H, s), 6.56(1H, s), 4.06–4.16(1H, m), 3.72(3H, s), 3.70(3H, s), 3.12(1H, dd, J=14,7 Hz), 2.98(1H, t, J=14Hz)

Reference Example 95

Preparation of 8-methoxy-1-methoxyethyl-3S-tritylamino-3,4-dihydrocarbostyril

Using 1-iodo-2-methoxyethane and a corresponding starting material, the captioned compound was obtained in the same manner as in Reference Example 24.
NMR(270 MHz, CDCl$_3$) δppm:7.49-7.45(6H, m), 7.30-7.18(9H, m), 6.90(1H, t, J=8 Hz), 6.74(1H, d, J=8 Hz), 6.25(1H, d, J=8 Hz), 4.45(2H, m), 4.14-4.09(1H, m), 3.80(3H, s), 3.49-3.41(2H, m), 3.28(1H, dd, J$_1$=5 Hz, J$_2$=14 Hz), 3.23(3H, s ), 2.36( 1H, t, J=14 Hz), 1.28(1H, dd, J$_1$=8 Hz, J$_{2=15}$ Hz)

Reference Example 96

Preparation of 1-methoxyethoxy-3S-triphenylmethylamino-3,4-dihydrocarbostyril

Using 1-iodo-2-methoxyethane and a corresponding starting material, the captioned compound was obtained in the same manner as in Reference Example 24.

NMR(270 MHz, CDCl$_3$)δppm:7.51–7.56(6H, m), 7.22–7.32(11H, m), 6.91(1H, dt, J=2.7 Hz), 6.66(1H, d, J=7 Hz), 4.23–4.30(1H, m), 4.08–4.20(1H, m), 3.95(1H, d, J=3 Hz), 3.63–3.76(2H, m), 3.44(1H, ddd, J=14,5, 3 Hz), 3.39(3H, s), 2.33(1H, t, J=14 Hz), 1.56(1H, dd, J=14.5 Hz)

Reference Example 97

Preparation of 3S-amino-1-methoxyethoxymethoxyethoxy-3,4-dihydrocarbostyril

Using 1-iodo-2-methoxyethoxymethoxyethane and a corresponding starting material, the captioned compound was obtained in the same manner as in Reference Example 88.

NMR(270 MHz, CDCl$_3$)δppm:7.10–7.45(3H, m), 7.06(1H, td, J=7.2 Hz), 4.77(2H, s), 4.20–4.40(2H, m), 3.75–3.95(2H, m), 3.45–3.75(5H, m), 3.38(3H, s), 3.11(1H, dd, J=15.6 Hz), 2.86(1H, t, J=15 Hz)

Reference Example 98

Preparation of 3S-amino-1-methoxyethoxyethoxy-3,4-dihydrocarbostyril

Using 1-iodo-2-methoxyethoxyetane and a corresponding starting material, the captioned compound was obtained in the same manner as in Reference Example 88.

NMR(270 MHz, CDCl$_3$)δppm: 7.39(1H, t, J=7 Hz), 7.10–7.35(2H, m), 7.05(1H, t, J=7Hz), 4.20-4.40(2H, m), 3.70–3.90(2H, m), 3.50–3.70(5H, m), 3.40(3H, s), 3.10(1H, dd, J=15.6 Hz), 2.86(1H, t, J=15 Hz)

Reference Example 99

Preparation of 6,7-methylenedioxy-3S-triphenylmethylamino-3,4-dihydrocarbostyril Using triphenylmethyl chloride and a corresponding starting material, the captioned compound was obtained in the same manner as in Reference Example 58.

NMR (270 MHz, CDCl$_3$) δppm: 7.63 (1H, brs), 7.56–7.52 (6H, m), 7.32-7.19 (9H, m), 6.24 (1H, s), 6.15 (1H, s), 5.85 (2H, s), 3.98 (1H, brs), 3.35 (1H, dd, J$_1$=5 Hz, J$_2$=14 Hz), 2.33 (1H, t, J=14 Hz), 1.47 (1H, dd, J$_1$=6 Hz, J$_2$=1.5 Hz)

Reference Example 100

Preparation of 1-methoxymethyl-3S-triphenylmethylamino-6,7-methylenedioxy-3,4-dihydrocarbostyril Using chloromethyl methyl ether and a corresponding starting material, the captioned compound was obtained in the same manner as in Reference Example 24.

NMR (270 MHz, CDCl$_3$) δppm: 7.50–7.54 (6H, m), 7.15–7.29 (9H, m), 6.82 (1H, s), 6.13 (1H, s), 5.86 (2H, s), 5.61 (1H, d, J=11 Hz), 4.84 (1H, d, J=11 Hz), 3.39 (1H, dd, J$_1$=5 Hz, J$_2$=15 Hz), 3.3 1 (3H, s), 2.30 (1H, t, J=15 Hz), 1.48 (1H, dd, J=5.15 Hz)

Reference Example 101

Preparation of 1-hexyloxymethyl-6,7-methylenedioxy-3S-triphenylmethylamino-3,4dihydrocarbostyril Using chloromethyl hexyl ether and a corresponding starting material, the captioned compound was obtained in the same manner as in Reference Example 24.

NMR (270 MHz, CDCl$_3$) δppm: 7.53-7.50 (6H, m), 7.29-7.19 (9H, m), 6.90 (1H, s), 6.13 (1H, s), 5.87 (2H, s), 5.70 (1H, d, J=11 Hz), 4.86 (1H, d, J=11 Hz), 4.10 (1H, brs), 3.51-3.34 (3H, m), 2.28 (1H, t, J=14 Hz), 1.56-1.27 (9H, m), 0.87 (3H, t, J=5 Hz)

Reference Example 102

Preparation of 1-methoxyethoxymethyl-3S-triphenylmethylamino-6,7-methylenedioxy-3,4-dihydrocarbostyril Using iodomethyl methoxyethyl ether and a corresponding starting material, the captioned compound was obtained in the same manner as in Reference Example 24.

NMR(270 MHz, CDCl$_3$) δppm:7.49–7.53(6H, m), 7.18–7.31 (9H, m), 6.92 (1H, s), 6.14 (1H, s), 5.87 (1H, d, J=1 Hz), 5.86 (1H, d, J=1 Hz), 5.75(1H, d,J=11 Hz), 4.91 (1H, d, J=11 Hz), 4.04 (1H, brs), 3.49–3.72 (4H, m), 3.38 (3H, s), 3.36 (1H, dd, J$_1$=5 Hz, J$_2$=15 Hz), 2.31 (1H, t, J=15 Hz), 1.49 (1H, dd, J$_1$=5 Hz, J$_2$=15 Hz)

Reference Example 103

Preparation of 1-methoxymethoxyethyl-3S-triphenylmethylamino-6,7-methylenedioxy-3,4-dihydrocarbostyril Using iodomethyl methoxymethyl ether and a corresponding starting material, the captioned compound was obtained in the same manner as in Reference Example 24.

NMR (270 MHz, CDCl$_3$) δppm: 7.48–7.55 (6H, m), 7.18–7.36 (9H, m), 6.75 (1H, s), 6.12 (1H, s), 5.88 (1H, d, J=2 Hz), 5.86 (1H, d, J=2 Hz), 4.54–4.62 (2H, m), 4.16–4.21 (1H, m), 3.93–4.03 (1H, m), 3.70–3.77 (2H, m), 3.31 (1 H, dd, J$_1$15 Hz, J$_2$=15 Hz), 3.26 (3H, s), 2.27 (1H, t, J=15 Hz), 1.35 (1H, dd, J$_1$=5 Hz, J$_2$=15 Hz)

Reference Example 104

Preparation of 1-(4-methoxybenzyl)-3S-triphenylmethylamino-6,7-methylenedioxy-3,4-dihydrocarbostyril Using 4-methoxybenzyl chloride and a corresponding starting material, the captioned compound was obtained in the same manner as in Reference Example 24.

NMR(270 MHz, CDCl$_3$) δppm: 7.53–7.56 (6H, m), 7.20–7.33 (9H, m), 7.04–7.08 (2H, m), 6.80–6.85 (2H, m), 6.38 (1H, s), 6.13 (1H, s), 5.82 (1H, d, J=2 Hz), 5.79 (1H, d, J=2 Hz), 4.22 (1H, brs), 3.79 (3H, s), 3.45 (1H, dd, J$_1$=5 Hz, J$_2$=15 Hz), 2.32 (1H, t, J=15 Hz), 1.46 (1H, dd, J$_1$=5 Hz, J$_2$=15 Hz)

Reference Example 105

Preparation of 1-ethoxyethyl-6,7-methylenedioxy-3S-triphenylmethylamino-3,4-dihydrocarbostyril Using iodoethyl ethyl ether and a corresponding starting material, the captioned compound was obtained in the same manner as in Reference Example 24.

NMR(270 MHz, CDCl$_3$) δppm: 7.52-7.48 (6H, m), 7.31-7.18 (9H, m), 6.81 (1H, s), 6.11 (1H, s), 5.87 (2H, d, J=3 Hz), 4.18-4.09 (2H, m) 3.92-3.84 (1H, m) 3.62 (2H, dd, J$_1$ =5 Hz, J=7 Hz), 3.54-3.43 (2H, m), 3.30 (1H, dd, J$_1$=5 J$_2$=14 Hz), 2.27 (1H, t, J=14 Hz), 1.37 (1H, dd, J$_1$=5 Hz, J$_2$=15 Hz), 1.16 (3H, t, J=7 Hz)

Reference Example 106

Preparation of 1-hexyl-6,7-methylenedioxy-3S-triphenylmethylamino-3,4-dihydrocarbostyril Using iodohexane and a corresponding starting material, the captioned compound was obtained in the same manner as in Reference Example 24.

NMR (270 MHz, CDCl$_3$) δppm: 7.57-7.48 (6H, m), 7.31-7.18 (9H, m), 6.49 (1H, s), 6.11 (1H, s), 5.87 (2H, d, J=4 Hz), 4.27 (1H, brs), 3.99-3.90 (1H, m), 3.82-3.74 (1H, m), 3.27 (1H, dd, J$_1$=5 Hz, J$_2$=14 Hz), 2.22 (1H, t, J=15 Hz), 1.56-1.50 (2H, m), 1.36-1.24 (7H, m), 0.88 (3H, t, J=6 Hz)

Reference Example 107

Preparation of 1-phenethyl-3S-triphenylmethylamino-6,7-methylenedioxy-3,4-dihydrocarbostyril Using phenethyl iodide and a corresponding starting material, the captioned compound was obtained in the same manner as in Reference Example 24.

NMR (270 MHz, CDCl$_3$) δppm: 7.49-7.53 (6H, m), 7.19-7.32 (14H, m), 6.44 (1H, s), 6.12 (1H, s), 5.89 (1H, d, J=1 Hz), 5.87 (1H, d, J=1 Hz), 4.11-4.22 (2H, m), 3.94-4.05 (1H, m), 3.27 (1H, dd, J$_1$=5 Hz, J$_2$=15 Hz), 2.83-2.92 2H, m), 2.16 (1H, t, J=15 Hz), 1.32 (1H, dd, J$_1$=5 Hz, J$_2$=15 Hz)

Reference Example 108

Preparation of 1-ethoxymethyl-6,7-methylenedioxy-3S-triphenylmethylamino-3,4-dihydrocarbostyril Using chloromethyl ethyl ether and a corresponding starting material, the captioned compound was obtained in the same manner as in Reference Example 24.

NMR (270 MHz, CDCl$_3$) δppm: 7.53-7.49 (6H, m), 7.31-7.18 (9H, m), 6.90 (1H, s), 6.13 (1H, s), 5.87 (2H, dd, J$_1$=1 Hz, J$_2$=3 Hz), 5.71 (1H, d, J=11 Hz), 4.85 (1H, d, J=11 Hz), 4.10 (1H, brs) 3 53 (2H qd, J$_1$=4 Hz, J$_2$=7 Hz), 3.36 (1H, dd, J$_1$=5 Hz, J$_2$=14 Hz), 2.30 (1H, t, J=15 Hz), 1.46 (1H, dd, J$_1$=5 Hz, J$_2$=15 Hz), 1.20 (3H, t, J=7 Hz)

Reference Example 109

Preparation of 3S-amino-6,7-methylenedioxy-1-propyl-3,4-dihydrocarbostyril

Using propyl iodide and a corresponding starting material, the captioned compound was obtained in the same manner as in Reference Example 88.

NMR (270 MHz, CDCl$_3$) δppm: 6.68 (1H, s), 6.57 (1H, s), 5.94 (2H, s), 3.70–4.00 (2H, m), 3.62 (1H, dd, J$_1$=6 Hz, J$_2$=14 Hz), 2.99 (1H, dd, J$_1$=6 Hz, J$_2$=14 Hz), 2.84 (1H, t, J=14 Hz), 1.50-1.90 (2H, m), 0.94 (3H, t, J=7 Hz)

Reference Example 110

Preparation of 1-carbamoylmethyl-6,7-methylenedioxy-3S-triphenylmethylamino-3,4-dihydrocarbostyril Using 2-iodoacetamide and a corresponding starting material, the captioned compound was obtained in the same manner as in Reference Example 24.

NMR (270 MHz, CDCl$_3$) δppm: 7.52 (6H, d, J=7 Hz), 7.10-7.40 (9H, m), 6.64 (1H, s), 6.19 (1H, s), 5.96 (1H, brs), 5.88 (1H, s), 5.86 (1H, s), 5.36 (1H, brs), 4.78 (1H, d, J=16 Hz), 4.10 (1H, d, J=16 Hz), 3.82 (1H, brs), 3.39 (1H, dd, J$_1$=5 Hz, J$_2$=14 Hz), 2.32 (1H, t, J=14 Hz), 1.65 (1H, dd, J$_1$=5 Hz, J$_2$=15 Hz)

Reference Example 111

Preparation of 1-t-butoxycarbonylmethyl-6,7-methylenedioxy-3S-triphenylmethylamino-3,4-dihydrocarbostyril.

Using t-butyl bromoacetate and a corresponding starting material, the captioned compound was obtained in the same manner as in Reference Example 24.

NMR (270 MHz, CDCl$_3$) δppm: 7.51 (6H, d, J=7 Hz), 7.10-7.40 (9H, m), 6.29 (1H, s), 6.14 (1H, s), 5.87 (1H, s), 5.85 (1H, s), 4.62 (1H, d, J=17 Hz), 4.35 (1H, d, J=17 Hz), 4.10 (1H, s), 3.35 (1H, dd, J$_1$=5 Hz, J$_2$=14 Hz), 2.32 (1H, t, J=14 Hz), 1.42 (9H, s), 1.30-1.60 (1H, m)

Reference Example 112

Preparation of 3S-amino-1-methyl-6,7-methylenedioxy-3,4-dihydrocarbostyril

Using methyl iodide and a corresponding starting material, the captioned compound was obtained in the same manner as in Reference Example 88.

NMR(270 MHz, CDCl$_3$) δppm: 6.68 (1H, s), 6.57 (1H, s), 5.95 (2H, s), 3.49 (1H, dd, J$_1$=6 Hz, J$_2$=13 Hz), 3.34 (3H, s), 2.80–3.00 (1H, m), 2.75 (1H, t, J=13 Hz)

Reference Example 113

Preparation of 3S-amino-1-ethyl-6,7-methylenedioxy-3,4-dihydrocarbostyril

Using ethyl iodide and a corresponding starting material, the captioned compound was obtained in the same manner as in Reference Example 88.

NMR (270 MHz, CDCl$_3$) δppm: 6.67 (1H, s), 6.60 (1H, s), 5.94 (2H, s), 3.80–4.10 (2H, m), 3.48 (1H, dd, J$_1$=6 Hz, J$_2$=14 Hz), 2. 91 (1H, dd, J$_1$=7 Hz, J$_2$=14 Hz), 2.72 (1H, t, J=14 Hz) 1.26 (3H, t, J=7 Hz)

Example 1

Preparation of 3S-[4-(N-hydroxyamino)-2R-isobutylsuccinyl]amino-3,4-dihydrocarbostyril 240 mg of 3S-[4-(N-benzyloxyamino)-2R-isobutylsuccinyl]amino-3,4-dihydrocarbostyril was dissolved in 10.8 ml of ethanol, and 1.2 ml of cyclohexene and 60 m$_9$ of 10% palladium-carbon were added, and the mixture was stirred for 20 minutes in reflux. Filtering off the catalyst, the filtrate was concentrated in vacuo. The residue was purified by column chromatography (silica gel 20 g, chloroform/methanol=20/1 v/v), and the captioned compound was obtained in a white solid form. Yield: 110 mg.

[α]$_D$=−49° (c=1, methanol)

NMR (270 MHz, DMSO-d$_6$) δppm: 10.38 (1H, brs), 10.20 (1H, s), 8.70 (1H, brs), 8.15 (1H, d, J=8 Hz), 7.16 (2H, t, J=7 Hz), 6.90 (2H, dd, J=16, 8 Hz), 4.44 (1H, dt, J=12, 8 Hz), 2.70–3.00 (3H, m), 2.17 (1H, dd, J=14, 6 Hz), 2.04 (1H, dd, J=14, 7 Hz), 1.40–1. 70 (2H, m), 1.00–1.30 (1H. m), 0. 86 (6H, dd, J=12, 6 Hz)

Example 2

Using a corresponding starting material, 3S-[4-(N-hydroxyamino)-2R-isobutylsuccinyl]amino-7-methoxy-3,4-dihydrocarbostyril was obtained in the same manner as in Example 1.

NMR (270 MHz, DMSO-d$_6$) δppm: 10.36 (1H, brs), 10.14 (1H, s), 8.70 (1H, s), 8.13 (1H, d, J=8 Hz), 7.08 (1H, d, J=8 Hz), 6.51 (1H, dd, J=8, 2 Hz), 6.46 (1H, d, J=2 Hz), 4.42 (1H, dt, J=13, 8 Hz), 3.70 (3H, s), 2.65—3.00 (3H, m), 2.17 (1H, dd, J=14, 6 Hz), 2.01 (1H, dd, J=14, 7 Hz), 1.20–1.70 (2H, m), 1.00–1.20 (1H, m), 0.86 (6H, dd, J=13, 6 Hz)

Example 3

Using a corresponding starting material, 3S-[4-(N-hydroxyamino)-2R-isobutylsuccinyl]amino-1-methoxy-3,4dihydrocarbostyril was obtained in the same manner as in Example 1.

$[\alpha]_D$=−19° (c=1, methanol)

NMR (270 MHz, DMSO-$d_6$) δppm: 10.40 (1H, brs 8.71 (1H, brs), 8.36 (IH, d, J=8 Hz), 7.31 (2H, dd, J=16, 8 Hz), 7.16 (1H, d, J=8 Hz), 7.07 (1H, t, J=8 Hz), 4.60 (1H, dt, J=13, 8 Hz), 3.82 (3H, s), 2.85–3.15 (2H, m), 2.70–2.85 (1H, m), 2.18 (1H, dd, J=14, 6 Hz), 2.01 (1H, dd, J=14, 8 Hz), 1.40–1.75 (2H. m), 1.00–1.15 (1H, m), 0.87 (6H, dd, J=13, 6 Hz)

Example 4

Preparation of 3S-[4-(N-hydroxyamino)-2R-isobutyl-3S-acetylthiomethylsuccinyl]amino-3,4-dihydrocarbostyril 330 mg of 3S-(4-hydroxy-2R-isobutyl-3S-acetylthiomethylsuccinyl)amino-3,4-dihydrocarbostyril was dissolved in a mixed solvent of 1 ml of dimethyl formamide and 3.5 ml of dichloromethane, and cooled in an ice bath, and 110 mg of 1-hydroxybenzotriazole, 107 μl of N-methylmorpholine, and 186 mg of 1-ethyl-3-(3-dimethylaminopropyl)carbodiimide hydrochloride were added, and the mixture was further stirred for 1 hour in an ice bath, and a solution of 57 mg of hydroxylamine hydrochloride and 89 μl of N-methylmorpholine dissolved in 0.5 ml of dimethyl formamide was added. After stirring for 1 hour in an ice bath, the reaction solution was concentrated in vacuo. The residue was dissolved in 10 ml of butanol, and washed in 5 ml of water, and evaporated in vacuum. The residue was purified by column chromatography (silica gel 20 g, chloroform/methanol=20/1 v/v), and the captioned compound was obtained in a white solid form. Yield: 45 mg.

$[\alpha]_D$=−49° ( c=1, methanol)

NMR (270 MHz, DMSO-$d_6$) δppm: 10.61 (1H, s), 10.23 (1H, s), 8.92 (IH, s), 8.51 (1H, d, J=8 Hz), 7.10–7.20 (2H, m), 6.91 (2H, dd, J=15, 8 Hz), 4.51 (1H, q, J=9 Hz), 2.80–3.20 (4H, m), 1.40–1.60 (2H, m), 0.80–1.00 (1H, m), 0.83 (6H, dd, J=12, 6 Hz)

Example 5

Preparation of 3S-[4-(N-hydroxyamino)-2R-isobutyl-3S-mercaptomethylsuccinyl]amino-3,4-dihydrocarbostyril 14 mg of 3S-[4-(N-hydroxyamino)-2R-isobutyl-3S-acetylthiomethylsuccinyl]amino-3,4-dhydrocarbostyril was dissolved in 1 ml of methanol, and 200 μl of methylamine 40%-methanol solution was dripped. After stirring for 1 hour at room temperature, precipitating crystals were filtered, and the cap%ioned compound was obtained in a white solid form. Yield: 4 mg.

NMR (270 MHz, DMSO-$d_6$) δppm: 10.59 (1H, s), 10.11 (1H, s), 8.95 (1H, s), 8.54 (1H: d, J=8 Hz), 7.05–7.25 (2H, m), 6.82 (2H, dd, J=16, 8 Hz), 4.40–4.60 (1H, m), 2.60–3.30 (4H, m) 1.45–1.70 (2H, m), 0.80–1.10 ($_1$H, m), 0.84 (6H, dd, J=12, 6 Hz)

Example 6

Using a corresponding starting material, 3S-[4-(N-hydroxyamino)-2R-isobutyl-3S-(2-thienylthiomethyl)succinyl]amino-3,4-dihydrocarbostyril was obtained in the same manner as in Example 4.

$[\alpha]_D$=−52° (c=1, methanol)

NMR (270 MHz, DMSO-$d_6$) δppm: 10.70 (1H, s), 10.22 (1, s), 8.95 (1H, s), 8.47 (1H, d, J=7 Hz), 7.60 (1H, d, J=4 Hz), 7.10–7.20 (3H, m), 7.05 (1H, dd, J=3.5 Hz), 6.90 (2H, dd, J=17.8 Hz), 4.37 ([H, dt, J=14.7 Hz), 2.80–3.20 (4H, m), 1.40–1.60 (2H, m), 0.80–1.00 (1H, m), 0.82 (6H, dd, J=10.6 Hz)

Example 7

Preparation of 3S-[4-(N-hydroxyamino)-2R-isobutyl-3(R or s)-phthalimidomethylsuccinyl]amino-3,4-dihydrocarbostyril To a 20 ml suspension of dimethyl formamide of 320 mg of 3S-[4-(N-benzyloxyamino)-2R-isobutyl-3(R or S)-phthalimidomethylsuccinyl]amino-3,4-dihydrocarbostyril, 200 mg of 10% palladium-carbon was added, and hydrogen gas was introduced in vacuo, and the mixture was stirred for 2 days. The catalyst was filtered away from the reaction solution by using celite, and the liltrate was concentrated in vacuo. Adding 200 ml of methanol to the crystalline residue, it was heated and dissolved, and the remaining catalyst was filtered off by using celite. The filtrate was concentrated in vacuo, and the precipitating sediment was filtered and dried, and the captioned compound was obtained in a white solid form. Yield: 172 mg.

NMR (270 MHz, DMSO-$d_6$) δppm: 10.47 (1H, s), 10.12 (1H, s), 8.68 (1H, s), 8.50 (1H, d, J=8 Hz), 7.88-7.80 (4H, m), 7.16 (2H, t, J=8 Hz), 6.90 (2H, dd, $J_1$=8 Hz, $J_2$=13 Hz), 4.46-4.43 (1H, m), 3.90-3.85 (1H, m), 3.50-3.43 (1H, m), 2.97 (2H, d, J=11Hz), 2.63-2.59 (2H, m), 1.62-1.53 (2H, m), 0.95-0.81 (7H, m)

Example 8

Preparation of 3S-[4-(N-benzoyloxyamino)-2R-isobutylsuccinyl]amino-3,4-dihydrocarbostyril 180 mg of 3S-[4-(N-hydroxyamino)-2R-isobutylsuccinyl]amino-3,4-dihydrocarbostyril was dissolved in a mixed solvent of 2 ml of dimethyl formamide and 2 ml of dichloromethane, cooled in a water bath, 220 μl of pyridine and 88 μl of benzoyl chloride were added, and the mixture was stirred for 30 minutes in an ice bath. The reaction solution was concentrated in vacuo, 30 ml of chloroform was added, and it was washed by 10 ml of 1N hydrochloric acid and 10 ml of water, and dried over magnesium sulfate, and evaporated in vacuum. To the residue, 10 ml of diethyl ether was added, precipitating crystals were filtered, and the captioned compound was obtained in a white solid form. Yield: 110 mg.

NMR (270 MHz, CDCl$_3$) δppm: 10.48 (1H, brs), 8.08 (2H, d, J=7 Hz), 7.74 (1H, s), 7.62 (1H, t, J=7 Hz), 7.46 (2H, t, J=7 Hz), 7.10–7.25 (2H, m), 7.01 (2H, t, J=7 Hz), 6.74 (1H, d, J=7 Hz), 4.55 (1H, dt, J=14, 7 Hz), 3.40 (1H, dd, J=15, 6 Hz) 2.65–3.30 (3H, m), 2.49 (1H, dd, J=15, 3 Hz), 1.00–1.80 (3H, m), 0.96 (6H, dd, J=12, 6 Hz)

Example 9

Preparation of 3-[4-(N-hydroxyamino)-2-piperonylsuccinyl]amino-3,4-dihydrocarbostyril To 10 ml of methanol solution of 49 mg of hydroxylamine hydrochloride, while stirring in ice-cooling, 10 ml of methanol solution of 66 mg of potassium hydroxide was added and stirred for 5 minutes, and 3 ml solution of dimethyl formamide of 100 mg of 3-(4-ethoxy-2-piperonylsuccinyl) amino-3,4-dihydrocarbostyril was added, and stirred overnight at room temperature. The reaction solution was neutralized with acetic acid, the insoluble matter was filtered off, and the filtrate was concentrated in vacuo. The residue was extracted with 20 ml of n-butanol. After washing the organic layer three times by water, it was concentrated in vacuo. The residue was purified by silica gel preparation (chloroform: methanol=7:1), and the captioned compound was obtained. Yield: 4.47 mg.

NMR (270 MHz, DMSO-$d_6$) δppm: 10–40 (1H, brs), 10.29 (1H, brs), 8.70 (1H, brs), 8.17 (1H, d, J=8 Hz), 7.17 (2H, n, J=7 Hz), 6.96-6.61 (5H, m), 5.97 (2H, s), 4.51-4.42 (1H, m), 3.10-2.62 (4H, m), 2.49-1.93 (3H, m)

Example 10

Preparation of 3S-[4-(N-benzyloxyamino)-2R-isobutyl-3 (R or S)-phthalimidomethylsuccinyl]amino-3,4-dihydrocarbostyril 990 mg of 3S-(4-tert-butoxy-2R-isobutyl-3 (R or S)-phthalimidomethylsuccinyl)amino-3,4-dihydrocarbostyril was dissolved in 5 ml of dichloromethane, and 10 ml of 4N hydrogen chloride/dioxane was added, and let stand at room temperature for 2 hours. The reaction solution was concentrated in vacuo, and the residue was dissolved in 50 ml of ethyl acetate. The ethyl acetate layer was washed by saturated brine (2 times), and dried by sodium sulfate anhydride, and concentrated in vacuo. The obtained residue was dried and powdered (660 mg). To 10 ml solution of tetrahydrofurane of 660 mg of the obtained powder, N-methylmorpholine was added by 190 µl while cooling and stirring in ice-salt, and 240 µl of isobutyl chloroformate was added and stirred for 5 minutes. In succession, adding 10 ml of dimethyl formamide of 573 mg of benzyloxyamine, the solution was stirred for 1 hour at room temperature while maintaining at pH 8. The reaction solution was concentrated in vacuo, and 20 ml of water was added to the residue to solidify and filter. The crude product was washed with ethyl acetate and diethyl ether, and the captioned compound was obtained in a white solid form. Yield: 330 mg.

NMR (270 MHz, DMSO-$d_6$) δppm: 11.18 (1H, s), 10.24 (1H, s), 8.57 (1H, d, J=8 Hz), 7.92-7.84 (4H, m), 7.32-7.15 (7H, m), 6.97-6.91 (2H, m), 4.67-4.37 (3H, m), 4.00-3.85 (1H, m), 3.60-3.50 (1H, m), 3.03 (2H, d, J=10 Hz), 2.72-2.69 (2H, m), 1.59-1.54 (2H, m), 0.98-0.83(7H, m)

Example 11

Preparation of 3S-[4-(N-benzyloxyamino)-2R-isobutylsuccinyl]amino-3,4-dihydrocarbostyril 500 mg of 3S-(3-carboxy-2R-isobutylpropionyl)amino-3,4-dihydrocarbostyril was dissolved in 5 ml of dimethyl formamide, and 329 mg of O-benzylhydroxylamine was added, and cooled in an ice bath, and 213 mg of 1-hydroxybenzotriazole, 259 µl of N-methylmorpholine, and 368 mg of 1-ethyl-3-(3-dimethylaminopropyl)carbodiimide hydrochloride were added, and the mixture was stirred for 3 hours in an ice bath and 15 hours at room temperature. The reaction solution was concentrated in vacuo, and 50 ml of ethyl acetate was added to the residue, and it was washed by 10 ml of water, 10 ml of 1N hydrochloric acid, satura%ed aqueous solution of sodium hydrogencarbonate (10 ml×3 times), and 10 ml of brine, and dried over magnesium sulfate, and evaporated in vacuum. The residue was purified by column chromatography (silica gel 50 g, chloroform/ methanol=40/v/v), and the captioned compound was obtained in a white solid form. Yield: 300 mg.

NMR (270 MHz, CDCl$_3$) δppm: 8.57 (1H, brs), 7.79 (1H, brs), 7.38 (5H, s), 7.38 (2H, dd, J=14.7 Hz), 7.01 (1H, t, J=7 Hz), 6.78 (1H, d, J=7 Hz), 4.90 (2H, s), 4.45–4.60 (1H, m), 3.35–3.50 (1H, m), 2.80–2.98 (1H, m), 2.80 (1H, t, J=14 Hz), 2.20–2.50 (2H, m), 1.20–1.40 (3H, m), 0.94 (6H, dd, J=16, 6 Hz)

Example 12

Using a corresponding starting material, 3S-[4-(N-benzyloxyamino)-2R-isobutylsuccinyl]amino-7-methoxy-3,4-dihydrocarbostyril was obtained in the same manner as in Example 11.

NMR (270 MHz, CDCl$_3$) δppm: 8.90 (1H, s), 8.49 (1H, s), 7.34 (5H, s), 7.05–7.15 (1H, m), 6.99 (1H, d, J=8 Hz), 6.51 (1H, dd, J=8, 2 Hz), 6.41 (1H, s), 4.88 (2H, s), 4.40–4.55 (1H, m), 3.73 (3H, s), 3.25–3.45 (1H, m), 2.90–3.10 (1H, m), 2.66 (1H, t, J=14 Hz), 2.15–2.50 (2H, m), 1.50–1.80 (2H, m), 1.20–1.40 (1H, m), 0.94 (6H, dd, J=19, 6 Hz)

Example 13

Using a corresponding starting material, 3S-[4-(N-benzyloxyamino)-2R- isobutylsuccinyl]amino-1-methoxy-3,4-dihydrocarbostyril was obtained in the same manner as in Example 11.

NMR (270 MHz, CDCl$_3$) δppm: 8.69 (1H, s), 7.37 (5H, s), 7.15–7.35 (3H, m), 7.07 (1H, t, J=7 Hz), 6.67 ([H, d, J=6 Hz), 4.90 (2H, s), 4.40–4.60 (1H, m), 3.92 (3H, s), 3.25–3.45 (1H, m), 2.75–2.95 (2H, m), 2.20–2.50 (2H, m), 1.50–1.80 (2H, m), 1.20–1.35 (2H, m), 0.93 (6H, dd, J=16, 6Hz)

Example 14

Preparation of 1-hexyloxy-3S-[4-(N-hydroxyamino)-2R-isobutyl-3S-methylsuccinyl]amino-3,4-dihydrocarbostyril To a 15 ml solution of tetrahydrofurane of 400 mg of 3S-[4-(N-benzyloxyamino)-2R-isobutyl-3S-methylsuccinyl]amino-1-hexyloxy-3,4-dihydrocarbostyril, 150 mg of 10% palladiumcarbon and 1.0 ml of cyclohexene were added and stirred for 30 minutes while refluxing. The catalyst was filtered off from the reaction solution by using celite, and the filtrate was concentrated in vacuo. The obtained residue was purified by silica gel column chromatography (eluted in 3% methanol/chloroform), and the captioned compound was obtained. Yield: 250 mg.

NMR (270 MHz, DMSO-$d_6$) δppm: 10.48 (1H, s), 8.76 (1H, s), 8.55 (1H, d, J=8 Hz), 7.35-7.27 (2H, m), 7.14 ([H, d, J=7 Hz), 7.06 (1H, t, J=7 Hz), 4.63-4.58 (1H, m), 4.00 (1H, d, J=7 Hz), 3.97 (1H, d, J=7 Hz), 3.06 ([H, t, J=13 Hz), 2.94 (1H, dd, J$_1$=7 Hz, J$_2$=16 Hz), 2.51-2.45 (1H, m), 2.20-2.13 (1H, m), 1.71-1.27 (10H, m), 0.97 (3H, d, J=7 Hz), 0.92-0.80 (10H, m)

Example 15

Preparation of 1-(4-cyanobenzyl)-3S-[4-(N-hydroxyamino)-2R-isobutyl-3S-methylsuccinyl]amino-3,4-dihydrocarbostyril After conducting a reaction between the compound of Reference Example 24 and a corresponding staring material, the captioned compound was obtained in the same manner as in Example 16.

NMR (270MHz, DMSO-d$_6$) δppm: 10.49 (1H, s), 8.77 (1H, s), 8.54 (1H, d, J=9 Hz), 7.80 (2H, d, J=8 Hz), 7.43 (2H, d, J=8 Hz), 7.29 (1H, d, J=7 Hz), 7.17 (1H, t, J=8 Hz), 7.00 (1H, t, J=7 Hz), 6.90 (1H, d, J=8 Hz), 5.30 (1H, d, J=17 Hz), 5.19 ([H, d, J=17 Hz), 4.75-4.70 (1H, m), 3.15 (1H, t, J=15 Hz), 3.00 (1H, dd, J$_1$=6 Hz, J$_2$=15 Hz), 2.55-2.49 (1H, m), 2.21-2.15 (1H, m), 2.58-2.43 (2H, m), 0.99 (3H, d, J=7 Hz), 1.01-0.79 (1H, m), 0.83 (6H, dd, J$_1$=7 Hz, J$_2$=18 Hz)

Example 16

Preparation of 1-(5-chloro-2-thienylmethyl)-3S-[4-(N-hydroxyamino)-2R-isobutyl-3S-methylsuccinyl]amino-3,4-dihydrocarbostyril To 920 mg of 3S-(4-t-butoxy-2R-isobutyl-3S-methyl-succinyl)amino-1-(5-chloro-2-thienylmethyl)-3,4-dihydrocarbostyril obtained in the same manner as in Reference Example 22 by using a corresponding starting material, 5 ml of trifluoroacetic acid was added to dissolve, and let stand at room temperature for 90 minutes. The reaction solution was concentrated in vacuo, and the obtained oily residue was extracted in 30 ml of ethyl acetate. The ethyl acetate layer was washed three times in saturated brine, dried over magnesium sulfate anhydride, and concentrated in vacuo. The obtained residue was dried (790 mg). To a 10 ml solution of tetrahydrofurane of 390 mg of the obtained compound, while cooling and stirring in ice/salt, 126 μl of N-methylmorpholine and 111 μl of isobutyl chloroformate were added, and the mixture was stirred for 15 minutes. To the reaction solution, 195 mg of O-(t-butyldimethylsilyl)hydroxyamine was added, and stirred overnight at room temperature. The insoluble matter was filtered off from the reaction solution, and 4 ml of acetic acid and 4 ml of water were added to the filtrate, and stirred for 3 hours at room temperature. The reaction solution was concentrated in vacuo, and the obtained residue was dissolved and extracted in 50 ml of ethyl acetate. The ethyl acetate layer was washed three times in saturated brine and two times in water, and concentrated in vacuo. The obtained residue was purified by silica gel column chromatography (eluted in 3% methanol/chloroform), and the captioned compound was obtained in a white solid form. Yield: 170 mg.

NMR (270 MHz, DMSO-d$_6$) δppm: 10.48 (1H, s), 8.76 (1H, s), 8.52 (1H, d, J=8 Hz), 7.29-7.25 (3H, m), 7.06-7.00 (2H, m), 6.94 (1H, d, J=4 Hz), 5.23 (2H, d, J=3 Hz), 4.62-4.57 (1H, m), 3.04 (1H, t. J=14 Hz), 2.93 (1H, dd, J$_1$=6 Hz, J$_2$=15 Hz), 2.54-2.47 (1H, m), 2.20-2.14 (1H, m), 1.60-1.42 (2H, m), 0.98 (3H, d, J=7 Hz), 1.00-0.80 (1H, m), 0.85 (6H, dd, J$_1$=6 Hz, J$_2$=17 Hz)

Example 17

Preparation of 3S- [4-(N-hydroxyamino)-2R-isobutyl-3S-methylsuccinyl]amino-3,4-dihydrocarbostyril Using a corresponding starting material, the captioned compound was obtained in the same manner as in Example 14.

NMR (270 MHz, DMSO-d$_6$) δppm: 10.48 (1H, s), 10.18 (1H, s), 8.75 (1H, s), 8.37 (1H, d, J=8 Hz), 7.20-7.13 (2H, m), 6.95-6.86 (2H, m), 4.51-4.46 (1H, m), 2.99-2.93 (2H, m), 2.51-2.44 (1H, m), 2.20-2.14 (1H, m), 1.60-1.40 (2H, m), 0.97 (3H, d, J=7 Hz), 0.98-0.80 (1H, m), 0.84 (6H, dd, J$_1$=6 Hz, J$_2$=15 Hz)

Example 18

Preparation of 1-hydroxy-3S-[4-(N-hydroxyamino)-2R-isobuty-3S-methylsuccinyl]amino-3,4-dihydrocarbostyril After conducting a reaction between the compound of Reference Example 26 and a corresponding starting material, the captioned compound was obtained in the same manner as in Example 14.

NMR (270 MHz, DMSO-d$_6$) δppm: 10.49 (2H, bs), 8.76 ([H, s), 8.54 (1H, d, J=8 Hz), 7.32-7.20 (3H, m), 7.01 (1H, td, J$_1$=2 Hz, J$_2$=7 Hz), 4.64-4.54 (1H, m), 3.06 (1H, t, J=15 Hz), 2.93 (1H, dd, J$_1$=7 Hz, J$_2$=16 Hz), 2.51-2.45 (1H, m), 2.20-2.14 (1H, m), 1.65-1.42 (2H, m), 0.98 (3H, d, J=7 Hz), 1.00-0.80 (1H, m), 0.85 (6H, dd, J$_1$=7 Hz, J$_2$=26 Hz)

Example 19

Preparation of 3S-[4-(N-hydroxyamino)-2R-isobutyl-3S-methylsuccinyl]-1-methoxy-3,4-dihydrocarbostyril Using a corresponding starting material, the captioned compound was obtained in the same manner as in Example 14.

NMR (270 MHz, DMSO-d$_6$)δ ppm: δ10.48 (1H, s), 8.76 (1H, s), 8.55 (1H, d, J=8 Hz), 7.36-7.28 (2H, m), 7.16 (1H, d, J=8 Hz), 7.07 (1H, t, J=7 Hz), 4.66-4.61 (1H, m), 3.83 (3H, s), 3.06-2.93 (2H, m), 2.52-2.44 (1H, m), 2.20-2.13 (1H, m), 1.57–2.42 (2H, m), 0.97 (3H, d, J=7 Hz), 0.98-0.81 (1H, m), 0.84 (6H, dd, J$_1$=6 Hz, J$_2$=14 Hz)

Example 20

Preparation of 7-chloro-1-ethoxy-3S-[4-(N-hydroxyamino)-2R-isobutyl-3S-methylsuccinyl]amino-3,4-dihydrocarbostyril After conducting a reaction between the compound of Reference Example 27 and a corresponding starting material, the captioned compound was obtained in the same manner as in Example 14.

NMR(270 MHz, DMSO-d$_6$) δppm: 10.48 (2H, s), 8.77 (2H, s), 8.58 (1H, d, J=8 Hz), 7.32 (1H, d, J=8 Hz), 7.13-7.09 (2H, m), 4.63-4.59 (1H, m), 4.06 (2H, q, J=7 Hz), 3.04-2.95 (2H, m), 2.51-2.43 (1H, m), 2.19-2.12 (1H, m), 1.69-1.41 (2H, m), 2.28 (3H, t, J=7 Hz), 0.97 (3H, d, J=7 Hz), 0.98-0.80 (1H, m), 0.83 (6H, dd, J$_1$=7 Hz, J$_2$=22 Hz)

Example 21

Preparation of 3S- [4-(N-hydroxyamino)-2R-isobutylsuccinyl ]amino-1-isobutoxy-3,4-dihydrocarbostyril After conducting a reaction between the compound of Reference Example 28 and a corresponding starting material, the captioned compound was obtained in the same manner as in Example 1.

NMR (270 MHz, DMSO-d$_6$) δppm: 10.38 (1H, s), 8.71 (1H, s), 8.35 (1H, d, J=8 Hz), 7.25–7.40 (2H, m), 7.15 (1H, d, J=7 Hz), 7.06 (1H, n, J=7 Hz), 4.50–4.70 (1H, m), 3.78 (2H, dt, J=2 2, 7 Hz), 2.70–3.10 (3H, m), 2.17 (1H, dd, J=14, 6 Hz), 1.90–2.15 (2H, m), 1.40–1.75 (2H, m), 1.00–1.20 (1H, m), 0.99 (6H, dd, J=6, 3 Hz), 0.87 (6H, dd, J=12, 6 Hz)

Example 22

Preparation of 1-ethoxy-3S-[4-(N-hydroxyamino)-2R-isobutyl-3S-methylsuccinyl]amino-3,4-dihydrocarbostyril After conducting a reaction between the compound of Reference Example 29 and a corresponding starting material, the captioned compound was obtained in the same manner as in Example 14.

NMR (270 MHz, DMSO-d$_6$) δppm: 10.49 (1H, s), 8.77 (1H, s), 8.57 (1H, d, J=8 Hz), 7.31 (2H, t, J=8 Hz), 7.16 ([H, d, J=8 Hz), 7.06 (1 H, t, J=8 Hz), 4.54–4.66 (1H, m), 4.05 (2H, q, J=7 Hz), 2.96–3.07 (2H, m), 2.49–2.52 (1H, m), 2.12–2.20 (1H, m), 1.40–1.58 (2H, m), 1.28 (3H, t, J=7 Hz), 0.98 (3H, d, J=7 Hz), 0.98-0.84 (1H, m), 0.84 (6H, dd, J=13, 6 Hz)

Example 23

Preparation of 3R-[4-(N-hydroxyamino)-2R-isobutylsuccinyl]amino-1-methoxy-3,4-dihydrocarbostyril Using a corresponding starting material, the captioned compound was obtained in the same manner as in Example 1.

NMR(270 MHz, DMSO-d$_6$) δppm: 10.42 (1H, s), 8.76 (1H, s), 8.51 (1H, d, J=8 Hz), 7.32 (2H, dd, J=16, 8 Hz), 7.16 (1H, d, J=8 Hz), 7.07 (1H, t, J=8 Hz), 4.58 (1H, q, J=8 Hz), 3.83 (3H, s), 2.70–3.10 (3H, m), 2.22 (1H, dd, J=15, 5 Hz), 2.02 (1H, dd, J=15, 9 Hz), 1.40–1.60 (2H, m), 0.95–1.20 (1H, m), 0.84 (6H, d, J=6 Hz)

Example 24

Preparation of 3R- [4-(N-hydroxyamino)-2R-isobutyl-3S-methylsuccinyl]amino-1-methoxy-3,4-dihydrocarbostyril Using a corresponding starting material, the captioned compound was obtained in the same manner as in Example 14.

NMR (270 MHz, DMSO-d$_6$) δppm: 10.48 (1H, s), 8.76 (1H, s), 8.61 (1H, d, J=8 Hz), 7.25–7.40 (2H, m), 7.16 (1H, d, J=8 Hz), 7.07 ([H, t, J=8 Hz), 4.66 (1H, dt, J=13, 8 Hz), 2.80–3.10 (2H, m), 2.40–2.60 (1H, m), 2.05–2.30 (1H, m), 1.30–1.60 (1H, m), 1.07 (3H, d, J=7 Hz), 0.75–1.05 (1H, m), 0.81 (6H, dd, J=6, 4 Hz)

Example 25

Preparation of 1-ethoxymethyl-3(R or S)-[4-(N-hydroxyamino)-2R-isobutylsuccinyl]amino-3,4-dihydrocarbostyril After conducting a reaction between the compound obtained by catalytic reduction treatment of the compound of Reference Example 30 and a corresponding starting material, the captioned compound (diastereomer 1:1 mixture) was obtained in the same manner as in Example 1.

NMR (270 MHz, DMSO-d$_6$) δppm: 10.40 (1H, bs) 8.76+ 8.72 (1H, s), 8.44+8.28 (1H, d, J=8 Hz), 7.29-7.26 (3H, m), 7.09-7.03 (1H, m), 5.56+5.54 (1H, d, J=11 Hz), 5.02+5.01 (1H, d, J=11 Hz), 4.53-4.48 (1H, m), 3.51 (2H, q, J=7 Hz), 3.00-2.82 (3H, m), 2.25-1.98 (2H, m), 1.70-1.45 (2H, m), 1.11 (3H, t, J=7 Hz), 1.14–1.70 (1H, m), 0.91-0.83 (6H, m)

Example 26

Preparation of 1-hexyloxymethyl-3S- [4-(N-hydroxyamino)-2R -isobutylsuccinyl]amino-3,4-dihydrocarbostyril After conducting a reaction between the compound obtained by catalytic reduction treatment of the compound of Reference Example 31 and a corresponding starting material, the captioned compound was obtained in the same manner as in Example 1.

NMR (270 MHz, DMSO-d$_6$) δppm: 10.38 (1H, s), 8.71 (1H, s), 8.28 (1H, d, J=8 Hz), 7.27 (3H, t, J=6 Hz), 7.06 (1H, td, J$_1$=2 Hz, J$_1$=8 Hz), 5.54 (1H, d, J=11 Hz), 5.02 (1H, d, J=11 Hz), 4.56-4.45 (1H, m), 3.45 (2H, t, J=6 Hz), 3.00-2.80 (3H, m), 2.18 (1H, dd, J$_1$=6 Hz, J$_2$=14 Hz), 2.02 (1H, dd, J$_1$=8 Hz, J$_2$=15 Hz), 1.75-1.55 (1H, m), 1.54-1.45 (3H, m), 1.20-1.07 (7H, m), 0.91-0.78 (9H, m)

Example 27

Preparation of 3S-[4-(N-hydroxyamino)-2R-isobutylsuccinyl]amino-1-methoxymethyl-3,4-dihydrocarbostyril After conducting a reaction between the compound obtained by catalytic reduction treatment of the compound of Reference Example 32 and a corresponding starting material, the captioned compound was obtained in the same manner as in Example 1.

NMR (270 MHz, DMSO-d$_6$) δppm: 10.39 (1H, brs), 8.71 (1H, brs), 8.29 (1H, d, J=7 Hz), 7.15-7.35 (3H, m), 7.07 (1H, t, J=7 Hz), 5.49 (1H, d, J=10 Hz), 5.00 (1H, d, J=10 Hz), 4.52 (1H, dt, J=14, 7 Hz), 3.26 (3H, s), 2.70–3.10 (3H, m), 2.18 (1H, dd, J=14, 6 Hz), 2.02 (1H, dd, J=14, 8 Hz), 1.35–1.75 (2H, m), 1.00–1.20 (1H, m), 0.88 (6H, dd, J=14, 6 Hz)

Example 28

Preparation of 1-benzyl-3S-[4-(N-hydroxyamino)-2Risobutylsuccinyl]amino-3,4-dihydrocarbostyril After conducting a reaction between the compound obtained by trifluoroacetic acid treatment of the compound of Reference Example 33 and a corresponding starting material, the captioned compound was obtained in the same manner as in Example 1.

NMR(270 MHz, DMSO-d$_6$) δppm: 10.39 (1H, s), 8.72 (1H, s), 8.31 (1H, d, J=8 Hz), 7.34-7.14 (8H, m), 6.98 (1H, t, J=8 Hz), 5.22 (1H, d, J=16 Hz), 5.10 (1H, d, J=16 Hz), 4.69-4.59 (1H, m), 3.07-2.97 (2H, m), 2.81-2.75 (1H, m), 2.20 (1H, dd, J$_1$=7 Hz, J$_2$=15 Hz), 2.03 (1H, dd, J$_1$=8 Hz, J$_2$=15 Hz), 1.65-1.45 (2H, m), 1.14-1.07 (1H, m), 0.871 (6H, dd, J$_1$=7 Hz, J$_2$=16 Hz)

Example 29

Preparation of 3S-[4-(N-hydroxyamino)-2R-isobutylsuccinyl]amino-1-(4-methoxycarbonylbenzyl)-3,4dihydrocarbostyril Using the compound obtained by trifluoroacetic acid treatment of the compound of Reference Example 34 and a corresponding starting material, the captioned compound was obtained in the same manner as in Example 1.

NMR (270 MHz, DMSO-d$_6$) δppm: 10.39 (1H, s), 8.72 (1H, s), 8.33 (1H, d, J=7 Hz), 7.91 (2H, d, J=8 Hz), 7.37 (2H, d, J=8 Hz), 7.27 (1H, d, J=7 Hz), 7.16 (1H, t, J=7 Hz), 7.00 (1H, t, J=7 Hz), 6.91 (1H, d, J=8 Hz), 5.30 (1H, d, J=17 Hz), 5.17 (1H, d, J=17 Hz), 4.73-4.63 (1H, m), 3.83 (3H, s), 3.09-2.99 (2H, m), 2.88-2.73 (1H, m), 2.20 (1H, dd, J$_1$=7 Hz, J$_2$=15 Hz), 2.03 (1H, dd, J$_1$=8 Hz, J$_2$=15 Hz), 1.65-1.46 (2H, m), 1.13-1.07 (1H, m), 0.87 (6H, dd, J$_1$=6 Hz, J$_2$=15 Hz)

Example 30

Preparation of 1-(4-carboxybenzyl)-3(R or S)-[4-(N-hydroxyamino)-2R-isobutylsuccinyl]amino-3,4-dihydrocarbostyril To a mixed solution of 5 ml of methanol and 5 ml of tetrahydrofurane of 200 mg of 3S-[4-(N-benzyloxyamino)-2R-isobutylsuccinyl]amino-1-(4-methoxycarbonylbenzyl)-

3,4-dihydrocarbostyril, 2.0 ml of 1N sodium hydroxide was added at room temperature, and stirred overnight. The reaction solution was neutralized by adding 1N hydrochloric acid, and concentrated in vacuo. To the obtained residue, 20 ml of ethyl acetate and 20 ml of water were added, and the solution was shaken to separate the water layer, and the ethyl acetate layer was washed once in saturated aqueous solution of sodium hydrogencarbonate. The water layer and saturated aqueous solution of sodium hydrogencarbonate were put together, stirred in ice-cooling, and the pH was adjusted to 2 by 1N hydrochloric acid, and the solution was extracted in 30 ml of ethyl acetate. The ethyl acetate layer was washed twice in saturated brine, dried over sodium sulfate anhydride, and concentrated in vacuo. To the obtained crystalline residue, diethyl ether was added, filtered and dried. Yield: 110 mg.

Thus obtained compound was operated by the same manner as in Example 1, and the captioned compound (diastereomer 1:1 mixture) was obtained.

NMR (270 MHz, DMSO-$d_6$) δppm: 12.85 (1H, bs), 10.41+ 10.39 (1H, s), 8.75+8.72 (1H, s), 8.49+8.33 (1H, d, J=8 Hz), 7.88 (2H, d, J=8 Hz), 7.34 (2H, d, J=7 Hz), 7.28 (1H, d. J=8 Hz), 7.17 (1H, t, J=7 Hz), 7.02-6.91 (2H, m), 5.31 (1H, d. J=17 Hz), 5.16 (1H, d, J=17 Hz), 4.70-4.62 (1H, m), 3.08-2.81 (3H, m), 2.22 (1H, dd, $J_1$=5 Hz, $J_2$=15 Hz), 2.03 (1H, dd, $J_1$9 Hz, $J_2$=15 Hz), 1.54-1.44 (2H, m), 1.12-1.03 (1H, m), 0.90-0.82 (6H, m)

Example 31

Preparation of 3S-[4-(N-hydroxyamino)-2R-isobutyl-3S-methylsuccinyl]amino-1-(4-methoxybenzyl)-3,4dihydrocarbostyril After conducting a reaction between the compound of Reference Example 35 and a corresponding starting material, the captioned compound was obtained in the same manner as in Example 14.

NMR(270 MHz, DMSO-$d_6$) δppm: 10.48 (1H, s), 8.76 (1H, s), 8.51 (1H, d, J=8 Hz), 7.26 (1H, d, J=8 Hz), 7.19-7.14 (3H, m), 7.01-6.95 (2H, m), 6.87 (2H, d, J=9 Hz), 5.10 (2H, bs), 4.68-4.63 (1H, m), 3.70 (3H, s), 3.09 (1H, t, J=15 Hz), 2.96 (1H, dd, $J_1$=6 Hz, $J_2$=15 Hz), 2.56-2.49 (1H, m), 2.22-2.16 (1H, m), 1.58-1.44 (2H, m), 1.01-0.80 (1H, m), 0.99 (3H, d, J=7 Hz, 0.85 (6H, dd, $J_1$=6 Hz, $J_2$=19 Hz)

Example 32

Preparation of 3S-[4-(N-hydroxyamino)-2R-isobutyl-succinyl]amino-1-phthalimidomethyl-3,4-dihydrocarbostyril After conducting a reaction between the compound obtained by trifluoroacetic acid treatment of the compound of Reference Example 36 and a corresponding starting material, the captioned compound was obtained in the same manner as in Example 1.

NMR (270 MHz, DMSO-$d_6$) δppm: 10.36 (1H, s), 8.71 (1H, s), 8.36 (1H, d, J=8 Hz), 7.84 (4H, s), 7.25 (3H, s), 6.90-7.10 (1H, m), 6.05 (1H, d, J=14 Hz), 6.66 (1H, d, J=14 Hz), 4.47 (1H, q, J=8 Hz), 2.70-3.00 (3H, m), 2.18 (1H, dd, d, J=14, 7 Hz), 2.01 (1H, dd, J=14, 7 Hz), 1.40-1.80 (2H, m), 1.00-1.25 (1H, m), 0.88 (6H, dd, J=17. 6 Hz)

Example 33

Preparation of 1-ethoxycarbonylmethyl-3S-[4-(N-hydroxyamino)-2R-isobutylsuccinyl]amino-3,4-dihydrocarbostyril After conducting a reaction between the compound obtained by trifluoroacetic acid treatment of the compound of Reference Example 37 and a corresponding starting material, the captioned compound was obtained in the same manner as in Example 1.

NMR(270 MHz, DMSO-$d_6$) δppm: 10.37 (1H, s), 8.71 (1H, s), 8.29 (1H. d, J=8 Hz), 7.26 (2H, t, J=7 Hz), 7.06 (1H, t, J=7 Hz), 6.97 (1H, d, J=7 Hz), 4.80 (1H, d, J=17 Hz), 4.56 (1H, d, J=17 Hz), 4.42-4.65 (1H, m), 4.14 (2H, q, J=7 Hz), 2.70-3.10 (3H, m), 2.19 (1H, dd, J=14, 7 Hz), 2.01 (1H, dd, J=14, 7 Hz), 1.40-1.78 (2H, m), 1.20 (3H, t, J=7 Hz), 1.00-1.25 (1H, m), 0.87 (6H, dd, J=15, 6 Hz)

Example 34

Preparation of 3S- [4-( N-hydroxyamino )-2R-isobutyl-succinyl]amino-1-carboxymethyl-3,4-dihydrocarbostyril Using 3S-[4-(N-benzyloxyamino )-2R-isobutylsuccinyl]amino-1-ethoxycarbonylmethyl-3,4 -dihydrocarbostyril obtained in the same manner as in Example 11 by using a corresponding starting material, the captioned compound was obtained in the same manner as in Example 30.

NMR (270 MHz, DMSO-$d_6$) δppm: 10.40 (1H, s), 8. 75 (1H, bs), 8.21 (1H, d, J=7 Hz), 7.21 (2H, t, J=7 Hz), 6.98 (1H, t, J=7 Hz), 6.88 (1H, d, J=7 Hz), 4.56 (1H, d, J=17 Hz), 4.47 (1H, dt, J=14, 7 Hz), 4.06 (1H, d, J=17 Hz), 2.65-3.05 (3H, m), 2.18 (1H, dd, J=14, 7 Hz), 2.01 (1H, dd, J=14, 8 Hz), 1.40-1.75 (2H, m), 1.00-1.20 (1H, m), 0.87 (6H, dd, J=16, 7 Hz)

Example 35

Preparation of 7-chloro-1-ethoxycarbonylmethyl-3S-[4-(N-hydroxyamino)-2R-isobutylsuccinyl]amino-3,4-dihydrocarbostyril After conducting a reaction between the compound obtained by trifluoroacetic acid treatment of the compound of Reference Example 38 and a corresponding starting material, the captioned compound was obtained in the same manner as in Example 1.

NMR (270 MHz, DMSO-$d_6$) δppm: 10.38 (1H, s), 8.71 (1H, s), 8.33 (1H, d, J=8 Hz), 7.31 (1H, d, J=7 Hz), 7.10-7.20 (2H, m), 4.79 (1H, d, J=18 Hz), 4.63 (1H, d, J=18 Hz), 4.45-4.60 (1H, m), 4.14 (2H, q, J=7 Hz), 2.60-3.10 (3H, m), 2.17 (1H, dd, J=14, 6 Hz), 2.01 (1H, dd, J=7 Hz), 1.20-1.75 (2H, m), 1.21 (3H, t, J=7 Hz), 1.00-1.20 (1H, m), 0.86 (6H, dd, J=14, 6 Hz)

Example 36

Preparation of 3S-[4-(N-hydroxyamino)-2R-isobutylsuccinyl]amino-1-propoxycarbonylmethyl-3,4-dihydrocarbostyril After conducting a reaction between the compound obtained by trifluoroacetic acid treatment of the compound of Reference Example 41 and a corresponding starting material, the captioned compound was obtained in the same manner as in Example 1.

NMR(270 MHz, DMSO-$d_6$) δppm: 10.38 (1H, s), 8.71 (1H, s), 8.31 (1H, d, J=8 Hz), 7.27 (2H, t, J=8 Hz), 7.05 (1H, t, J=8 Hz), 6.98 (1H, d, J=8 Hz), 4.81 (1H, d, J=17 Hz), 4.59 (1H, d, J=17 Hz), 4.40-4.55 (1H, m), 4.04 (2H, t, J=7 Hz), 2.85-3.10 (3H, m), 2.18 (1H, dd, J=14, 6 Hz), 2.01 (1H, dd, J=14, 7 Hz), 1.40-1.75 (4H, m), 1.00-1.20 (1H, m), 0.75-1.00 (9H, m)

Example 37

Preparation of 3S-[4-(N-hydroxyamino)-2R-isobutylsuccinyl]amino-1-isopropoxycarbonylmethyl-3,4dihydrocarbostyri After conducting a reaction between the compound obtained by trifluoroacetic acid treatment of the compound of Reference Example 42 and a corresponding starting material, the captioned compound was obtained in the same manner as in Example 1.

NMR (270 MHz, DMSO-$d_6$) δppm: 10.38 (1H, s), 8.71 (1H, s), 8.31 (1H, d, J=8 Hz), 7.27 (2H, t, J=8 Hz), 7.05 (1H, t, J=8 Hz), 6.94 (1H, d, J=8 Hz), 4.93 (1H, tt, J=7, 7 Hz), 4.77 (1H, d, J=18 Hz), 4.54 (1H, d, J=8 Hz), 4.45–4.65 (1H, m), 2.70–3.15 (3H, m), 2.18 (1H, dd, J=14, 6 Hz), 2.01 (1, dd, J=14, 7 Hz), 1.40–1.75 (2H, m), 1.21 (3H, d, J=2 Hz), 1.19 (3H, d, J=2 Hz), 1.00–1.20 ([H, m), 0.87 (6H, dd, J=15, 6 Hz)

Example 38

Preparation of 3S-[4-(N-hydroxyamino)-2R-isobutylsuccinyl]amino-1-t-butoxycarbonylmethyl-3,4-dihydrocarbostyril After conducting a reaction between the compound obtained by catalytic reduction treatment of the compound of Reference Example 43 and a corresponding starting material, the captioned compound was obtained in the same manner as in Example 1.1e 43 and a corresponding starting material, the captioned compound was obtained in the same manner as in Example 1.

NMR (270 MHz, DMSO-$d_6$) δppm: 10.38 (1H, brs), 8.71 (1H, brs), 8.30 (H, d, J=8 Hz), 7.25–7.30 (2H, m), 7.06 (1H, t, J=7 Hz), 6.93 (1H, d, J=7 Hz), 4.70 (1H, d, J=17 Hz), 4.44–4.54 (2H, m), 2.75–3.02 (3H, m), 1.98–2.26 (2H, m), 1.61–1.71 (1H, m), 1.42–1.51 (1, m), 1.39 (9H, s), 1.01–1.11 (1H, m), 0.87 (6H, d d, J=15, 7 Hz)

Example 39

Preparation of 1-aminocarbonylmethyl-3S-[4-(N-hydroxy-amino)-2R-isobutylsuccinyl]amino-3,4-dihydrocarbostyril After conducting a reaction between the compound obtained by trifluoroacetic acid treatment of the compound of Reference Example 44 and a corresponding starting material, the captioned compound was obtained in the same manner as in Example 1.

NMR(270 MHz, DMSO-$d_6$) δppm: 10.39 (1H, s), 8.73 (1H, s), 8.24 (1H, d, J=8 Hz), 7.58 (1H, s), 7.10–7.30 (3H, m), 7.02 (1H, t, J=8 Hz), 6.84 (1H, d, J=8 Hz), 4.64 (1H, d, J=17 Hz), 4.50–4.70 (1H, m), 4.19 (1H, d, J=17 Hz), 2.70–3.10 (3H, m), 2.18 (1H, dd, J=14, 6 Hz), 2.01 (1H, dd, J=14, 8 Hz), 1.40–1.75 (2H, m), 0.95–1.20 (1H, m), 0.87 (6H, dd, J=15, 6 Hz)

Example 40

Preparation of 3S-[4-(N-hydroxyamino)-2R-isobutylsuccinyl]amino-1-(N-methylaminocarbonylmethyl)-3,4dihydrocarbostyril After conducting a reaction between the compound obtained by trifluoroacetic acid treatment of the compound of Reference Example 45 and a corresponding starting material, the captioned compound was obtained in the same manner as in Example 1.

NMR (270 MHz, DMSO-$d_6$) δppm: 10.38 (1H, brs), 8.71 (1H, brs), 8.24 (1H, d, J=8 Hz), 8.00 (1H, d, J=5 Hz), 7.23–7.27 (2H, m), 7.03 (1H, t, J=7 Hz), 6.84 (1H, d, J=8 Hz), 4.57–4.69 (2H, m), 4.20 (1H, d, J=17 Hz), 2.92–3.05 (2H, m), 2.74–2.80 (1H, m), 2.60 (3H, d, J=5 Hz), 1.98–2.25 (2H, m), 1.42–1.68 (2H, m), 1.01–1.12 (1H, m), 0.87 (6H, dd, J=15, 7 Hz)

Example 41

Preparation of 3S-[4-(N-hydroxyamino)-2R-isobutylsuccinyl]amino-1-(N-propylaminocarbonylmethyl)-3,4-dihydrocarbostyril After conducting a reaction between the compound obtained by trifluoroacetic acid treatment of the compound of Reference Example 46 and a corresponding starting material, the captioned compound was obtained in the same manner as in Example 1.

NMR(270 MHz, DMSO-$d_6$) δppm: 10.38 (1H, brs), 8.72 (1H, brs), 8.24 (1H, d, J=8 Hz), 8.08 (1H, brs), 7.22–7.27 (2H, m), 7.02 (1H, t, J=7 Hz), 6.84 (1H, d, J=8 Hz), 4.54–4.68 (2H, m), 4.25 (1H, d. J=7 Hz), 2.94–3.05 (3H, m), 2.75–2.80 (1H, m), 1.96–2.25 (2H, m), 1.42–1.68 (2H, m), 1.01–1.12 (1H, m), 0.80–0.91 (9H, m)

Example 42

Preparation of 3S-[4-(N-hydroxyamino)-2R-isobutylsuccinyl]amino-1-(N-methoxyaminocarbonylmethyl)-3,4-dihydrocarbostyril After conducting a reaction between the compound obtained by trifluoroacetic acid treatment of the compound of Reference Example 47 and a corresponding starting material, the captioned compound was obtained in the same manner as in Example 1.

NMR (270 MHz, DMSO-$d_6$) δppm: 11.40 (1H, s), 10.39 (1H, s), 8.72 (1H, s), 8.27 (1H, d, J=8 Hz), 7.20–7.40 (2H, m), 7.04 (1H, t, J=8 Hz), 6.91 (1H, d, J=8 Hz), 4.59 (1H, d, J=16 Hz), 4.40–4.70 (1H, m), 4.25 (1H, d, J=16 Hz), 3.59 (3H, s), 2.70–3.10 (3H, m), 2.19 (1H, dd, J=14.7 Hz), 2.02 (1H, dd, J=14, 7 Hz), 1.30–1.80 (2H, m), 0.90–1.20 (1H, m), 0.87 (6H, d d, J=15, 6 Hz)

Example 43

Preparation of 3S-[4-(N-hydroxyamino)-2R-isobutylsuccinyl]amino-1-(N,N-dimethylaminocarbonylmethyl)-3,4dihydrocarbostyril After conducting a reaction between the compound obtained by trifluoroacetic acid treatment of the compound of Reference Example 48 and a corresponding starting material, the captioned compound was obtained in the same manner as in Example 1.

NMR (270MHz, DMSO-$d_6$) δppm: 10.38 (1H, brs), 8.72 (1H, brs), 8.26 (1H, d, J=8 Hz), 7.20–7.26 (2H, m), 7.00 (1H, t, J=8 Hz), 6.84 (1H, d, J=8 Hz), 4.93 (1H, d, J=17 Hz), 4.46–4.56 (2H, m), 3.09 (3H, s), 2.73–3.02 (6H, m), 1.95–2.25 (2H, m), 1.42–1.70 (2H, m), 1.01–1.12 (1H, m), 0.87 (6H, dd, J=15, 7 Hz)

Example 44

Preparation of 3S-[4-(N-hydroxyamino)-2R-isobutylsuccinyl]amino-1-morpholinocarbonylmethyl-3,4-dihydrocarbocarbostyril After conducting a reaction between the compound obtained by trifluoroacetic acid treatment of the compound of Reference Example 49 and a corresponding starting material, the captioned compound was obtained in the same manner as in Example 1.
NMR (270 MHz, DMSO-d$_6$) δppm: 10.38 (1H, s), 8.71 (1H, s), 8.27 (1H, d, J=8 Hz), 7.24 (2H, t, J=8 Hz), 7.01 (1H, t, J=8 Hz), 6.86 (1H, d, J=8 Hz), 4.97 (1H, d, J=17 Hz), 4.57 (1H, d, J=17 Hz), 4.40–4.60 (1H, m), 3.50–3.75 (8H, m), 2.70–3.20 (3H, m), 2.19 (1H, dd, J=14, 7 Hz), 2.01 (1H, dd, J=14.7 Hz), 140–1.80 (2H, m), 0.95–1.20 (1H, m), 0.87 (6H, dd, J=15, 6 Hz)

Example 45

Preparation of 1-allyl-3S-[4-(N-hydroxyamino)-2R-isobutyl-3S-methylsuccinyl]amino-3,4-dihydrocarbostyril After conducting a reaction between the compound of Reference Example 50 and a corresponding starting material, the captioned compound was obtained in the same manner as in Example 16.
NMR (270 MHz, DMSO-d$_6$) δppm: 10.48 (1H, s), 8.77 (1H, s), 8.45 (1H, d, J=8 Hz), 7.25 (2H, t, J=7 Hz), 7.06-6.99 (1H, m), 5.90-5.80 (1H, m), 5.15-5.06 (2H, m), 4.69-4.53 (2H, m), 4.41 (1H, d, J=17 Hz), 3.04 (1H, t J=15 Hz), 2.93 (1H, dd, J$_1$=6 Hz, J$_2$=15 Hz), 2.54-2.47 (1H, m), 2.20-2.14 (1H, m), 1.60-1.42 (2H, m), 0.97 (3H, d, J=7 Hz), 0.98-0.80 (1H, m). 0.84 (6H, dd, J$_1$=6 Hz, J$_2$=17 Hz)

Example 46

Preparation of 1-cinnamyl-3S-[4-(N-hydroxyamino)-2R-isobutyl-3S-methylsuccinyl]amino-3,4-dihydrocarbostyril After conducting a reaction between the compound of Reference Example 51 and a corresponding material, the captioned compound was obtained in the same manner as in Example 16.
NMR(270 MHz, DMSO-d$_6$)δppm: 10.49 (1H, s), 8.77 (1H, s), 8.47 (1H, d, J=8 Hz), 7.40 (2H, d, J=7 Hz), 7.32-7.21 (5H, m), 7.16 (1H, t, J=8 Hz), 7.02 (1H, t, J=8 Hz), 6.52 (1H, d, J=16 Hz), 6.30 (1H, dt, J$_1$=5 Hz, J$_2$=16 Hz), 4.82 (1H, dd, J$_1$=4 Hz, J$_2$=17 Hz), 4.67-4.52 (2H, m), 3.07 (1H, t, J=15 Hz) 2.96 (1H, dd, J$_1$=6 Hz, J$_2$=15 Hz), 2.56-2.49 (1H, m), 2.21-2.15 (1H, m), 1.61-1.43 (2H, m), 0.98 (3H, d, J=7 Hz) 0.99-0.79 (1H, m), 0.84 (6H, dd, J$_1$6 Hz, J$_2$=18 Hz)

Example 47

Preparation of 3S-[4-(N-hydroxyamino)-2R-isobutylsuccinyl]amino-1-methyl-3,4-dihydrocarbostyril After conducting a reaction between the compound obtained by trifluoroacetic acid treatment of the compound of Reference Example 52 and a corresponding starting material, the captioned compound was obtained in the same manner as in Example 1.
NMR (270 MHz, DMSO-d$_6$) δppm: 10.37 (1H, s), 8.71 (1H, s), 8.20 (1H, d, J=8 Hz), 7.33-7.24 (2H, m), 7.11 (1H, d, J=8 Hz), 7.04 (1H, t, J=8 Hz), 4.49-4.39 (1H, m), 3.28 (3H, s), 2.97-2.89 (2H, m), 2.85-2.73 (1H, m), 2.17 (1H, dd, J$_1$=6 Hz, J$_2$=14 Hz) 2.01 (1H, dd, J$_1$=7 Hz, J$_2$=14 Hz), 1.73-1.62 (1H, m), 1.54-1.42 (1H, m), 1.15-1.00 (1H, m), 0.87 (6H, dd, J$_1$=6 Hz, J$_2$=15 Hz)

Example 48

Preparation of 1-ethyl -3S-[4-(N-hydroxyamino)-2R-isobutylsuccinyl]amino- 3,4-dihydrocarbostyril After conducting a reaction between the compound obtained by trifluoroacetic acid treatment of the compound of Reference Example 53 and a corresponding starking material, the captioned compound was obtained in the same manner as in Example 1.
NMR (270 MHz, DMSO-d$_6$) δppm: 10.37 (1H, s), 8.71 (1H, s), 8.20 (1H, d, J=8 Hz), 7.20–7.35 (2H, m), 7.15 (1H, d, J=8 Hz), 7.03 (1H, t, J=8 Hz), 4.35–4.50 (1H, m), 3.80–4.10 (2H, m), 2.91 (2H, d, J=9 Hz), 2.70–2.90 (1H, m), 2.17 (1H, dd, J=14, 7 Hz), 2.01 (1H, dd, J=14.8 Hz), 1.40–1.80 (2H, m), 1.13 (3H, t, J=7 Hz), 1.00–1.25 (1H, m), 0.87 (6H, dd, J=14, 6 Hz)

Example 49

Preparation of 3S-[4-(N-hydroxyamino)-2R-isobutyl-3S-methylsuccinyl]amino-1-propyl-3,4-dihydrocarbostyril After conducting a reaction between the compound of Reference Example 50 and a corresponding starting material, the captioned compound was obtained in the same manner as in Example 14.
NMR(270 MHz, DMSO-d$_6$) δppm: 10.47 (1H, s), 8.76 (1H, s), 8.41 (1H, d, J=8 Hz), 7.28-7.25 (2H, m), 7.14 (1H, d, J=8 Hz), 7.02 (1H, t, J=7 Hz), 4.52-4.47 (1H, m), 3.84 (2H, t, J=8 Hz), 3.05-2.80 (2H, m), 2.51-2.46 (1H, m), 2.20-2.16 (1H, m), 1.59-1.46 (4H, m), 0.96 (3H, d, J=7 Hz), 0.91-0.80 (10H, m)

Example 50

Preparation of 3S-[4-(N-hydroxyamino)-2R-isobutyl-3S-methylsuccinyl]amino-1-(3-phenylpropyl)-3,4-dihydrocarbostyril After conducting a reaction between the compound of Reference Example 51 and a corresponding starting material, the captioned compound was obtained in the same manner as in Example 14.
NMR (270 MHz, DMSO-d$_6$) δppm: 10.47 (1H, s), 8.76 (1H, s), 8.41 (1H, d, J=8 Hz), 7.30-7.15 (7H, m), 7.07-6.98 (2H, m), 4.51-4.46 (1H, m), 3.92 (2H, t), 2.98-2.88 (2H, m), 2.64 (2H, t, J=8 Hz), 2.51-2.46 (1H, m), 2.20-2.13 (1H, m), 1.87-1.78 (2H, m), 1.85-1.38 (2H, m), 0.96 (3H, d, J=7 Hz), 0. 98-0.80 (1H, m), 0.84-(6H, dd, J$_1$=6 Hz, J$_2$=17 Hz)

Example 51

Preparation of 3S-[4-(N-hydroxyamino)-2R-isobutylsuccinyl]amino-1-(2-hydroxyethyl)-3,4-dihydrocarbostyril After conducting a reaction between the compound obtained by trifluoroacetic acid treatment of the compound of Reference Example 55 and a corresponding starting material, the captioned compound was obtained in the same manner as in Example 1.
NMR (270 MHz, DMSO-d$_6$) δppm: 10.49 (1H, s), 8.70 (1H, s), 8.19 (1H, d, J=8 Hz), 7.15–7.35 (3H, m), 6.90–7.10 (1H, m), 4.85 (1H, t, J=6 Hz), 4.45 (1H, dt, J=13, 8 Hz), 3.90–4.05 (1H, m), 3.84 (1H, dt, J=14, 7 Hz), 3.45–3.65 (2H, m), 2.70–3.00 (3H, m), 2.18 (1H, dd, J=14, 7 Hz), 2.04 (1H, dd, J=14, 7 Hz), 1.35–1.75 (2H, m), 0.95–1.20 (1H, m), 0.87 (6H, dd, J=15, 7 Hz)

Example 52

Preparation of 3S- [4-(N-hydroxyamino)-2R-isobutyl-3-methylsuccinyl]amino-1-methyl-3,4-dihydrocarbostyril After conducting a reaction between the compound of Reference Example 52 and a corresponding starting material, the captioned compound was obtained in the same manner as in Example 15.

NMR (270 MHz, DMSO-d$_6$) δppm: 10.48 (1H, brs), 8.76 (1H, brs), 8.41 (1H, d, J=8 Hz), 7.25–7.33 (2H, m), 7.11 (1H, d, J=8 Hz), 7.03 (1H, d, J=7 Hz), 4.44–4.54 (1H, m), 3.28 (3H, s), 2.89–3.07 (2H, m), 2.49–2.53 (1H, m), 2.16 (1H, dd, J=11, 7 Hz), 1.41–1.62 (2H, m), 0.96 (3H, d, J=7 Hz), 0.84–0.96 (1H, m), 0.84 (6H, dd, J=17, 6 Hz)

Example 53

Preparation of 3S-[4-(N-acetoxyamino)-2R-isobutylsuccinyl]amino-1-methoxy-3,4-dihydrocarbostyril Using acetic anhydride and a corresponding starting material, the captioned compound was obtained in the same manner as in Example 8.

NMR(270 MHz, DMSO-d$_6$) δppm: 13.60 (1H, s), 8.34 (1H, d, J=8 Hz), 7.20–7.40 (2H, m), 7.16 (1H, d, J=8 Hz), 7.07 (1H, t, J=8 Hz), 4.61 (1H, dt, J=12, 8 Hz), 3.82 (3H, s), 2.60–3.10 (3H, m), 2.34 (1H, dd, J=15, 7 Hz), 2.17 (1H, dd, J=15, 7 Hz), 2.15 (3H, s), 1.40–1.80 (2H, m), 1.05–1.40 (1H, m), 0.87 (6H, dd, J=15, 6 Hz)

Example 54

Preparation of 3S-[4-(N-benzoyloxyamino)-2R-isobutyl-3S-methylsuccinyl]amino-1-methoxy-3,4-dihydrocarbostyril Using a corresponding starting material, the captioned compound was obtained in the same manner as in Example 8.

NMR(270 MHz, DMSO-d$_6$) δppm: 12.08 (1H, s), 8.64 (1H, d, J=8 Hz), 8.04 (2H, d, J=7 Hz), 7.76 (1H, t, J=8 Hz), 7.60 (2H, t, J=8 Hz), 7.37-7.29 (2H, m), 7.16 (1H, d, J=7 Hz), 7.07 (1H, t, J=8 Hz), 4.68-4.63 (1H, m), 3.83 (3H, s), 3.08 (1H, t, J=13 Hz) 2.97 (1H, dd, J$_1$=7 Hz, J$_2$=16 Hz), 2.55-2.41 (2H, m), 1.60-1.53 (2H, m), 1.21-1.15 (1H, m), 1.10 (3H, d, J=6 Hz), 0.87 (6H, t, J=7 Hz)

Example 55

Preparation of 3S-[4-(N-hydroxyamino)-2R-isobutyl-3(R or S)-phthalimidomethylsuccinyl]amino-1-methoxy-3,4-dihydrocarbostyril Using a corresponding starting material, the captioned compound was obtained in the same manner as in Example 7.

NMR (270 MHz, DMSO-d$_6$) δppm: 10.47 (1H, s), 8.68 (1H, s), 8.65 (1H, d, J=9 Hz), 7.88-7.80 (4H, m), 7.33 (1H, t, J=8 Hz), 7.26 (1H, d, J=7 Hz), 7.16 (1H, d, J=7 Hz), 7.06 (1H, t, J=7 Hz), 4.61-4.56 (1H, m), 3.89 (1H, dd, J$_1$=3 Hz, J$_2$=15 Hz), 3.82 (3H, s), 3.48 (1H, dd, J$_1$=5 Hz, J$_2$=14 Hz), 3.06-2.89 (2H, m), 2.79-2.63 (2H, m), 1.67-1.54 (3H, m), 0.86 (6H, dd, J$_1$=6Hz, J$_2$=15 Hz)

Example 56

Preparation of 3-[4-(N-hydroxyamino)-2R-isobutyl-3(R or S)-phthalimidemethylsuccinyl]amino-1-methyl-3,4-dihydrocarbostyril After conducting a reaction between the compound obtained by trifluoroacetic acid treatment of the compound of Reference Example 52 and a corresponding starting material, the captioned compound (diastereomer 1:1 mixture) was obtained in the same manner as in Example 7.

NMR (270 MHz, DMSO-d$_6$) δppm: 10.50+10.45 (1H, s), 8.71+8.68 (1H, s), 8.66+8.53 (1H, d, J=8 Hz), 7.88-7.80 (4H, m), 7.32-7.20 (2H, m), 7.14-6.99 (2H, m), 4.56-4.40 (1H, m), 4.05+3.89 (1H, dd, J$_1$=10 Hz, J$_2$=13 Hz), 3.70+3.47 (1H, dd, J$_1$=4 Hz, J$_2$=13 Hz), 3.28 (3H, s), 3.01-2.89 (2H, m), 2.82-2.65 (2H, m), 1.70-1.49 (3H, m), 0.91-0.82 (6H, m)

Example 57

Preparation of 3S-[4-(N-hydroxyamino)-2R-isobutyl-3S-methylsuccinyl]amino-1-(2-propynyl)-3,4-dihydrocarbostyril After conducting a reaction between the compound of Reference Example 56 and a corresponding starting material, the captioned compound was obtained in the same manner as in Example 16.

NMR (270 MHz, DMSO-d$_6$) δppm: 10.49 (1H, brs), 8.77 (1H, brs), 8.48 (1H, d, J=8 Hz), 7.20–7.36 (3H, m), 7.07 (1H, t, J=8 Hz), 4.79 (1H, dd, J=18.2 Hz), 4.62 (1H, dd, J=18.2 Hz), 4.48–4.58 (1H, m), 3.00 (1H, t, J=15 Hz), 2.91 (1H, dd, J=15.6 Hz), 2.46–2.54 (2H, m), 2.14–2.20 (1H, m), 1.58–1.66 (1H, m), 1.46 (1H, dt, J=3.15 Hz), 0.97 (3H, d, J=7 Hz), 0.97-0.85 (1H, m), 0.85 (6H, dd, J=14.7 Hz)

Example 58

Preparation of 3S-[4-(N-hydroxyamino)-3S-aminomethyl-2R-isobutylsuccinyl]amino-1-methoxy-3,4-dihydrocarbostyril 50 mg of 3S-[4-(N-hydroxyamino)-2R-isobutyl-3S-phthalimidomethylsuccinyl]amino-1-methoxy-3,4-dihydrocarbostyril was dissolved in 3 ml of dimethyl formamide, and 19 µl of hydrazine monohydrate was added and stirred for 1 hour at room temperature. The reaction solution was concentrated in vacuo, 1 ml of methanol was added, the insoluble matter was filtered away, and the filtrate was evaporated in vacuum, and 3 ml of diethyl ether was added to the precipitating crystals to filter, and the captioned compound was obtained in a white solid form. Yield: 7 mg.

NMR(270 MHz, DMSO-d$_6$) δppm: 10.56 (1H, brs), 9.56 (1H, s), 8.60 (1H, d, J=8 Hz), 7.32 (2H, dd, J=15, 7 Hz), 7.16 (1H, d, J=7 Hz), 7.07 (1H, t, J=7 Hz), 4.68 (1H, dt, J=12, 8 Hz), 3.82 (3H, s), 2.40–3.20 (6H, m), 0.90–1.80 (3H, m), 0.87 (6H, dd, J=18, 6 Hz)

Example 59

Preparation of 1-aminocarbonylmethyl-3S-[4-(N-hydroxyamino)-2R-isobutyl-3S-acetylthiomethylsuccinyl]-amino-3,4-dihydrocarbostyril After conducting a reaction between the compound of Reference Example 44 and a corresponding starting material, the captioned compound was obtained in the same manner as in Example 4.

NMR(270MHz, DMSO-d$_6$)δppm: 10.62(1H, s), 8.92(1H, s), 8.55(1H, d, J=8Hz), 7.57(1H, s), 7.10–7.35(3H, m), 7.03(1H, t, J=7Hz), 6.86(1H, d, J=7Hz), 4.55–4.75(1H, m), 4.66(1H, d, J=17Hz), 4.20(1H, d, J=17Hz), 2.80–3.20(4H, m), 2.40–2.65(1H, m), 2.31(3H, s), 2.20–2.40(1H, m), 1.40–1.70(2H, m), 0.80–1.00(1H, m), 0.87(3H, d, J=7Hz), 0.81(3H, d, J=7Hz)

Example 60

Preparation of 7-chloro-3S-[4-(N-hydroxyamino)-2R-isobutyl-succinyl]amino-1-methoxy-3,4-dihydrocarbostyril After conducting a reaction between the compound obtained by trifluoroacetic acid treatment of the compound of Reference Example 59 and a corresponding starting material, the captioned compound was obtained in the same manner as in Example 1.

NMR(270MHz, DMSO-$d_6$)δppm: 10.38(1H, brs), 8.72(1H, brs), 8.38(1H, d, J=8Hz), 7.31(1H, d, J=8Hz), 7.11–7.16(2H, m), 4.63(1H, dt, J=11,8Hz), 3.84(3H, s), 2.98(1H, d, J=11Hz), 2.97(1H, d, J=8Hz), 2.75–2.76(1H, m), 2.16(1H, dd, J=6,14Hz), 2.01(1H, dd, J=8,14Hz), 1.60–1.65(1H, m), 1.42–1.49(1H, m), 1.02–1.12(1H, m), 0.87(6H, dd, J=6,12Hz)

Example 61

Preparation of 1-carboxymethyl-3S-[4-(N-hydroxyamino)-2R-isobutyl-3S-methylsuccinyl]amino-3,4-dihydrocarbostyril After conducting a reaction between the compound of Reference Example 39 and a corresponding starting material, the captioned compound was obtained in the same manner as in Example 14.

NMR(270MHz, DMSO-$d_6$)δppm: 10.49(1H, s), 8.75(1H, brs), 8.46(1H, d, J=8Hz), 7.28–7.22(2H, m), 7.02(1H, t, J=8Hz), 6.93(1H, d, J=8Hz), 4.69(1H, d, J=17Hz), 4.57–4.52(1H, m), 4.34(1H, d, J=17Hz), 3.05(1H, t, J=15Hz), 2.91(1H, dd, $J_1$=6Hz, $J_2$=15Hz), 2.51–2.47(1H, m), 2.21–2.15(1H, m), 1.63–1.42(2H, m), 0.99–0.80(10H, m), 0.98(3H, d, J=8Hz), 0.85(6H, dd, $J_1$=6Hz, $J_2$=18Hz)

Example 62

Preparation of 3S-[4-(N-hydroxyamino)-2R-isobutyl-3S-methylsuccinyl]amino-1-methoxymethyl-3,4-dihydrocarbostyril After conducting a reaction between the compound of Reference Example 60 and a corresponding starting material, the captioned compound was obtained in the same manner as in Example 14.

NMR(270MHz, DMSO-$d_6$) δppm: 10.49(1H, s), 8.77(1H, s), 8.49(1H, d, J=8Hz), 7.15–7.35(3H, m), 7.06(1H, t, J=7Hz), 5.47(1H, d, J=10Hz), 5.02(1H, d, J=10Hz), 4.57(1H, dt, J=14,7Hz), 3.27(3H, s), 3.07(1H, t, J=14Hz), 2.91(1H, dd, J=14,6Hz), 2.40–2.60(1H, m), 2.10–2.30(1H, m), 1.50–1.70(1H, m), 1.46(1H, t, J=11Hz), 0.80–1.00(1H, m), 0.98(3H, d, J=7Hz), 0.88(3H, d, J=7Hz), 0.81(3H, d, J=7Hz)

Example 63

Preparation of 3S-[4-(N-hydroxyamino)-2R-isobutyl-3S-acetylthiomethylsuccinyl]amino-1-methoxymethyl-3,4-dihydrocarbostyril After conducting a reaction between the compound of Reference Example 32 and a corresponding starting material, the captioned compound was obtained in the same manner as in Example 4.

NMR(270MHz, DMSO-$d_6$)δppm: 10.61(1H, s), 8.91(1H, s), 8.60(1H, d, J=8Hz), 7.15–7.35(3H, m), 7.07(1H, t, J=7Hz), 5.47(1H, d, J=10Hz), 5.03(1H, d, J=10Hz), 4.60(1H, dt, J=13,7Hz), 3.27(3H, s), 2.80–3.20(4H, m), 2.40–2.70(1H, m), 2.20–2.40(1H, m), 2.30(3H, s), 1.40–1.70(2H, m), 0.80–1.00(1H, m), 0.87(3H, d, J=6Hz), 0.81(3H, d, J=6Hz)

Example 64

Preparation of 3S-[4-(N-hydroxyamino)-2R-isobutyl-3S-mercaptomethylsuccinyl]amino-1-methoxymethyl-3,4-dihydrocarbostyril Using a corresponding starting material, the captioned compound was obtained in the same manner as in Example 5.

NMR(270MHz, DMSO-$d_6$)δppm: 8.55(1H, d, J=8Hz), 7.15–7.30(3H, m), 7.06(1H, t, J=8Hz), 5.47(1H, d, J=10Hz), 5.01(1H, d, J=10Hz), 4.53(1H, dt, J=14,7Hz), 3.27(3H, s), 3.09(1H, d, J=15Hz), 2.97(1H, dd, J=15,7Hz), 2.40–2.70(3H, m), 2.20–2.40(1H, m), 1.40–1.70(2H, m), 0.80–1.00(1H, m), 0.86(3H, d, J=7Hz), 0.82(3H, d, J=7Hz)

Example 65

Preparation of 1-ethoxy-3S-[4-(N-hydroxyamino)-2R-isobutyl-succinyl]amino-3,4-dihydrocarbostyril After conducting a reaction between the compound obtained by trifluoroacetic acid treatment of the compound of Reference Example 29 and a corresponding starting material, the captioned compound was obtained in the same manner as in Example 1.

NMR(270MHz, DMSO-$d_6$)δppm: 10.37(1H, s), 8.71(1H, s), 8.35(1H, d, J=8Hz), 7.35–7.26(2H, m), 7.16(1H, d, J=8Hz), 7.06(1H, t, J=7Hz), 4.63–4.53(1H, m), 4.04(2H, q, J=7Hz), 3.01–2.92(2H, m), 2.80–2.72(1H, m), 2.17(1H, dd, $J_1$=6Hz, $J_2$=14Hz), 2.01(1H, dd, $J_1$=8Hz, $J_2$=15Hz), 1.64–1.43(2H, m), 1.28(3H, t, J=7Hz), 1.12–1.04(1H, m), 0.87(6H, dd, $J_1$=6Hz, $J_2$=12Hz)

Example 66

Preparation of 3S-[4-(N-hydroxyamino)-2R-isobutylsuccinyl]-amino-1-methoxyethoxymethyl-3,4-dihydrocarbostyril After conducting a reaction between the compound obtained by catalytic reduction treatment of the compound of Reference Example 61 and a corresponding starting material, the captioned compound was obtained in the same manner as in Example 1.

NMR(270MHz, DMSO-$d_6$)δppm: 10.41(1H, s), 8.73(1H, s), 8.29(1H, d, J=8Hz), 7.25–7.40(3H, m), 7.00–7.15(1H, m), 5.57(1H, d, J=10Hz), 5.02(1H, d, J=10Hz), 4.51(1H, dt, J=14,7Hz), 3.60(2H, t, J=4Hz), 3.44(2H, t, J=4Hz), 3.22(3H, s), 2.70–3.10(3H, m), 2.18(1H, dd, J=14,7Hz), 2.02(1H, dd, J=14,7Hz), 1.40–1.80(2H, m), 1.00–1.30(1H, m), 0.90(3H, d, J=7Hz), 0.85(3H, d, J=7Hz)

Example 67

Preparation of
3S-[4-(N-hydroxyamino)-2R-isobutyl-3-propylsuccinyl]amino-1-methoxy-3,4-dihydrocarbostyril After conducting a reaction between the compound of Reference Example 62 and a corresponding starting material, the captioned compound was obtained in the same manner as in Example 14.

NMR(270MHz, DMSO-$d_6$)δppm: 10.49(1H, s), 8.78(1H, s), 8.52(1H, d, J=8Hz), 7.36–7.29(2H, m), 7.16(1H, d, J=8Hz), 7.07(1H, t, J=7Hz), 4.67–4.62(1H, m), 3.83(3H, s), 3.04(1H, t, J=16Hz), 2.94(1H, dd, $J_1$=7Hz, $J_2$=16Hz), 2.52–2.43(1H, m), 2.11–2.09(1H, m), 1.58–1.41(2H, m), 1.24–1.03(4H, m), 0.96–0.80(10H, m)

Example 68

Preparation of
3S-[3-benzyl-4-(N-hydroxyamino)-2R-isobutylsuccinyl]amino-1-methoxy-3,4-dihydrocarbostyril After conducting a reaction between the compound of Reference Example 63 and a corresponding starting material, the captioned compound was obtained in the same manner as in Example 14.

NMR(270MHz, DMSO-$d_6$)δppm: 10.28(1H, s), 8.69–8.65(2H, m), 7.36–7.03(9H, m), 4.68–4.63(1H, m), 3.84(3H, s), 3.12(1H, t, J=15Hz), 2.98(1H, dd, $J_1$=7Hz, $J_2$=16Hz), 2.75–2.71(2H, m), 2.58–2.55(1H, m), 2.45–2.39(1H, m), 1.62–1.48(2H, m), 1.03–0.97(1H, m), 0.87(6H, dd, $J_1$=6Hz, $J_2$=16Hz)

Example 69

Preparation of
3S-[4-(N-hydroxyamino)-2R-isobutyl-3-(4-methoxybenzyl)succinyl]amino-1-methoxy-3,4-dihydrocarbostyril After conducting a reaction between the compound of Reference Example 64 and a corresponding starting material, the captioned compound was obtained in the same manner as in Example 14.

NMR(270MHz, DMSO-$d_6$)δppm: 10.25(1H, s), 8.65(1H, d, J=8Hz), 8.64(1H, s), 7.36–7.27(2H, m), 7.16(1H, d, J=7Hz), 7.05(1H, dt, $J_1$=1Hz, $J_2$=7Hz), 6.99(2H, d, J=9Hz), 6.79(2H, d, J=9Hz), 4.68–4.63(1H, m), 3.84(3H, s), 3.71(3H, s), 3.11(1H, t, J=15Hz), 2.98(1H, dd, $J_1$=7Hz, $J_2$=16Hz), 2.68–2.56(3H, m), 2.39–2.34(1H, m), 1.64–1.54(2H, m), 1.00–0.96(1H, m), 0.86(6H, dd, $J_1$=7Hz, $J_2$=16Hz)

Example 70

Preparation of
1-carboxymethyl-3S-[4-(N-hydroxyamino)-2R-isobutyl-3(R or S)-phthalimidomethylsuccinyl]amino-3,4-dihydrocarbostyril After conducting a reaction between the compound of Reference Example 39 and a corresponding starting material, the captioned compound was obtained in the same manner as in Example 14.

NMR(270MHz, DMSO-$d_6$)δppm: 10.50(1H, s), 8.70(1H, bs), 8.57(1H, d, J=8Hz), 7.88–7.80(4H, m), 7.28–7.23(2H, m), 7.02(1H, t, J=7Hz), 6.94(1H, d, J=8Hz), 4.71(1H, d, J=18Hz), 4.50–4.37(2H, m), 3.90(1H, dd, $J_1$=10Hz, $J_2$=14Hz), 3.48(1H, dd, $J_1$=5Hz, $J_2$=14Hz), 3.17–2.92(2H, m), 2.84–2.65(2H, m), 1.71–1.54(2H, m), 1.00–0.96(1H, m), 0.86(6H, dd, $J_1$=7Hz, $J_2$=19Hz)

Example 71

Preparation of
3S-[4-(N-hydroxyamino)-2R-isobutyl-3S-methylsuccinyl]amino-1-methoxyethoxymethyl-3,4-dihydrocarbostyril After conducting a reaction between a corresponding starting material and the compound obtained by catalytic reduction treatment of the compound of Reference Example 61, the captioned compound was obtained in the same manner as in Example 62.

NMR(270MHz, DMSO-$d_6$)δppm: 10.49(1H, s), 8.78(1H, s), 8.48(1H, d, J=8Hz), 7.20–7.35(3H, m), 7.00–7.10(1H, m), 5.56(1H, d, J=10Hz), 5.04(1H, d, J=10Hz), 4.55(1H, dt, J=14,7Hz), 3.60(2H, dd, J=6,3Hz), 3.44(2H, dd, J=6,3Hz), 3.22(3H, s), 3.06(1H, t, J=14Hz), 2.91(1H, dd, J=14,6Hz), 2.45–2.60(1H, m), 2.10–2.30(1H, m), 1.50–1.70(1H, m), 1.47(1H, t, J=13Hz), 0.80–1.10(1H, m), 0.98(3H, d, J=7Hz), 0.88(3H, d, J=7Hz), 0.81(3H, d, J=7Hz)

Example 72

Preparation of
3S-[4-(N-hydroxyamino)-2S-isobutylsuccinyl]-amino-1-methoxy-3,4-dihydrocarbostyril After conducting a reaction between the compound of Reference Example 65 and a corresponding starting material, the captioned compound was obtained in the same manner as in Example 1.

NMR(270MHz, DMSO-$d_6$)δppm: 10.41(1H, brs), 8.75(1H, brs), 8.50(1H, d, J=8Hz), 7.32(2H, t, J=8Hz), 7.16(1H, d, J=8Hz), 7.07(1H, t, J=8Hz), 4.06(1H, dt, J=11,8Hz), 3.83(3H, s), 2.98(1H, d, J=11Hz), 2.97(1H, d, J=8Hz), 2.79–2.84(1H, m), 2.21(1H, dd, J=5,14Hz), 2.02(1H, dd, J=9,14Hz), 1.42–1.51(2H, m), 1.02–1.12(1H, m), 0.84(6H, d, J=6Hz)

Example 73

Preparation of
3S-[4-(N-hydroxyamino)-2R-isobutylsuccinyl]-amino-1-methoxymethoxyethyl-3,4-dihydrocarbostyril After conducting a reaction between the compound obtained by catalytic reduction treatment of the compound of Reference Example 66 and a corresponding starting material, the captioned compound was obtained in the same manner as in Example 1.

NMR(270MHz, DMSO-$d_6$)δppm: 10.37(1H, s), 8.70(1H, s), 8.23(1H, d, J=8Hz), 7.20–7.35(3H, m), 7.03(1H, t, J=8Hz), 4.52(2H, q, J=6Hz), 4.40–4.60(1H, m), 4.09(2H, t, J=6Hz), 3.63(2H, t, J=6Hz), 3.17(3H, s), 2.70–3.00(3H, m), 2.18(1H, dd, J=15,6Hz), 2.01(1H, dd, J=15,7Hz), 1.40–1.80(2H, m), 1.00–1.20(1H, m), 0.90(3H, d, J=7Hz), 0.84(3H, d, J=7Hz)

Example 74

Preparation of
3S-[4-(N-hydroxyamino)-2R-isobutyl-3-(3-phenylpropyl)succinyl]amino-1-methoxy-3,4-dihydrocarbostyril After conducting a reaction between the compound of Reference Example 67 and a corresponding starting material, the captioned compound was obtained in the same manner as in Example 14.

NMR(270MHz, DMSO-$d_6$)δppm: 10.52(1H, s), 8.80(1H, s), 8.52(1H, d, J=8Hz), 7.35(1H, t, J=7Hz), 7.30–7.15(7H, m), 7.10(1H, t, J=7Hz), 4.66–4.61(1H, m), 3.83(3H, s), 2.96(1H, t, J=16Hz), 2.82(1H, dd, $J_1$=6Hz, $J_2$=16Hz), 2.56–2.43(3H, m), 2.14–2.09(1H, m), 1.57–1.29(6H, m), 0.95–0.92(1H, m), 0.83(6H, dd, $J_1$=6Hz, $J_2$=12Hz)

Example 75

Preparation of
3S-[4-(N-hydroxyamino)-2R-isobutyl-3-(2-methylbenzyl)succinyl]amino-1-methoxy-3,4-dihydrocarbostyril After conducting a reaction between the compound of Reference Example 68 and a corresponding starting material, the captioned compound was obtained in the same manner as in Example 14.

NMR(270MHz, DMSO-$d_6$)δppm: 10.21(1H, s), 8.70(1H, d, J=8Hz), 8.60(1H, s), 7.33(1H, t, J=8Hz), 7.28(1H, d, J=7Hz), 7.16(1H, d, J=8Hz), 7.07–6.96(5H, m), 4.68–4.62(1H, m), 3.84(3H, s), 3.15(1H, t, J=15Hz), 2.98(1H, dd, $J_1$=6Hz, $J_2$=16Hz), 2.75–2.71(2H, m), 2.61–2.56(1H, m), 2.42–2.37(1H, m), 2.22(3H, s), 1.63–1.47(2H, m), 1.00–0.96(1H, m), 0.87(6H, dd, $J_1$=6Hz, $J_2$=17Hz)

Example 76

Preparation of
3S-[4-(N-hydroxyamino)-2R-isobutyl-3-(3-methylbenzyl)succinyl]amino-1-methoxy-3,4-dihydrocarbostyril After conducting a reaction between the compound of Reference Example 69 and a corresponding starting material, the captioned compound was obtained in the same manner as in Example 14.

NMR(270MHz, DMSO-$d_6$)δppm: 10.27(1H, s), 8.67–8.64(2H, m), 7.36–7.27(2H, m), 7.18–6.85(6H, m), 4.68–4.63(1H, m), 3.84(3H, s), 3.12(1H, t, J=15Hz), 2.98(1H, dd, $J_1$=7Hz, $J_2$=16Hz), 2.75–2.49(3H, m), 2.44–2.38(1H, m), 2.26(3H, s), 1.64–1.47(2H, m), 1.01–0.97(1H, m), 0.87(6H, dd, $J_1$=6Hz, $J_2$=16Hz)

Example 77

Preparation of
3S-[4-(N-hydroxyamino)-2R-isobutyl-3-(4-methylbenzyl)succinyl]amino-1-methoxy-3,4-dihydrocarbostyril After conducting a reaction between the compound of Reference Example 70 and a corresponding starting material, the captioned compound was obtained in the same manner as in Example 14.

NMR(270MHz, DMSO-$d_6$)δppm: 10.25(1H, s), 8.66–8.63(2H, m), 7.36–7.27(2H, m), 7.16(1H, d, J=8Hz), 7.08–7.02(3H, m), 6.96(2H, d, J=8Hz), 4.68–4.63(1H, m), 3.84(3H, s), 3.11(1H, t, J=13Hz), 2.98(1H, dd, $J_1$=6Hz, $J_2$=15Hz), 2.75–2.49(3H, m), 2.41–2.35(1H, m), 2.25(3H, s), 1.61–1.47(2H, m), 1.00–0.82(7H, m), 0.86(6H, dd, $J_1$=6Hz, $J_2$=15Hz)

Example 78

Preparation of
3S-[4-(N-hydroxyamino)-2R-heptylsuccinyl]-amino-1-methoxy-3,4-dihydrocarbostyril After conducting a reaction between the compound of Reference Example 73 and a corresponding starting material, the captioned compound was obtained in the same manner as in Example 14.

NMR(270MHz, DMSO-$d_6$)δppm: 10.38(1H, s), 8.71(1H, s), 8.32(1H, d, J=8Hz), 7.32(2H, dd, J=16,8Hz), 7.16(1H, d, J=8Hz), 7.07(1H, t, J=8Hz), 4.61(1H, dt, J=12,8Hz), 3.82(3H, s), 2.85–3.10(2H, m), 2.55–2.80(1H, m), 2.20(1H, dd, J=14,7Hz), 2.02(1H, dd, J=14.7Hz), 1.05–1.60(12H, m), 0.87(3H, t, J=6Hz)

Example 79

Preparation of
3S-[4-(N-acetylhydroxyamino)-2R-isobutylsuccinyl]-amino-1-methoxymethyl-3,4-dihydrocarbostyril Using acetic anhydride and a corresponding starting material, the captioned compound was obtained in the same manner as in Example 8.

NMR(270MHz, DMSO-$d_6$)δppm: 11.63(1H, s), 8.33(1H, d, J=8Hz), 7.20–7.35(3H, m), 7.07(1H, t, J=7Hz), 5.49(1H, d, J=10Hz), 5.00(1H, d, J=10Hz), 4.53(1H, dt, J=13,8Hz), 3.26(3H, s), 2.90–3.10(2H, m), 2.70–2.90(1H, m), 2.35(1H, dd, J=15,6Hz), 2.18(1H, dd, J=15,8Hz), 2.15(3H, s), 1.40–1.80(2H, m), 1.10–1.35(1H, m), 0.90(3H, d, J=7Hz), 0.85(3H, d, J=7Hz)

Example 80

Preparation of
7-chloro-3S-[4-(N-hydroxyamino)-2R-isobutyl-succinyl]amino-1-methoxymethyl-3,4-dihydrocarbostyril After conducting a reaction between the compound obtained by hydrazine treatment of the compound of Reference Example 74 and a corresponding starting material, the captioned compound was obtained in the same manner as in Example 1.

NMR(270MHz, DMSO-$d_6$)δppm: 10.38(1H, brs), 8.72(1H, brs), 8.32(1H, d, J=8Hz), 7.30(1H, d, J=8Hz), 7.28(1H, d, J=2Hz), 7.13(1H, dd, J=2,8Hz), 5.47(1H, d, J=11Hz), 5.06(1H, d, J=11Hz), 4.55(1H, dt, J=11,8Hz), 3.26(3H, s), 2.98(1H, d, J=11Hz), 2.97(1H, d, J=8Hz), 2.75–2.84(1H, m), 2.17(1H, dd, J=7,15Hz), 2.01(1H, dd, J=8,15Hz), 1.51–1.59(1H, m), 1.43–1.53(1H, m), 1.02–1.12(1H, m), 0.87(6H, dd, J=6,13Hz)

Example 81

Preparation of
1-tert-butoxyethyl-3S-[4-(N-hydroxyamino)-2R-isobutylsuccinyl]amino-3,4-dihydrocarbostyril After conducting a reaction between the compound obtained by catalytic reduction treatment of the compound of Reference Example 75 and a corresponding starting material, the captioned compound was obtained in the same manner as in Example 1.

NMR(270MHz, DMSO-$d_6$)δppm: 10.37(1H, brs), 8.70(1H, brs), 8.20(1H, d, J=8Hz), 7.22–7.31(3H, m), 6.99–7.05(1H, m), 4.43(1H, dt, J=11,8Hz), 4.04(1H, dt, J=14,6Hz), 3.85(1H, dt, J=14,7Hz), 3.45–3.50(1H, m), 2.92(1H, d, J=11Hz), 2.91(1H, d, J=8Hz), 2.76–2.82(1H, m), 2.18(1H, dd, J=7,15Hz), 2.01(1H, dd, J=8,15Hz), 1.59–1.67(1H, m), 1.45–1.54(1H, m), 1.06–1.13(1H, m), 1.06(9H, s), 0.87(6H, dd, J=7,14Hz)

Example 82

Preparation of
3S-[4-(N-hydroxyamino)-2R-isobutylsuccinyl]-amino-1-methoxyethyl-3,4-dihydrocarbostyril After conducting a reaction between the compound obtained by trifluoroacetic acid treatment of the compound of Reference Example 76 and a corresponding starting material, the captioned compound was obtained in the same manner as in Example 1.

NMR(270MHz, DMSO-$d_6$)δppm: 10.37(1H, brs), 8.71(1H, brs), 8.23(1H, d, J=8Hz), 7.23–7.31(3H, m), 7.00–7.06(1H, m), 4.45(1H, dt, J=11,8Hz), 4.01–4.11(2H, m), 3.45–3.54(2H, m), 3.23(3H, s), 2.92(1H, d, J=11Hz), 2.91(1H, d, J=8Hz), 2.75–2.79(1H, m), 2.17(1H, dd, J=7,14Hz), 2.01(1H, dd, J=8,14Hz), 1.62–1.66(1H, m), 1.43–1.54(1H, m), 1.08–1,15(1H, m), 0.87(6H, dd, J=7,14Hz)

Example 83

Preparation of
3R-[4-(N-hydroxyamino)-2R-isobutylsuccinyl]-amino-1-methoxymethyl-3,4-dihydrocarbostyril After conducting a reaction between the compound obtained by catalytic reduction treatment of the compound of Reference Example 77 and a corresponding starting material, the captioned compound was obtained in the same manner as in Example 1.

NMR(270MHz, DMSO-$d_6$)δppm: 10.40(1H, brs), 8.74(1H, brs), 8.39(1H, d, J=8Hz), 7.22–7.31(3H, m), 7.00–7.05(1H, m), 4.43(1H, dt, J=8,11Hz), 4.02–4.12(2H, m), 3.49–3.53(2H, m), 3.24(3H, s), 2.91(1H, d, J=8Hz), 2.90(1H, d, J=11Hz), 2.83–2.88(1H, m), 2.11(1H, dd, J=5, 14Hz), 2.01(1H, dd, J=9,14Hz), 1.44–1.47(2H, m), 1.05–1.07(1H, m), 0.84(6H, dd, J=6,2Hz)

Example 84

Preparation of
3S-[4-(N-hydroxyamino)-2R-ethoxyethylsuccinyl]-amino-1-methoxy-3,4-dihydrocarbostyril Transforming 4-ethoxypropionic acid [Vlado Prelog, Ber. 72B, 1103 6 (1939)] into 4-ethoxypropionyl chloride by using oxalyl chloride, and after allowing to react with a corresponding starting material, the captioned compound was obtained in the same manner as in Example 78.

NMR(270MHz, DMSO-$d_6$)δppm: 10.39(1H, brs), 8.71(1H, s), 8.30(1H, d, J=8Hz), 7.32(2H, dd, J=16,8Hz), 7.16(1H, d, J=8Hz), 7.08(1H, t, J=8Hz), 4.61(1H, dt, J=12, 8Hz), 3.82(3H, s), 3.41(2H, q, J=8Hz), 3.25–3.50(2H, m), 2.90–3.10(2H, m), 2.70–2.90(1H, m), 2.23(1H, dd, J=15, 7Hz), 1.50–1.80(2H, m), 1.11(3H, t, J=7Hz)

Example 85

Preparation of
3R-[4-(N-hydroxyamino)-2R-isobutylsuccinyl]-amino-1-methoxymethyl-3,4-dihydrocarbostyril After conducting a reaction between a corresponding starting material and using a compound obtained by the method of J. Med. Chem. 1972, 15, 325, the captioned compound was obtained in the same manner as in Example 27.

NMR(270MHz, DMSO-$d_6$)δppm: 10.41(1H, s), 8.75(1H, s), 8.44(2H, d, J=8Hz), 7.20–7.35(3H, m), 7.06(1H, t, J=7Hz), 5.50(1H, d, J=10Hz), 5.01(1H, d, J=10Hz), 4.51(1H, dt, J=12,8Hz), 3.26(3H, s), 2.75–3.10(3H, m), 2.22(1H, dd, J=15.5Hz), 2.02(1H, dd, J=15.9Hz), 1.40–1.60(1H, m), 0.95–1.35(2H, m), 0.85(6H, t, J=5Hz)

Example 86

Preparation of
3S-[4-(N-hydroxyamino)-2R-isobutyl-3S-acetylthiomethylsuccinyl]amino-1-methoxy-3,4-dihydrocarbostyril Using a corresponding starting material, the captioned compound was obtained in the same manner as in Example 4.

NMR(270MHz, DMSO-$d_6$)δppm: 10.61(1H, s), 8.91(1H, s), 8.67(1H, d, J=8Hz), 7.34(1H, t, J=8Hz), 7.27(1H, d, J=8Hz), 7.17(1H, d, J=8Hz), 7.07(1H, t, J=7Hz), 4.67(1H, dt, J=12,8Hz), 3.83(3H, s), 2.80–3.15(4H, m), 2.25–2.65(1H, m), 2.20–2.40(1H, m), 2.30(3H, s), 1.50–1.70(1H, m), 1.51(1H, t, J=11Hz), 0.93(1H, t, J=11Hz), 0.86(3H, d, J=7Hz), 0.82(3H, d, J=7Hz)

Example 87

Preparation of 3S-[4-(N-hydroxyamino)-2R-isobutyl-3S-mercaptomethylsuccinyl]amino-1-methoxy-3,4-dihydrocarbostyril Using a corresponding starting material, the captioned compound was obtained in the same manner as in Example 5.

NMR(270MHz, DMSO-$d_6$)δppm: 8.62(1H, d, J=8Hz), 7.32(2H, dd, J=14.7Hz), 7.15(1H, d, J=8Hz), 7.07(1H, t, J=7Hz), 4.58(1H, dt, J=14,7Hz), 3.82(3H, s), 3.10(1H, t, J=15Hz), 2.98(1H, dd, J=15,7Hz), 2.40–1.65(3H, m), 2.20–2.40(1H, m), 1.45–1.70(1H, m), 1.50(1H, t, J=12Hz), 0.94(1H, t, J=12Hz), 0.86(3H, d, J=7Hz), 0.82(3H, d, J=7Hz)

Example 88

Preparation of
3S-[4-(N-hydroxyamino)-2R-isobutyl-3-(4-methoxycarbonylbenzyl)succinyl]amino-1-methoxy-3,4-dihydrocarbostyril After conducting a reaction between the compound of Reference Example 78 and a corresponding starting material, the captioned compound was obtained in the same manner as in Example 14.

NMR(270MHz, DMSO-d$_6$)δppm: 10.29(1H, s), 8.70(1H, d, J=8Hz), 8.66(1H, s), 7.85(2H, d, J=8Hz), 7.36–7.27(2H, m), 7.22(2H, d, J=8Hz), 7.16(1H, d, J=7Hz), 7.05(1H, t, J=7Hz), 4.66–4.61(1H, m), 3.84(6H, s), 3.14(1H, t, J=15Hz), 2.99(1H, dd, J$_1$=7Hz, J$_2$=16Hz), 2.81–2.78(2H, m), 2.60–2.57(1H, m), 2.46–2.40(1H, m), 1.62–1.48(2H, m), 1.01–0.97(1H, m), 0.87(6H, dd, J$_1$=6Hz, J$_2$=16Hz)

Example 89

Preparation of
3S-[3-hexyl-4-(N-hydroxyamino)-2R-isobutyl-succinyl]amino-1-methoxy-3,4-dihydrocarbostyril After conducting a reaction between the compound of Reference Example 79 and a corresponding starting material, the captioned compound was obtained in the same manner as in Example 14.

NMR(270MHz, DMSO-d$_6$)δppm: 10.48(1H, s), 8.77(1H, s), 8.53(1H, d, J=8Hz), 7.34(1H, t, J=8Hz), 7.28(1H, d, J=7Hz), 7.16(1H, d, J=8Hz), 7.06(1H, t, J=8Hz), 4.66–4.61(1H, m), 3.83(3H, s), 2.99(1H, t, J=13Hz), 2.90(1H, dd, J$_1$=9Hz, J$_2$=12Hz), 2.51–2.42(1H, m), 2.09–2.05(1H, m), 1.57–1.41(2H, m), 1.22–1.09(10H, m), 0.95–0.80(10H, m)

Example 90

Preparation of 3S-[4-(N-hydroxyamino)-2R-butyl-3S-methylsuccinyl]amino-1-methoxy-3,4-dihydrocarbostyril After conducting a reaction between the compound of Reference Example 80 and a corresponding starting material, the captioned compound was obtained in the same manner as in Example 62.

NMR(270MHz, DMSO-d$_6$)δppm: 10.49(1H, s), 8.76(1H, s), 8.52(1H, d, J=8Hz), 7.32(2H, dd, J=16,8Hz), 7.16(1H, d, J=8Hz), 7.07(1H, t, J=8Hz), 4.62(1H, dt, J=14,7Hz), 3.83(3H, s), 2.30–2.50(1H, m), 2.10–2.30(1H, m), 1.00–1.50(6H, m), 0.95(3H, d, J=7Hz), 0.85(3H, t, J=7Hz)

Example 91

Preparation of
3S-[4-(N-hydroxyamino)-2R-butylsuccinyl]amino-1-methoxy-3,4-dihydrocarbostyril After conducting a reaction between the compound of Reference Example 80 and a corresponding starting material, the captioned compound was obtained in the same manner as in Example 1.

NMR(270MHz, DMSO-d$_6$)δppm: 10.38(1H, s), 8.70(1H, s), 8.31(1H, d, J=7Hz), 7.32(2H, dd, J=16,8Hz), 7.16(1H, d, J=8Hz), 7.07(1H, t, J=8Hz), 4.61(1H, dt, J=13,8Hz), 3.82(3H, s), 2.80–3.10(2H, m), 2.55–2.80(1H, m), 2.20(1H, dd, J=14,7Hz), 2.03(1H, dd, J=14,8Hz), 1.10–1.60(6H, m), 0.87(3H, t, J=7Hz)

Example 92

Preparation of
3S-[4-(N-hydroxyamino)-2R-isobutyl-3-(3,4-methylenedioxybenzyl)succinyl]amino-1-methoxy-3,4-dihydrocarbostyril After conducting a reaction between the compound of Reference Example 81 and a corresponding starting material, the captioned compound was obtained in the same manner as in Example 14.

NMR(270MHz, DMSO-d$_6$)δppm: 10.28(1H, s), 8.68(1H, s), 8.65(1H, d, J=8Hz), 7.36–7.27(2H, m), 7.16(1H, d, J=7Hz), 7.05(1H, dt, J$_1$=1Hz, J$_2$=7Hz), 6.77(1H, d, J=8Hz), 6.60(1H, d, J=2Hz), 6.52(1H, dd, J$_1$=2Hz, J$_2$=8Hz), 5.95(2H, s), 4.66–4.61(1H, m), 3.84(3H, s), 3.12(1H, t, J=15Hz), 2.98(1H, dd, J$_1$=7Hz, J$_2$=16Hz), 2.66–2.49(3H, m), 2.38–2.32(1H, m), 1.60–1.46(2H, m), 0.99–0.95(1H, m), 0.86(6H, dd, J$_1$=6Hz, J$_2$=15Hz)

Example 93

Preparation of
3S-[3-(3-ethoxycarbonylpropyl)-4-(N-hydroxyamino)-2R-isobutylsuccinyl]amino-1-methoxy-3,4-dihydrocarbostyril After conducting a reaction between the compound of Reference Example 82 and a corresponding starting material, the captioned compound was obtained in the same manner as in Example 14.

NMR(270MHz, DMSO-d$_6$)δppm: 10.53(1H, s), 8.83(1H, s), 8.54(1H, d, J=8Hz), 7.34(1H,t, J=8Hz), 7.28(1H, d, J=8Hz), 7.16(1H, d, J=8Hz), 7.07(1H, t, J=8Hz), 4.69–4.59(1H, m), 4.05(2H, q, J=7Hz), 3.83(3H, s), 3.08–2.93(2H, m), 2.51–2.43(1H, m), 2.32–2.22(2H, m), 2.10–2.06(1H, m), 1.56–1.31(6H, m), 1.18(3H, t, J=7Hz), 0.95–0.80(7H, m), 0.84(6H, dd, J$_1$=6Hz, J$_2$=12Hz)

Example 94

Preparation of
1-ethoxymethyl-3S-[4-(N-hydroxyamino)-2R-isobutylsuccinyl]amino-3,4-dihydrocarbostyril After conducting a reaction between the compound obtained by catalytic reduction treatment of the compound of Reference Example 83 and a corresponding starting material, the captioned compound was obtained in the same manner as in Example 1.

NMR(270MHz, DMSO-d$_6$)δppm: 10.39(1H, s), 8.72(1H, s), 8.28(1H, d, J=8Hz), 7.20–7.35(3H, m), 7.06(1H, t, J=7Hz), 5.54(1H, d, J=10Hz), 5.00(1H, d, J=10Hz), 4.50(1H, dt, J=14,7Hz), 3.51(2H, q, J=7Hz), 2.70–3.10(3H, m), 2.15(1H, dd, J=14,7Hz), 2.01(1H, dd, J=14,7Hz), 1.40–1.80(2H, m), 1.10(3H, t, J=7Hz), 1.00–1.20(1H, m), 0.90(3H, d, J=7Hz), 0.85(3H, d, J=7Hz)

Example 95

Preparation of
3S-[4-(N-hydroxyamino)-2S-butoxymethylsuccinyl]-amino-1-methoxy-3,4-dihydrocarbostyril After conducting a reaction between the compound of Reference Example 85 and a corresponding starting material, the captioned compound was obtained in the same manner as in Example 1.

NMR(270MHz, DMSO-d$_6$)δppm: 10.37(1H, s), 8.69(1H, s), 8.34(1H, d, J=8Hz), 7.34(1H, t, J=8Hz), 7.28(1H, d, J=8Hz), 7.16(1H, d, J=8Hz), 7.08(1H, t, J=8Hz), 4.58(1H, dt, J=12.8Hz), 3.83(3H, s), 3.30–3.60(4H, m), 2.90–3.10(3H, m), 2,27(1H, dd, J=15.8Hz), 2.11(1H, dd, J=15.6Hz), 1.20–1.60(4H, m), 0.88(3H, t, J=7Hz)

Example 96

Preparation of
3S-[4-(N-hydroxyamino)-2-isobutyl-3-methyl-thiomethylsuccinyl]amino-3,4-dihydrocarbostyril Using the compound of Reference Example 87 and a corresponding starting material, the captioned compound was obtained in the same as in Example 4.

NMR(270MHz, DMSO-d$_6$)δppm: 10.61(1H, s), 10.19(1H, s), 8.87(1H, s), 8.45(1H, d, J=8Hz), 7.18(2H, dd, J=16,8Hz), 6.90(2H, dd, J=16,8Hz), 4.41(1H, dt, J=14.7Hz), 2.80–3.30(3H, m), 2,25–2.70(3H, m), 2.00(3H, s), 1.30–1.70(2H, m), 0.80–1.10(1H, m), 0.86(3H, d, J=7Hz), 0.82(3H, d, J=7Hz)

Example 97

Preparation of
3S-[4-(N-hydroxyamino)-2R-isobutyl-S-(2-thienylthiomethyl)succinyl]amino-1-methoxy-3,4-dihydrocarbostyril After conducting a reaction of a corresponding starting material, the captioned compound was obtained in the same manner as in Example 4.

NMR(270MHz, DMSO-d$_6$)δppm: 10.70(1H, s), 8.96(1H, s), 8.64(1H, d, J=8Hz), 7.60(1H, dd, J=5.1Hz), 7.33(1H, t, J=8Hz), 7.99–7.30(5H, m), 4.54(1H, dt, J=14,7Hz), 3.81(3H, s), 2.80–3.20(5H, m), 2.30–2.50(1H, m), 1.40–1.65(2H, m), 0.80–1.00(1H, m), 0.84(3H, d, J=6Hz), 0.81(3H, d, J=6Hz)

Example 98

Preparation of
3S-[4-(N-hydroxyamino)-2S-butoxymethyl-3S-methylsuccinyl]amino-3,4-dihydrocarbostyril Using a corresponding starting material, the captioned compound was obtained in the same manner as in Example 62.

NMR(270MHz, DMSO-d$_6$)δppm: 10.48(1H, s), 10.26(1H, s), 8.77(1H, s), 8.35(1H, d, J=7Hz), 7.16(2H, t, J=8Hz), 6.93(1H, d, J=8Hz), 6.87(1H, d, J=8Hz), 4.40(1H, dt, J=12,7Hz), 3.10–3.50(4H, m), 2.80–3.10(2H, m), 2.74(1H, dt, J=4,10Hz), 2.10–2.30(1H, m), 1.20–1.50(4H, m), 0.98(3H, d, J=7Hz), 0.85(3H, t, J=7Hz)

Example 99

Preparation of
1-ethoxyethoxy-3S-[4-(N-hydroxyamino)-2R-isobutylsuccinyl]amino-3,4-dihydrocarbostyril After conducting a reaction between the compound of Reference Example 88 and a corresponding starting material, the captioned compound was obtained in the same manner as in Example 1.

NMR(270MHz, DMSO-d$_6$)δppm: 10.38(1H, s), 8.72(1H, s), 8.36(1H, D, J=8Hz), 7.32(2H, d, J=3Hz), 7.27(1H, d, J=7Hz), 7.00–7.10(1H, m), 4.60(1H, dt, J=13.7Hz), 4.15(1H, t, J=4Hz), 3.63(2H, dd, J=7.4Hz), 3.44(2H, q, J=7Hz), 2.85–3.10(2H, m), 2.65–2.85 (1H, m), 2.17(1H, dd, J=14,7Hz), 2.01(1H, dd, J=14,8Hz), 1.40–1.75 (2H, m), 1.00–1.20(1H, m), 1.13(3H, t, J=7Hz), 0.89(3H, d, J=6Hz), 0.84(3H, d, J=6Hz)

Example 100

Preparation of
1-ethoxy-3R-[4-(N-hydroxyamino)-2R-isobutyl-succinyl]amino-3,4-dihydrocarbostyril Using a corresponding starting material, the captioned compound was obtained in the same manner as in Example 1.

NMR(270MHz, CDCl$_3$)δppm: 10.42(1H, s), 8.76(1H, s), 8.51(1H, d, J=8Hz), 7.31(2H, dd, J=16,8Hz), 7.16(1H, d, J=8Hz), 7.06(1H, t, J=8Hz), 4.56(1H, q, J=9Hz), 4.05(2H, q, J=7Hz), 2.90–3.10(2H, m), 2.70–2.95(1H, m), 2.20(1H, dd, J=14,5Hz), 2.02(1H, dd, J=14,9Hz), 1.35–1.60(2H, m), 1.28(3H, t, J=7Hz), 0.95–1.20(1H, m), 0.85(3H, s), 0.83(3H, s)

Example 101

Preparation of
3S-4[-(N-hydroxyamino)-2R-isobutylsuccinyl]-amino-1-methoxymethoxyethoxy-3,4-dihydrocarbostyril After conducting a reaction between the compound of Reference Example 89 and a corresponding starting material, the captioned compound was obtained in the same manner as in Example 1.

NMR(270MHz, DMSO-d$_6$)δppm: 10.38(1H, s), 8.70(1H, brs), 8.37(1H, d, J=8Hz), 7.20–7.40(3H, m), 7.06(1H, td,J=7.2Hz), 4.62(2H, s), 4.50–4.70(1H, m), 4.15–4.25(2H, m), 3.60–3.80(2H, m), 3.28(3H, s), 2.85–3.15(2H, m), 2.70–2.90(1H, m), 2.17(1H, dd, J=14.6Hz), 2.01(1H, dd, J=14.8Hz), 1.40–1.75(2H, m), 0.95–1.20(1H, m), 0.89(3H, d, J=6Hz), 0.85(3H, d, J=6Hz)

Example 102

Preparation of
3S-[4-(N-hydroxyamino)-2R-isobutylsuccinyl]-amino-1,7-dimethoxy-3,4-dihydrocarbostyril After conducting a reaction between the compound of Reference Example 90 and a corresponding starting material, the captioned compound was obtained in the same manner as in Example 1.

NMR(270MHz, DMSO-d$_6$)δppm: 10.39(1H, s), 8.73(1H, s), 8.36(1H, d, J=8Hz), 7.19(1H, d, J=8Hz), 6.60–6.70(2H, m), 4.57(1H, q, J=10Hz), 3.82(3H, s), 3.77(3H, s), 2.89(2H, d, J=9Hz), 2.70–2.90(1H, m), 2.16(1H, dd, J=14,7Hz), 2.01(1H, dd, J=14,8Hz), 1.40–1.75(2H, m), 1.00–1.20(1H, m), 0.89(3H, d, J=6Hz), 0.85(3H, d, J=6Hz)

Example 103

Preparation of
1-ethoxy-3S-[4-(N-hydroxyamino)-2R-isobutyl-succinyl]amino-7-methoxy-3,4-dihydrocarbostyril After the compound of Reference Example 91 was allowed to react with a corresponding starting material, the captioned compound was obtained in the same manner as in Example 1.

NMR(270MHz, DMSO-d$_6$)δppm: 10.37(1H, s), 8.71(1H, s), 8.32(1H, d, J=5Hz), 7.19(1H, d, J=8Hz), 6.55–6.70(2H, m), 4.54(1H, q, J=10Hz), 4.04(2H, q, J=7Hz), 3.77(3H, s), 2.70–3.99(3H, m), 2.16(1H, dd, J=14,7Hz), 2.01(1H, dd, J=14.8Hz), 1.35–1.70(2H, m), 1.28(3H, t, J=7Hz), 1.00–1.20(1H, m), 0.89(3H, d, J=7Hz), 0.85(3H, d, J=7Hz)

Example 104

Preparation of
3S-[4-(N-hydroxyamino)-2R-isobutylsuccinyl]-
amino-1-methoxyethyl-6,7-methylenedioxy-
3,4-dihydrocarbostyril After conducting a reaction between the compound obtained by treating the compound of Reference Example 92 with trifluoroacetic acid and a corresponding starting material, the reaction was carried out in the same manner as in Example 1, and the reaction product was purified by high-performance liquid chromatography.

NMR(270MHz, DMSO-$d_6$)δppm: 10.37(1H, s), 8.71(1H, s), 8.17(1H, d, J=8Hz), 6.98(1H, s), 6.87(1H, s), 5.99(2H, s), 4.40–4.37(1H, m), 4.00(2H, t, J=6Hz), 3.48(2H, t, J=6Hz), 3.23(3H, s), 2.80–2.75(3H, m), 2.17(1H, dd, $J_1$=7Hz, $J_2$=15Hz), 2.00(1H, dd, $J_1$=8Hz, $J_2$=14Hz), 1.63–1.61(1H, m), 1.47–1.44(1H, m), 1.12–1.06(1H, m), 0.87(6H, dd, $J_1$=6Hz, $J_2$=14Hz)

Example 105

Preparation of
3R-[4-(N-hydroxyamino)-2R-isobutylsuccinyl]-
amino-1-methoxyethyl-6,7-methylenedioxy-
3,4-dihydrocarbostyril After conducting a reaction between the compound obtained by treating the compound of Reference Example 92 with trifluoroacetic acid and a corresponding starting material, the reaction was carried out in the same manner as in Example 1, and the reaction product was purified by high-performance liquid chromatography.

NMR(270MHz, DMSO-$d_6$)δppm: 10.40(1H, s), 8.74(1H, s), 8.35(1H, d, J=8Hz), 6.98(1H, s), 6.88(1H, s), 5.99(2H, s), 4.40–4.32(1H, m), 4.01(2H, t, J=5Hz), 3.48(2H, t, J=5Hz), 3.23(3H, s), 2.83–2.75(3H, m), 2.20(1H, dd, $J_1$=5Hz, $_2$=15Hz), 2.01(1H, dd, $J_1$=9Hz, $J_2$=14Hz), 1.50–1.43(2H, m), 1.09–1.05(1H, m), 0.83(6H, dd, $J_1$=3Hz, $J_2$=6Hz)

Example 106

Preparation of
3s-[4-(N-benzoyloxyamino)-2R-isobutylsuccinyl]-
amino-1-methoxyethoxymethyl-3,4-dihydrocarbostyril Using a corresponding starting material, the captioned compound was obtained in the same manner as in Example 8.

NMR(270MHz, DMSO-$d_6$)δppm: 11.95(1H, bs), 8.35(1H, d, J=8Hz), 8.03(2H, d, J=7Hz), 7.76(1H, t, J=7Hz), 7.60(2H, t, J=8Hz), 7.30–7.25(3H, m), 7.07(1H, dt, $J_1$=2Hz, $J_2$=8Hz), 5.57(1H, d, J=11Hz), 5.03(1H, d, J=11Hz), 4.59–4.49(1H, m), 3.60(2H, dd, $J_1$=4Hz, $J_2$=6Hz), 3.44(2H, dd, $J_1$=4Hz, $J_2$=6Hz), 3.22(3H, s), 3.01–2.93(2H, m), 2.87–2.82(1H, m), 2.44(1H, dd, $J_1$=7Hz, $J_2$=15Hz), 2.27(1H, dd, $J_1$=7Hz, $J_2$=15Hz), 1.71–1.53(2H, m) 1.27–1.21(1H, m), 0.90(6H, dd, $J_1$=6Hz, $J_2$=13Hz)

Example 107

Preparation of
3S-[4-(N-benzoyloxyamino)-2R-isobutylsuccinyl]-
amino-1-methoxymethyl-3,4-dihydrocarbostyril Using a corresponding starting material, the captioned compound was obtained in the same manner as in Example 8.

NMR(270MHz, DMSO-$d_6$)δppm: 11.95(1H, bs), 8.36(1H, d, J=8Hz), 8.03(2H, d, J=7Hz), 7.76(1H, t, J=7Hz), 7.60(2H, t, J=8Hz), 7.32–7.22(3H, m), 7.07(1H, t, J=7Hz), 5.49(1H, d, J=11Hz), 5.01(1H, d, J=10Hz), 4.58–4.50(1H, m), 3.27(3H, s), 3.02–2.94(2H, m), 2.87–2.82(1H, m), 2.44(1H, dd, $J_1$=7Hz, $J_2$=15Hz), 2.27(1H, dd, $J_1$=7Hz, $J_2$=15Hz), 1.69–1.53(2H, m), 1.27–1.17(1H, m), 0.902(6H, dd, $J_1$=6Hz, $P_2$=13Hz)

Example 108

Preparation of
3S-[4-(N-hydroxyamino)-2R-isobutylsuccinyl]-
amino-6,7-dimethoxy-1-methoxymethyl-
3,4-dihydrocarbostyril After conducting a reaction between the compound of Reference Example 93 and a corresponding starting material, the captioned compound was obtained in the same manner as in Example 1.

NMR(270MHz, DMSO-$d_6$)δppm: 10.38(1H, s), 8.71(1H, s), 8.25(1H, d, J=8Hz), 6.91(1H, s), 6.86(1H, s), 5.48(1H, d, J=10Hz), 5.01(1H, d, J=10Hz), 4.48(1H, dt, J=11,8Hz), 3.75(3H, s), 3.74(3H, s), 3.26(3H, s), 2.80–2.91(3H, m),2.18(1H, dd, J=7,8Hz), 2.02(1H, dd, J=7,8Hz), 1.60–1.67(1H, m), 1.43–1.54(1H, m), 1.03–1.13(1H, m), 0.87(6H, dd, J=14,7Hz)

Example 109

Preparation of
3S-[4-(N-hydroxyamino)-2R-isobutylsuccinyl]-
amino-6,7-dimethoxy-3,4-dihydrocarbostyril After conducting a reaction between the compound of Reference Example 94 and a corresponding starting material, the captioned compound was obtained in the same manner as in Example 1.

NMR(270MHz, DMSO-$d_6$)δppm: 10.38(1H, s), 9.97(1H, s), 8.74(1H, s), 8.12(1H, d, J=8Hz), 6.83(1H, s), 6.53(1H, s), 4.41(1H, dt, J=11,8Hz), 3.70(6H, s), 2.76–2.89(3H, m), 2.17(1H, dd, J=8,7Hz), 2.01(1H, dd, J=8,7Hz), 1.57–1.65(1H, m), 1.42–1.52(1H, m), 1.03–1.13(1H, m), 0.86(6H, dd, J=14,7Hz)

Example 110

Preparation of
3S-[4-(N-hydroxyamino)-2R-isobutylsuccinyl]-
amino-8-methoxy-1-methoxyethyl-
3,4-dihydrocarbostyril After conducting a reaction between the compound of Reference Example 95 and a corresponding starting material, the captioned compound was obtained in the same manner as in Example 1.

NMR(270MHz, DMSO-$d_6$)δppm: 10.35(1H, s), 8.69(1H, s), 8.16(1H, d, J=8Hz), 7.12–7.01(2H, m), 6.88(1H, d, J=7Hz), 4.34–4.21(2H, m), 4.01–3.94(1H, m), 3.84(3H, s), 3.45–3.26(2H, m), 3.11(3H, s), 2.85–2.74(3H, m), 2.16(1H, dd, J$_1$=7Hz, J$_2$=15Hz), 2.00(1H, dd, J$_1$=8Hz, J$_2$=14Hz), 1.64–1.59(1H, m), 1.52–1.42(1H, m), 1.13–1.03(1H, m), 0.87(6H, dd, J$_1$=6Hz, J$_2$=16Hz)

Example 111

Preparation of 3S-[4-(N-benzoyloxyamino)-2R-isobutylsuccinyl]-amino-1-methoxy-3,4-dihydrocarbostyril Using a corresponding starting material, the captioned compound was obtained in the same manner as in Example 8.

NMR(270MHz, DMSO-d$_6$)δppm: 12.00(1H, brs), 3.46(1H, d, J=8Hz), 8.02(2H, d, J=7Hz), 7.75(1H, t, J=7Hz), 7.60(2H, t, J=7Hz), 7.35(1H, d, J=7Hz), 7.28(1H, d, J=7Hz), 7.16(1H, d, J=7Hz), 7.07(1H, t, J=7Hz), 4.64(1H, q, J=10Hz), 3.83(3H, s), 2.90–3.10(2H, m), 2.70–2.95(1H, m), 2.41(1H, dd, J=15,7Hz), 2.26(1H, dd, J=15,7Hz), 1.40–1.80(2H, m), 1.10–1.35(1H, m), 0.92(3H, d, J=6Hz), 0.88(3H, d, J=6Hz)

Example 112

Preparation of 3-[4-(N-hydroxyamino)-2R-isobutylsuccinyl]-amino-1-methoxyethyl-6,7-methylendioxy-3,4-dihydrocarbostyril After conducting a reaction between the compound obtained by treating the compound of Reference Example 92 with trifluoroacetic acid and a corresponding starting material, the captioned compound was obtained (diastereomer, 1:1 mixture) in the same manner as in Example 1.

NMR(270MHz, DMSO-d$_6$)δppm: 10.39+10.36(1H, s), 8.73+8.70(1H, s), 8.35+8.16(1H, d, J=8Hz), 6.98(1H, s), 6.88+6.86(1H, s), 5.99(2H, s), 4.40–4.35(1H, m), 4.01–4.00(2H, m), 3.48(2H, t, J=6Hz), 3.31+3.23(3H, s), 2.80–2.75(3H, m), 2.24–2.13(1H, m), 2.05–1.97(1H, m), 1.73–1.40(2H, m), 1.07–1.05(1H, m), 0.91–0.82(6H, m)

Example 113

Preparation of 3S-[4-(N-hydroxyamino)-2R-isobutylsuccinyl]-amino-1-methoxyethoxy-3,4-dihydrocarbostyril After conducting a reaction between the compound of Reference Example 96 and a corresponding starting material, the captioned compound was obtained in the same manner as in Example 1.

NMR(270MHz, DMSO-d$_6$)δppm: 10.38(1H, brs), 8.72(1H, brs), 8.37(1H, d, J=8Hz), 7.26–7.36(3H, m), 7.06(1H, t, J=7Hz), 4.61(1H, dt, J=11,8Hz), 4.13–4.16(2H, m), 3.60–3.61(2H, m), 3.29(3H, s), 2.99(1H, d, J=11Hz), 2.92(1H, d, J=8Hz), 2.73–2.77(1H, m), 2.17(1H, dd, J=14, 6Hz), 2.01(1H, dd, J=14,8Hz), 1.61–1.67(1H, m), 1.43–1.53(1H, m), 1.06–1.15(1H, m), 0.87(6H, dd, J=13, 7Hz)

Example 114

Preparation of 3S-[4-(N-hydroxyamino)-2R-isobutylsuccinyl]-amino-1-methoxyethoxymethoxyethoxy-3,4-dihydrocarbostyril After conducting a reaction between the compound of Reference Example 97 and a corresponding starting material, the captioned compound was obtained in the same manner as in Example 1.

NMR(270MHz, DMSO-d$_6$)δppm: 10.38(1H, s), 8.72(1H, s), 8.37(1H, d, J=8Hz), 7.20–7.40(3H, m), 7.06(1H, td, J=7,2Hz), 4.68(2H, s), 4.50–4.80(1H, m), 4.18(2H, t, J=4Hz), 3.76(2H, m), 3.60(2H, m), 3.47(2H, m), 3.24(3H, s), 2.85–3.10(2H, m), 2.70–2.85(1H, m), 2.17(1H, dd, J=14, 7Hz), 2.01(1H, dd, J=10,8Hz), 1.35–1.75(2H, m), 1.00–1.20(1H, m), 0.89(3H, d, J=7Hz), 0.85(3H, d, J=7Hz)

Example 115

Preparation of 3S-[4-(N-hydroxyamino)-2R-isobutylsuccinyl]-amino-1-methoxyethoxyethoxy-3,4-dihydrocarbostyril After conducting a reaction between the compound of Reference Example 98 and a corresponding starting material, the captioned compound was obtained in the same manner as in Example 1.

NMR(270MHz, DMSO-d$_6$)δppm: 10.38(1H, s), 8.71(1H, s), 8.35(1H, d, J=8Hz), 7.20–7.45(3H, m), 7.06(1H, t, J=7Hz), 4.61(1H, dt, J=13,8Hz), 4.15(2H, dd, J=5,3Hz), 3.68(2H, d, J=3Hz), 3.40–3.60(4H, m), 3.28(3H, s), 2.85–3.15(2H, m), 2.65–2.85(1H, m), 2.17(1H, dd, J=15, 6Hz), 2.01(1H, dd, J=15,8Hz), 1.35–1.75(2H, m), 0.95–1.20(1H, m), 0.89(3H, d, J=7Hz), 0.85(3H, d, J=7Hz)

Example 116

Preparation of 3S-[4-(N-hydroxyamino)-2R-hexylsuccinyl]-amino-1-methoxy-3,4-dihydrocarbostyril After conducting a reaction of a corresponding starting material, the captioned compound was obtained in the same manner as in Example 1.

NMR(270MHz, DMSO-d$_6$)δppm: 10.37(1H, s), 8.70(1H, s), 8.32(1H, d, J=8Hz), 7.35(1H, d, J=8Hz), 7.29(1H, d, J=8Hz), 7.16(1H, d, J=8Hz), 7.07(1H, t, J=8Hz), 4.61(1H, dt, J=11,8Hz), 3.82(3H, s), 2.85–3.10(2H, m), 2.55–2.80(1H, m), 2.19(1H, dd, J=14,7Hz), 2.02(1H, dd, J=14,8Hz), 1.10–1.60(10H, m), 0.87(3H, t, J=7Hz)

Example 117

Preparation of 3S-[4-(N-hydroxyamino)-2R-isobutylsuccinyl]-amino-1-methyl-6,7-methylenedioxy-3,4-dihydrocarbostyril After conducting a reaction between the compound of Reference Example 112 and a corresponding starting material, the captioned compound was obtained in the same manner as in Example 1.

NMR (270MHz, DMSO-d$_6$)δppm: 10.38 (1H, s), 8.71 (1H, s), 8.17 (1H, d, J=8Hz), 6.88 (1H, s), 6.86 (1H, s), 5.99 (2H, s), 4.37 (1H, dt, J$_1$=8Hz, J$_2$=17Hz), 3.23 (3H, s), 2.65–2.90 (3H, m), 2.16 (1H, dd, J$_1$=6Hz, J$_2$=14Hz), 2.00

(1H, dd, $J_1$=7Hz, $J_2$=14Hz), 1.35–1.80 (2H, m), 0.95–1.20 (1H, m), 0.89 (3H, d, J=7Hz), 0.84 (3H, d, J=7Hz)

Example 118

Preparation of
1-ethyl-3S-[4-(N-hydroxyamino)-2R-isobutyl-succinyl]amino-6,7-methylenedioxy-3,4-dihydrocarbostyril After conducting a reaction between the compound of Reference Example 113 and a corresponding starting material, the captioned compound was obtained in the same manner as in Example 1.

NMR (270MHz, DMSO-$d_6$) δppm: 10.37 (1H, s), 8.70 (1H, s), 8.14 (1H, d, J=8Hz), 6.89 (1H, s), 6.87 (1H, s), 5.99 (2H, s), 4.36 (1H, q, J=9Hz), 3.84 (2H, q, J=7Hz), 2.70–2.85 (3H, m), 2.17 (1H, dd, $J_1$=7Hz, $J_2$=14Hz), 2.01 (1H, dd, $J_1$=7Hz, $J_2$=14Hz), 1.40–1.75 (2H, m), 0.89 (3H, d, J=7Hz), 0.84 (3H, d, J=7Hz)

Example 119

Preparation of
1-carboxymethyl-3S-[4-(N-hydroxyamino)-2R-isobutylsuccinyl]amino-6,7-methylenedioxy-3,4-dihydrocarbostyril After conducting a reaction between the compound of Reference Example 111 and a corresponding starting material, the captioned compound was obtained in the same manner as in Example 1.

NMR (270MHz, DMSO-$d_6$) δppm: 10.38 (1H, s), 8.71 (1H, s), 8.23 (1H, d, J=8Hz), 6.88 (1H, s), 6.71 (1H, s), 5.98 (2H, s), 4.61 (1H, d, J=17Hz), 4.30–4.50 (1H, m), 4.40 (1H, d, J=17Hz), 2.70–3.00 (3H, m), 2.18 (1H, dd, $J_1$=7Hz, $J_2$=14Hz), 2.01 (1H, dd, $J_1$=7Hz, $J_2$=14H z), 1.35–1.80 (2H, m), 0.95–1.25 (1H, m), 0.89 (3H, d, J=6Hz), 0.84 (3H, d, J=6Hz)

Example 120

Preparation of
1-carbamoylmethyl-3S-[4-(N-hydroxyamino)-2R-isobutylsuccinyl]amino-6,7-methylenedioxy-3,4-dihydrocarbostyril After conducting a reaction between the compound of Reference Example 110 and a corresponding starting material, the captioned compound was obtained in the same manner as in Example 1.

NMR (270MHz, DMSO-$d_6$) δppm: 10.38 (1H, s), 8.73 (1H, s), 8.19 (1H, d, J=8Hz), 7.54 (1H, s), 7.18 (1H, s), 6.88 (1H, s), 6.56 (1H, s), 5.98 (2H, s), 4.56 (1H, d, J=7Hz), 4.45–4.60 (1H, m), 4.23 (1H, d, J=7Hz), 2.70–2.95 (3H, m), 2.17 (1H, dd, $J_1$=7Hz, $J_2$=14Hz), 2.01 (1H, dd, $J_1$=8Hz, $J_2$=14Hz), 1.35–1.80 (2H, m), 0.95–1.20 (1H, m), 0.89 (3H, d, J=6Hz), 0.84 (3H, d, J=6Hz)

Example 121

Preparation of
3S-[4-(N-hydroxyamino)-2R-isobutylsuccinyl]-amino-1-methoxymethyl-6,7-methylenedioxy-3,4-dihydrocarbostyril After conducting a reaction between the compound of Reference Example 100 and a corresponding starting material, the captioned compound was obtained in the same manner as in Example 1.

NMR (270MHz, DMSO-$d_6$) δppm: 10.38 (1H, brs), 8.71 (1H, brs), 8.24 (1H, d, J=8Hz), 6.89 (2H, s), 5.99 (2H, d, J=3Hz), 5.42 (1H, d, J=10Hz), 4.98 (1H, d, J=10Hz), 4.46 (1H, dt, $J_1$=8Hz, $J_2$=16Hz), 3.24 (3H, s), 2.73–2.84 (3H, m), 2.17 (1H, dd, $J_1$=7Hz, $J_2$=15Hz), 2.01 (1H, dd, $J_1$=8Hz, $J_2$=15Hz), 1.60–1.70 (1H, m), 1.43–1.53 (1H, m), 1.07–1.16 (1H, m), 0.89 (3H, d, J=7Hz), 0.84 (3H, d, J=7Hz)

Example 122

Preparation of
1-ethyl-3S-[4-(N-hydroxyamino)-3S-methyl-2R-isobutylsuccinyl]amino-6,7-methylenedioxy-3,4-dihydrocarbostyril After conducting a reaction between the compound of Reference Example 113 and a corresponding starting material, the captioned compound was obtained in the same manner as in Example 14.

NMR (270MHz, DMSO-$d_6$) δppm: 10.48 (1H, s), 8.76 (1H, s), 8.34 (1H, d, J=8Hz), 6.89 (2H, s), 5.99 (2H, s), 4.43 (1H, dt, $J_1$=6Hz, $J_2$=13Hz), 3.87 (2H, q, J=7Hz), 2.70–2.90 (2H, m), 2.40–2.60 (1H, m), 2.16 (1H, dd, $J_1$=7Hz, $J_2$=10Hz), 1.45–1.70 (1H, m), 1.45 (1H, t, J=12Hz), 1.09 (3H, t, J=7Hz), 0.95 (3H, d, J=7Hz), 0.75–1.00 (1H, m), 0.87 (3H, d, J=6Hz), 0.81 (3H, d, J=6Hz)

Example 123

Preparation of
3S-[4-(N-hydroxyamino)-2R-isobutylsuccinyl]-amino-6,7-methylenedioxy-1-propyl-3,4-dihydrocarbostyril After conducting a reaction between the compound of Reference Example 109 and a corresponding starting material, the captioned compound was obtained in the same manner as in Example 1.

NMR (270MHz, DMSO-$d_6$) δppm: 10.38 (1H, s), 8.73 (1H, s), 8.16 (1H, d, J=8Hz), 6.90 (1H, s), 6.88 (1H, s), 5.99 (2H, s), 4.37 (1H, q, J=9Hz), 3.65–4.00 (2H, m), 2.70–2.90 (3H, m), 2.16 (1H, dd, $J_1$=7Hz, $J_2$=14Hz), 2.00 (1H, dd, $J_1$=7Hz, $J_2$=14Hz), 1.00–1.75 (5H, m), 0.80–0.95 (9H, m)

Example 124

Preparation of
1-hexyloxymethyl-3S-[4-(N-hydroxyamino)-2R-isobutylsuccinyl]amino-6,7-methylenedioxy-3,4-dihydrocarbostyril After conducting a reaction between the compound of Reference Example 101 and a corresponding starting material, the captioned compound was obtained in the same manner as in Example 1.

NMR (270MHz, DMSO-$d_6$) δppm: 10.38 (1H, brs), 8.71 (1H, brs), 8.23 (1H, d, J=8Hz), 6.91 (1H, s), 6.88 (1H, s), 5.99 (2H, d, J=2Hz), 5.47 (1H, d, J=11Hz), 4.99 (1H, d, J=11Hz), 4.47–4.42 (1H, m), 3.42 (2H, t, J=6Hz), 2.87–2.79 (3H, m), 2.17 (1H, dd, $J_1$=7Hz, $J_2$=15Hz), 2.01 (1H, dd, $J_1$=8Hz, $J_2$=15Hz), 1.64–1.44 (4H, m), 1.26–1.07 (7H, m), 0.90–0.79 (9H, m)

Example 125

Preparation of
3S-[4-(N-hydroxyamino)-2R-isobutylsuccinyl]-
amino-6,7-methylenedioxy-3,4-dihydrocarbostyril After conducting a reaction between the compound of Reference Example 99 and a corresponding starting material, the captioned compound was obtained in the same manner as in Example 1.

NMR (270MHz, DMSO-$d_6$) δppm: 10.37 (1H, brs), 10.01 (1H, brs), 8.71 (1H, brs), 8.11 (1H, d, J=8Hz), 6.81 (1H, s), 6.48 (1H, s), 5.94 (2H, d, J=3Hz), 4.44–4.33 (1H, m), 2.83–2.79 (3H, m), 2.17 (1H, dd, $J_1$=6Hz, $J_2$=14Hz), 2.01 (1H, dd, $J_1$=8Hz, $J_2$=14Hz), 1.62–1.44 (2H, m), 1.12–1.07 (1H, m), 0.88 (3H, d, J=6Hz), 0.84 (3H, d, J=6Hz)

Example 126

Preparation of
3S-[4-(N-hydroxyamino)-2R-isobutylsuccinyl]-
amino-1-methoxyethoxymethyl-6,7-methylenedioxy-
3,4-dihydrocarbostyril After conducting a reaction between the compound of Reference Example 102 and a corresponding starting material, the captioned compound was obtained in the same manner as in Example 1.

NMR (270MHz, DMSO-$d_6$) δppm: 10.38 (1H, brs), 8.71 (1H, brs), 8.23 (1H, d, J=8Hz), 6.93 (1H, s), 6.88 (1H, s), 6.00 (2H, d, J=2Hz), 5.51 (1H, d, J=11Hz), 4.97 (1H, d, J=11Hz), 4.44 (1H, dt, $J_1$=8Hz, $J_2$=16Hz), 3.57 (2H, dd, $J_1$=4Hz, $J_2$=7Hz), 3.44 (2H, dd, $J_1$=4Hz, $J_2$=7Hz), 3.23 (3H, s), 2.75–2.86 (3H, m), 2.17 (1H, dd, $J_1$=7Hz, $J_2$=15Hz), 2.01 (1H, dd, $J_1$=8Hz, $J_2$=15Hz), 1.59–1.65 (1H, m), 1.43–1.53 (1H, m), 1.02–1.12 (1H, m), 0.89 (1H, d, J=7Hz), 0.84 (1H, d, J=7Hz)

Example 127

Preparation of
3S-[4-(N-hydroxyamino)-2R-isobutylsuccinyl]-
amino-1-methoxymethoxyethyl-6,7-methylenedioxy-
3,4-dihydrocarbostyril After conducting a reaction between the compound of Reference Example 103 and a corresponding starting material, the captioned compound was obtained in the same manner as in Example 1.

NMR (270MHz, DMSO-$d_6$) δppm: 10.37 (1H, brs), 8.71 (1H, brs), 8.18 (1H, d, J=8Hz), 6.99 (1H, s), 6.87 (1H, s), 6.00 (2H, s), 4.52 (2H, d, J=6Hz), 4.39 (1H, dt, $J_1$=8Hz, $J_2$=16Hz), 4.01–4.11 (2H, m), 3.58–3.62 (2H, m), 3.17 (3H, s), 2.77–2.81(3H, m), 2.16 (1H, dd, $J_1$=7Hz, $J_2$=15Hz), 2.00 (1H, dd, $J_1$=8Hz, $J_2$=15Hz), 1.59–1.64 (1H, m), 1.42–1.48 (1H, m), 1.02–1.12 (1H, m), 0.89 (1H, d, J=7Hz), 0.84 (1H, d, J=7Hz)

Example 128

Preparation of
3S-[4-(N-hydroxyamino)-2R-isobutylsuccinyl]-
amino-1-(4-methoxybenzyl)-6,7-methylenedioxy-
3,4-dihydrocarbostyril After conducting a reaction between the compound of Reference Example 104 and a corresponding starting material, the captioned compound was obtained in the same manner as in Example 1.

NMR (270MHz, DMSO-$d_6$) δppm: 10.38 (1H, brs), 8.72 (1H, brs), 8.26 (1H, d, J=8Hz), 7.14 (2H, d, J=9Hz), 6.88 (1H, s), 6.87 (2H, d, J=9Hz), 6.74 (1H, s), 5.93 (2H, s), 5.13 (1H, d, J=17Hz), 4.98 (1H, d, J=17Hz), 4.53 (1H, dt, $J_1$=8Hz, $J_2$=12Hz), 3.71 (3H, s), 2.84 (3H, m), 2.19 (1H, dd, $J_1$=7Hz, $J_2$=15Hz), 2.02 (1H, dd, $J_1$=8Hz, $J_2$=15Hz), 1.59–1.69 (1H, m), 1.44–1.54 (1H, m), 1.03–1.13 (1H, m), 0.90 (1H, d, J=7Hz), 0.84 (1H, d, J=7Hz)

Example 129

Preparation of
3S-[3-benzyl-4-(N-hydroxyamino)-2R-isobutyl-
succinyl]amino-1-ethyl-6,7-methylenedioxy-
3,4-dihydrocarbostyril After conducting a reaction between the compound of Reference Example 113 and a corresponding starting material, the captioned compound was obtained in the same manner as in Example 14.

NMR (270MHz, DMSO-$d_6$) δppm: 10.28 (1H, brs), 8.64 (1H, brs), 8.46 (1H, d, J=8Hz), 7.27–7.05 (5H, m), 6.90 (2H, s), 5.98 (2H, d, J=3 Hz), 4.51–4.41 (1H, m), 3.88 (2H, q, J=7Hz), 2.95–2.70 (3H, m), 2.62–2.40 (3H, m), 1.63–1.47 (2H, m), 1.10 (3H, t, J=7Hz), 1.01–0.96 (1H, m), 0.89 (3H, d, J=6Hz), 0.82 (3H, d, J=7Hz)

Example 130

Preparation of
1-ethoxyethyl-3S-[4-(N-hydroxyamino)-
2R-isobutylsuccinyl]amino-6,7-methylenedioxy-
3,4-dihydrocarbostyril After conducting a reaction between the compound of Reference Example 105 and a corresponding starting material, the captioned compound was obtained in the same manner as in Example 1.

NMR (270MHz, DMSO-$d_6$) δppm: 10.38 (1H, brs), 8.72 (1H, brs), 8.18 (1H, d, J=8Hz), 7.01 (1H, s), 6.87 (1H, s), 5.99 (2H, s), 4.40–4.36 (1H, m), 4.02–3.93 (2H, m), 3.53–3.39 (4H, m), 2.80–2.77 (3H, m), 2.17 (1H, dd, $J_1$=6Hz, $J_2$=14Hz), 2.00 (1H, dd, $J_1$=8Hz, $J_2$=15Hz), 1.65–1.48 (2H, m), 1.06 (3H, t, J=7Hz), 1.12–1.03 (1H, m), 0.89 (3H, d, J=7Hz), 0.84 (3H, d, J=7Hz)

Example 131

Preparation of
1-hexyl-3S-[4-(N-hydroxyamino)-2R-isobutyl-
succinyl]amino-6,7-methylenedioxy-
3,4-dihydrocarbostyril After conducting a reaction between the compound of Reference Example 106 and a corresponding starting material, the captioned compound was obtained in the same manner as in Example 1.

NMR (270MHz, DMSO-$d_6$) δppm: 10.37 (1H, brs), 8.72 (1H, brs), 8.16 (1H, d, J=8Hz), 6.88 (2H, d, J=2Hz), 6.00 (2H, s), 4.38–4.31 (1H, m), 3.92–3.89 (1H, m), 3.77–3.74 (1H, m), 2.80–2.77 (3H, m), 2.16 (1H, dd, $J_1$=6Hz, $J_2$=14Hz), 2.00 (1H, dd, $J_1$=8Hz, $J_2$=15Hz), 1.63–1.45 (4H, m), 1.26–1.25 (6H, m), 1.12–1.07 (1H, m), 0.90–0.83 (9H, m)

Example 132

Preparation of 3S-[4-(N-hydroxyamino)-2R-isobutylsuccinyl]amino-1-phenethyl-6,7-methylenedioxy-3,4-dihydrocarbostyril After conducting a reaction between the compound of Reference Example 107 and a corresponding starting material, the captioned compound was obtained in the same manner as in Example 1.

NMR (270MHz, DMSO-$d_6$) δppm: 10.38 (1H, brs), 8.71 (1H, brs), 8.14 (1H, d, J=8Hz), 7.18–7.32 (5H, m), 6.94 (1H, s), 6.88 (1H, s), 6.00 (2H, s), 4.38 (1H, dt, $J_1$=8Hz, $J_2$=16Hz), 4.00–4.13 (2H, m), 2.72–2.83 (5H, m), 2.17 (1H, dd, $J_1$=7Hz, $J_2$=15Hz), 2.01 (1H, dd, $J_1$=8Hz, $J_2$=15Hz), 1.57–1.63 (1H, m), 1.42–1.48 (1H, m), 1.03–1.13 (1H, m), 0.89 (1H, d, J=7Hz), 0.84 (1H, d, J=7Hz)

Example 133

Preparation of 1-ethyl-3S-[4-(N-hydroxyamino)-2R-hexylsuccinyl]amino-6,7-methylenedioxy-3,4-dihydrocarbostyril After conducting a reaction between the compound of Reference Example 113 and a corresponding starting material, the captioned compound was obtained in the same manner as in Example 78.

NMR (270MHz, DMSO-$d_6$) δppm: 10.36 (1H, s), 8.69 (1H, s), 8.11 (1H, d, J=8Hz), 6.89 (1H, s), 6.88 (1H, s), 5.99 (2H, s), 4.36 (1H, dt, $J_1$=8Hz, $J_2$=12Hz), 3.87 (2H, q, J=7Hz), 2.60–2.85 (3H, m), 2.19 (1H, dd, $J_1$=7Hz, $J_2$=14Hz), 2.02 (1H, dd, $J_1$=7Hz, $J_2$=14Hz), 1.15–1.60 (10H, m), 1.09 (3H, t, J=7Hz), 0.86 (3H, t, J=7Hz)

Example 134

Preparation of 3S-[4-(N-hydroxyamino)-2R-hexylsuccinyl]amino-1-methoxyethyl-6,7-methylenedioxy-3,4-dihydrocarbostyril After conducting a reaction between the compound of Reference Example 92 and a corresponding starting material, the captioned compound was obtained in the same manner as in Example 78.

NMR (270MHz, DMSO-$d_6$) δppm: 10.37 (1H, s), 8.70 (1H, s), 8.15 (1H, d, J=8Hz), 6.98 (1H, s), 6.87 (1H, s), 5.99 (2H, s), 4.38 (1H, q, J=10Hz), 3.90–4.10 (2H, m), 3.40–3.55 (2H, m), 3.23 (3H, s), 2.78 (2H, d, J=10Hz), 2.60–2.75 (1H, m), 2.19 (1H, dd, $J_1$=7Hz, $J_2$=14Hz), 2.04 (1H, dd, $J_1$=7Hz, $J_2$=14Hz), 1.15–1.60 (10H, m), 0.86 (3H, t, J=6Hz)

Example 135

Preparation of 1-ethyl-3S-[4-(N-hydroxyamino)-2R-heptylsuccinyl]amino-6,7-methylenedioxy-3,4-dihydrocarbostyril After conducting a reaction between the compound of Reference Example 113 and a corresponding starting material, the captioned compound was obtained in the same manner as in Example 78.

NMR (270MHz, DMSO-$d_6$) δppm: 10.37 (1H, s), 8.70 (1H, s), 8.11 (1H, d, J=8Hz), 6.90 (1H, s), 6.88 (1H, s), 6.00 (2H, s), 4.37 (1H, dt, $J_1$=8Hz, $J_2$=12Hz), 3.87 (2H, q, J=7Hz), 2.60–2.90 (3H, m), 2.19 (1H, dd, $J_1$=7Hz, $J_2$=14Hz), 2.02 (1H, dd, $J_1$=8Hz, $J_2$=14Hz), 1.15–1.60 (12H, m), 1.09 (3H, t, J=7Hz), 0.86 (3H, t, J=7Hz)

Example 136

Preparation of 1-ethyl-3S-[4-(N-hydroxyamino)-2R-pentylsuccinyl]amino-6,7-methylenedioxy-3,4-dihydrocarbostyril After conducting a reaction between the compound of Reference Example 113 and a corresponding starting material, the captioned compound was obtained in the same manner as in Example 78.

NMR (270MHz, DMSO-$d_6$) δppm: 10.37 (1H, s), 8.70 (1H, s), 8.11 (1H, d, J=8Hz), 6.90 (1H, s), 6.88 (1H, s), 6.00 (2H, s), 4.37 (1H, dt, $J_1$=8Hz, $J_2$=12Hz), 3.87 (2H, q, J=7Hz), 2.60–2.90 (3H, m), 2.19 (1H, dd, $J_1$=7Hz, $J_2$=14Hz), 2.02 (1H, dd, $J_1$=8Hz, $J_2$=14Hz), 1.15–1.60 (8H, m), 1.09 (3H, t, J=7Hz), 0.87 (3H, t, J=7Hz)

Example 137

Preparation of 1-ethoxy-3S-[4-(N-hydroxyamino)-2R-hexylsuccinyl]amino-3,4-dihydrocarbostyril After conducting a reaction between the compound of Reference Example 29 and a corresponding starting material, the captioned compound was obtained in the same manner as in Example 78.

NMR (270MHz, DMSO-$d_6$) δppm: 10.37 (1H, s), 8.70 (1H, s), 8.32 (1H, d, J=8Hz), 7.31 (2H, dd, $J_1$=8Hz, $J_2$=16Hz), 7.17 (1H, d, J=8Hz), 7.06 (1H, t, J=8Hz), 4.59 (1H, dt, $J_1$=8Hz, $J_2$=12Hz), 4.05 (2H, q, J=7Hz), 2.85–3.10 (2H, m), 2.60–2.80 (1H, m), 2.19 (1H, dd, $J_1$=7Hz, $J_2$=14Hz), 2.05 (1H, dd, $J_1$=7Hz, $J_2$=14Hz), 1.20–1.60 (13H, m), 0.87 (3H, t, J=7Hz)

Example 138

Preparation of 3S-[4-(N-hydroxyamino)-2R-heptylsuccinyl]amino-1-methoxymethyl-3,4-dihydrocarbostyril After conducting a reaction between the compound of Reference Example 32 and a corresponding starting material, the captioned compound was obtained in the same manner as in Example 78.

NMR (270MHz, DMSO-$d_6$) δppm: 10.37 (1H, s), 8.70 (1H, s), 8.26 (1H, d, J=8Hz), 7.15–7.30 (3H, m), 7.07 (1H, t, J=8Hz), 5.49 (1H, d, J=10Hz), 5.00 (1H, d, J=10Hz), 4.52 (1H, dt, $J_1$=7Hz, $J_2$=13Hz), 3.26 (3H, s), 2.80–3.10 (2H, m), 2.60–2.80 (1H, m), 2.20 (1H, dd, $J_1$=7Hz, $J_2$=14Hz), 2.03 (1H, dd, $J_1$=7Hz, $J_2$=14Hz), 1.15–1.60 (12H, m), 0.86 (3H, t, J=6Hz)

Example 139

Preparation of 3S-[4-(N-hydroxyamino)-2R-pentylsuccinyl]amino-1-methoxy-3,4-dihydrocarbostyril After conducting a reaction of corresponding starting materials, the captioned compound was obtained in the same manner as in Example 78.

NMR (270MHz, DMSO-$d_6$) δppm: 10.37 (1H, s), 8.70 (1H, s), 8.32 (1H, d, J=8Hz), 7.32 (2H, dd, $J_1$=8Hz, $J_2$=16Hz), 7.16 (1H, d, J=8Hz), 7.07 (1H, t, J=8Hz), 4.61 (1H, dt, $J_1$=8Hz, $J_2$=12Hz), 3.82 (3H, s), 2.85–3.10 (2H, m), 2.60–2.80 (1H, m), 2.20 (1H, dd, $J_1$=7Hz, $J_2$=14Hz), 2.03 (1H, dd, $J_1$=7Hz, $J_2$=14Hz), 1.20–1.60 (8H, m), 0.87 (3H, t, J=7Hz)

Example 140

Preparation of
1-ethoxy-3S-[4-(N-hydroxyamino)-2R-pentylsuccinyl]amino-3,4-dihydrocarbostyril After conducting a reaction between the compound of Reference Example 29 and a corresponding starting material, the captioned compound was obtained in the same manner as in Example 78.

NMR (270MHz, DMSO-$d_6$) δppm: 10.38 (1H, s), 8.73 (1H, s), 8.33 (1H, d, J=8Hz), 7.31 (2H, dd, $J_1$=8Hz, $J_2$=16Hz), 7.17 (1H, d, J=8Hz), 7.07 (1H, t, J=8Hz), 4.59 (1H, dt, $J_1$=8Hz, $J_2$=12Hz), 4.05 (2H, q, J=7Hz), 2.90–3.10 (2H, m), 2.60–2.80 (1H, m), 2.19 (1H, dd, $J_1$=7Hz, $J_2$=14Hz), 2.05 (1H, dd, $J_1$=7Hz, $J_2$=14Hz), 1.28 (3H, t, J=7Hz), 1.20–1.60 (8H, m), 0.87 (3H, t, J=7Hz)

Example 141

Preparation of
3S-[4-(N-hydroxyamino)-2R-isobutylsuccinyl]-amino-1-methoxymethoxy-3,4-dihydrocarbostyril After conducting a reaction of corresponding starting materials, the captioned compound was obtained in the same manner as in Example 1.

NMR (270MHz, DMSO-$d_6$) δppm: 10.38 (1H, s), 8.72 (1H, s), 8.40 (1H, d, J=8Hz), 7.15–7.40 (3H, m), 7.07 (1H, t, J=7Hz), 5.07 (1H, d, J=7Hz), 5.03 (1H, d, J=7Hz), 4.56 (1H, dt, J=$J_1$=7Hz, $J_2$=12Hz), 3.49 (3H, s), 2.65–3.15 (3H, m), 2.17 (1H, dd, $J_1$=6Hz, $J_2$=14Hz), 2.01 (1H, dd, $J_1$=8Hz, $J_2$=14Hz), 1.00–1.70 (3H, m), 0.89 (3H, d, J=6Hz), 0.84 (3H, d, J=6Hz)

Example 142

Preparation of
1-ethoxymethyl-3S-[4-(N-hydroxyamino)-2R-isobutylsuccinyl]amino-6,7-methylenedioxy-3,4-dihydrocarbostyril After conducting a reaction between the compound of Reference Example 108 and a corresponding starting material, the captioned compound was obtained in the same manner as in Example 1.

NMR (270MHz, DMSO-$d_6$) δppm: 10.38 (1H, brs), 8.71 (1H, brs), 8.23 (1H, d, J=8Hz), 6.92 (1H, s), 6.88 (1H, s), 6.00 (2H, s), 5.48 (1H, d, J=10Hz), 4.98 (1H, d, J=11Hz), 4.50–4.39 (1H, m), 3.48 (2H, q, J=7Hz), 2.93–2.75 (3H, m), 2.17 (1H, dd, $J_1$=7Hz, $J_2$=15Hz), 2.01 (1H, dd, $J_1$=8Hz, $J_2$=15Hz), 1.64–1.43 (2H, m), 1.10 (3H, t, J=7Hz), 1.13–1.08 (1H, m), 0.89(3H, d, J=7Hz), 0.84 (3H, d, J=7Hz)

PHARMACOLOGICAL STUDIES

Test compounds were as follow:

1. 3S-[4-(N-hydroxyamino)-2R-isobutylsuccinyl]amino-3,4-dihydrocarbostyril
2. 3S-[4-(N-hydroxyamino)-2R-isobutylsuccinyl]amino-7-methoxy-3,4-dihydrocarbostyril
3. 3S-[4-(N-hydroxyamino)-2R-isobutylsuccinyl]amino-1-methoxy-3,4-dihydrocarbostyril
4. 3S-[4-(N-hydroxyamino)-2R-isobutyl-3S-acetylthiomethylsuccinyl]amino-3,4-dihydrocarbostyril
5. 3S-[4-(N-hydroxyamino)-2R-isobutyl-3S-mercaptomethylsuccinyl]amino-3,4-dihydrocarbostyril
6. 3S-[4-(N-hydroxyamino)-2R-isobutyl-3S-(2-thienylthiomethyl)succinyl]amino-3,4-dihydrocarbostyril
7. 3S-[4-(N-hydroxyamino)-2R-isobutyl-3(R or S)-phthalimidomethylsuccinyl]amino-3,4-dihydrocarbostyril
8. 1-ethoxycarbonylmethyl-3S-[4-(N-hydroxyamino)-2R-isobutylsuccinyl]amino-3,4-dihydrocarbostyril
9. 3S-[4-(N-hydroxyamino)-2R-isobutyl-3S-methylsuccinyl]amino-1-methoxy-3,4-dihydrocarbostyril
10. 1-aminocarbonylmethyl-3S-[4-(N-hydroxyamino)-2R-isobutylsuccinyl]amino-3,4-dihydrocarbostyril
11. 3S-[4-(N-hydroxyamino)-2R-isobutylsuccinyl]amino-1-(4-methoxycarbonylbenzyl)-3,4-dihydrocarbostyril
12. 1-ethyl-3S-[4-(N-hydroxyamino)-2R-isobutylsuccinyl]amino-3,4-dihydrocarbostyril
13. 1-allyl-3S-[4-(N-hydroxyamino)-2R-isobutyl-3S-methylsuccinyl]amino-3,4-dihydrocarbostyril
14. 3S-[4-(N-hydroxyamino)-2R-isobutylsuccinyl]amino-1-methoxymethyl-3,4-dihydrocarbostyril
15. 3S-[4-(N-hydroxyamino)-2R-isobutyl-3S-methylsuccinyl]amino-1-(2-propynyl)-3,4-dihydrocarbostyril
16. 1-carboxymethyl-3S-[4-(N-hydroxyamino)-2R-isobutyl-3S-methylsuccinyl]amino-3,4-dihydrocarbostyril
17. 1-ethoxy-3S-[4-(N-hydroxyamino)-2R-isobutylsuccinyl]amino-3,4-dihydrocarbostyril
18. 3S-[4-(N-hydroxyamino)-2R-isobutylsuccinyl]amino-1-methoxyethoxymethyl-3,4-dihydrocarbostyril
19. 3S-[4-(N-hydroxyamino)-2R-isobutylsuccinyl]amino-1-methoxymethoxyethyl-3,4-dihydrocarbostyril
20. 3S-[4-(N-hydroxyamino)-2R-heptylsuccinyl]amino-1-methoxy-3,4-dihydrocarbostyril
21. 3S-[4-(N-hydroxyamino)-2R-isobutylsuccinyl]amino-1-methoxyethyl-3,4-dihydrocarbostyril
22. 3S-[4-(N-hydroxyamino)-2R-ethoxyethylsuccinyl]amino-1-methoxy-3,4-dihydrocarbostyril
23. 3S-[4-(N-hydroxyamino)-2R-isobutyl-3-(3,4-methylenedioxybenzyl)succinyl]amino-1-methoxy-3,4-dihydrocarbostyril
24. 3S-[4-(N-hydroxyamino)-2R-isobutylsuccinyl]amino-1-methoxyethyl-6,7-methylenedioxy-3,4-dihydrocarbostyril
25. 3R-[4-(N-hydroxyamino)-2R-isobutylsuccinyl]amino-1-methoxyethyl-6,7-methylenedioxy-3,4-dihydrocarbostyril
26. 3-[4-(N-hydroxyamino)-2R-isobutylsuccinyl]amino-1-methoxyethyl-6,7-methylendioxy-3,4-dihydrocarbostyril
27. 3S-[4-(N-hydroxyamino)-2R-isobutylsuccinyl]amino-1-methyl-6,7-methylenedioxy-3,4-dihydrocarbostyril
28. 1-ethyl-3S-[4-(N-hydroxyamino)-2R-isobutylsuccinyl]amino-6,7-methylenedioxy-3,4-dihydrocarbostyril
29. 1-ethyl-3S-[4-(N-hydroxyamino)-2R-pentylsuccinyl]amino-6,7-methylenedioxy-3,4-dihydrocarbostyril
30. 3S-[4-(N-hydroxyamino)-2R-pentylsuccinyl]amino-1-methoxy-3,4-dihydrocarbostyril 31.    3S-[4-(N-hydroxyamino)-2R-isobutylsuccinyl]amino-1-methoxymethoxy-3,4-dihydrocarbostyril Pharmacological Test 1

(1) Measuring Method of Stromelysin Inhibiting Activity

Inhibiting of Stromelysin refined from the culture supernatant of mouse colon cancer cell (Colon 26 cell) was measured by using fluorescence labeled casein, according to the method proposed by Miyazaki et al. (J. Biochem., 108, 537–543, 1990), and S. S. Twining [Fed. Proc., 42, 1951 (1984)].

The enzyme was activated by incubating for 2 hours at 37° C. in 1 mM mercury (II) p-aminophenylacetate. The test compound was used by dissolving in dimethyl sulfoxide. The enzyme reaction was started by adding the activated enzyme in a solution of 50 mM TRIS-hydrochloric acid (pH 7.5), 10 mM $CaCl_2$, and 0.1% (v/v) dimethyl sulfoxide containing the test compound and 0.25% (w/v) of fluorescence labeled casein as substrate. The reaction was conducted for 3 hours at 37° C., and stopped by adding an equivalent amount of 5% (w/v) trichloroacetic acid solution. Afterwards, by centrifugal separation for 15 minutes at 3000 rpm, 4° C., the undigested substrate was precipitated, and to 1 part by volume of the obtained supernatant, 4 parts by volume of 0.3M phosphate buffer (pH 8.5) was added, and the fluorescence intensity was measured at 520 nm (Em)/495 nm (Ex), and the decomposition volume was quantitatively determined.

The enzyme inhibiting activity was expressed by the concentration ($IC_{50}$) of the test compound wherein the enzyme activity of known amount was inhibited till 50%. The results are shown in Table 1.

TABLE 1

| Test compound | Stromelysin $IC_{50}$ (M) |
| --- | --- |
| 1 | $5.7 \times 10^{-7}$ |
| 2 | $4.9 \times 10^{-7}$ |
| 3 | $1.3 \times 10^{-6}$ |
| 4 | $8.5 \times 10^{-7}$ |
| 5 | $1.5 \times 10^{-7}$ |
| 6 | $2.7 \times 10^{-8}$ |
| 7 | $2.3 \times 10^{-8}$ |
| 8 | $3.8 \times 10^{-7}$ |
| 9 | $3.6 \times 10^{-8}$ |
| 10 | $2.0 \times 10^{-7}$ |
| 11 | $2.9 \times 10^{-7}$ |
| 12 | $7.0 \times 10^{-7}$ |
| 13 | $2.8 \times 10^{-8}$ |
| 14 | $3.7 \times 10^{-8}$ |

(2) Measuring Method of Interstitial Collagenase Inhibiting Activity

Inhibiting of interstitial collagenase refined from the culture supernatant of human fibroblast cell (Detroit 551 cell) was measured by using fluorescence labeled collagen, according to the method proposed by Nagai et al. [Inflammation, 4 (2), 123 (1984)].

The enzyme was activated by incubating for 3 hours at 37° C. in 1 mM mercury (II) p-aminophenylacetate. The test compound was used by dissolving in dimethyl sulfoxide. The enzyme reaction was started by adding the activated enzyme in 50 mM TRIS-hydrochloric acid (pH 7.5), 0.2M NaCl, 5 mM $CaCl_2$, 0.02% (w/v) $NaN_3$, 2.5 mM acetic acid, and 0.1% (v/v) dimethyl sulfoxide solution containing the test compound and 0.025% (w/v) of fluorescence labeled collagen as substrate. The reaction was conducted for 2 hours at 35° C., and stopped by adding ice-chilled 80 mM O-phenanthroline, 50% (v/v) ethanol solution by 1/20 amount. To this, moreover, an equivalent volume of 50 mM TRIS-hydrochloric acid (pH 7.5), 0.2M NaCl, 5 mM $CaCl_2$, 0.02% (w/v) $NaN_3$ solution was added to incubate further for 1 hour at 35° C. to degenerate specifically only the digestion product, and the digestion product was extracted by adding 0.17M TRIS-hydrochloric acid (pH 9.5), 0.67M NaCl solution including an equivalent amount of 70% (v/v) ethanol, and afterwards, by centrifugal separation for 15 minutes at 3000 rpm, 4° C., the undigested substrate was precipitated. The fluorescence intensity of the obtained supernatant was measured at 520 nm (Em)/495 nm (Ex), and the decomposition volume was quantitatively determined.

The enzyme inhibiting activity was expressed by the concentration ($IC_{50}$) of the test compound wherein the enzyme activity of known amount was inhibited till 50%. The results are shown in Table 2.

TABLE 2

| Test compound | Interstitial collagenase $IC_{50}$ (M) |
| --- | --- |
| 1 | $2.1 \times 10^{-7}$ |
| 2 | $4.5 \times 10^{-7}$ |
| 3 | $6.9 \times 10^{-7}$ |
| 4 | $2.9 \times 10^{-6}$ |
| 5 | $3.6 \times 10^{-7}$ |
| 6 | $2.4 \times 10^{-9}$ |
| 7 | $2.5 \times 10^{-12}$ |
| 8 | $1.6 \times 10^{-7}$ |
| 9 | $2.2 \times 10^{-8}$ |
| 10 | $3.1 \times 10^{-8}$ |
| 11 | $7.5 \times 10^{-7}$ |
| 12 | $2.9 \times 10^{-7}$ |
| 13 | $1.0 \times 10^{-8}$ |
| 14 | $2.2 \times 10^{-8}$ |
| 15 | $2.0 \times 10^{-8}$ |
| 16 | $6.9 \times 10^{-8}$ |
| 17 | $4.1 \times 10^{-8}$ |
| 18 | $8.8 \times 10^{-8}$ |
| 19 | $1.4 \times 10^{-7}$ |
| 20 | $2.2 \times 10^{-7}$ |
| 21 | $1.1 \times 10^{-7}$ |
| 22 | $3.7 \times 10^{-6}$ |
| 23 | $6.4 \times 10^{-11}$ |
| 24 | $7.4 \times 10^{-7}$ |
| 25 | $4.1 \times 10^{-6}$ |
| 26 | $1.0 \times 10^{-6}$ |
| 27 | $1.1 \times 10^{-7}$ |
| 28 | $8.7 \times 10^{-8}$ |
| 29 | $1.4 \times 10^{-8}$ |
| 30 | $1.1 \times 10^{-8}$ |
| 31 | $3.7 \times 10^{-7}$ |

(3) Measuring Method of Type IV Collagenase Inhibiting Activity

Inhibiting of type IV collagenase refined from the culture supernatant of human lung fibroblast cell (HT-1080 cell) was measured by using fluorescence labeled gelatin, according to the method proposed by Haris et al. [Haris, E. D., and Krane, S. M., Biochim. Biophys. Acta., 258, 566–576 (1972)].

The enzyme was activated by incubating for 22 hours at 37° C. in 1 mM mercury (II) p-aminophenylacetate. The test compound was used by dissolving in dimethyl sulfoxide. The enzyme reaction was started by adding the activated enzyme in 50 mM TRIS-hydrochloric acid (pH 7.5), 10 mM CaCl$_2$, 0.01% (w/v) "Bridge 35" (tradename, available from Wako Pure Chemical Industries, Ltd.), 0.1% (v/v) dimethyl sulfoxide solution containing the test compound and 0.1% (w/v) of fluorescence labeled gelatin as substrate. The reaction was conducted for 6 hours at 37° C., and stopped by adding 30% (w/v) trichloroacetic acid solution by ½ amount. After letting stand at 4° C. for 30 minutes, by centrifugal separation for 10 minutes at 10000 rpm, 4° C., the undigested substrate was precipitated. To 1 part by volume of the obtained supernatant, 50 parts by volume of 0.3M phosphate buffer (pH 8.5) was added, and the fluorescence intensity was measured at 520 nm (Em)/495 nm (Ex), and the undigested amount was quantitatively determined.

The enzyme inhibiting activity was expressed by the concentration (IC$_{50}$) of the test compound wherein the enzyme activity of known amount was blocked till 50%. The results are shown in Table 3.

TABLE 3

| Test compound | Type IV collagenase IC$_{50}$ (M) |
|---|---|
| 1 | $1.7 \times 10^{-6}$ |
| 2 | $5.1 \times 10^{-7}$ |
| 3 | $5.3 \times 10^{-7}$ |
| 4 | $1.9 \times 10^{-6}$ |
| 5 | $5.4 \times 10^{-7}$ |
| 6 | $5.8 \times 10^{-8}$ |
| 7 | $1.8 \times 10^{-8}$ |
| 8 | $2.3 \times 10^{-7}$ |
| 9 | $5.6 \times 10^{-9}$ |
| 10 | $8.7 \times 10^{-9}$ |
| 11 | $5.6 \times 10^{-7}$ |
| 12 | $3.4 \times 10^{-7}$ |
| 13 | $4.0 \times 10^{-8}$ |
| 14 | $3.7 \times 10^{-8}$ |
| 15 | $4.6 \times 10^{-8}$ |
| 16 | $1.7 \times 10^{-7}$ |
| 17 | $3.4 \times 10^{-7}$ |
| 18 | $1.9 \times 10^{-6}$ |
| 19 | $9.8 \times 10^{-6}$ |
| 20 | $2.0 \times 10^{-8}$ |
| 21 | $3.4 \times 10^{-7}$ |
| 22 | $>10^{-6}$ |
| 23 | $5.7 \times 10^{-8}$ |
| 27 | $2.2 \times 10^{-6}$ |
| 28 | $3.9 \times 10^{-7}$ |
| 29 | $2.0 \times 10^{-7}$ |
| 30 | $2.4 \times 10^{-7}$ |
| 31 | $1.4 \times 10^{-6}$ |

Pharmacological Test 2

Experiment was carried out according to a method of Motoyama et al. [Gan To Kagaku Ryoho (JAPAN), 21(8): pages 1209–1214, 1994]. That is, Colon 26 PMF15 tumor cells ($5 \times 10^5$/mouse) were inoculated into the left hind footpad of male CDF$_1$ mice (one group comprising 7 mice). After 14 days from inoculation, the left hind-limb was cut from the upper part of the articulatio geniculum under pentobarbital anesthetization using a cautery knife to remove the primary tumor. After 28 days from inoculation, the lung was removed and the number of metastastic nodules on the surface thereof were measured, thereby taking it as an index of the effect. The test compound was orally administered one time a day until 27 days have passed since the day following the day when tumor cells were inoculated, excluding the day when the primary tumor was removed. The results are shown in Table 4 below.

TABLE 4

| Test Compound | Dose (mg/kg/day) | Number of lung metastastic nodules mean ± S.E. | Ratio to control group (%) |
|---|---|---|---|
| Test I | | | |
| Control group | — | 21.1 ± 4.8 | 100 |
| 3 | 25 | 19.0 ± 3.7 | 90 |
| 3 | 50 | 18.7 ± 6.0 | 88 |
| 3 | 100 | 13.0 ± 5.2 | 61 |
| 3 | 200 | 9.2 ± 2.8 | 43 |
| Test II | | | |
| Control group | — | 39.4 ± 9.1 | 100 |
| 28 | 1 | 37.1 ± 5.8 | 94 |
| 28 | 2 | 36.7 ± 8.2 | 93 |
| 28 | 5 | 34.0 ± 5.8 | 86 |
| 28 | 10 | 25.4 ± 4.3 | 64 |
| 28 | 20 | 21.4 ± 4.8 | 54 |

PHARMACEUTICAL EXAMPLE 1

The following ingredients were blended by ordinary method, and tableted, and 100 tablets containing 50 mg of active ingredient per tablet were obtained.

| | |
|---|---|
| 3S-[4-(N-hydroxyamino)-2R-isobutyl-3S-acetyl-thiomethylsuccinyl]amino-3,4-dihydrocarbostyril | 5 g |
| Sodium lauryl sulfate | 0.2 g |
| Magnesium stearate | 0.2 g |
| Crystalline cellulose | 4.6 g |

PHARMACEUTICAL EXAMPLE 2

| | |
|---|---|
| 3S-[4-(N-hydroxyamino)-2R-isobutylsuccinyl]amino-1-carboxymethyl-3,4-dihydrocarbostyril | 1 g |
| Polyethylene glycol (molecular weight: 4000) | 0.3 g |
| Sodium chloride | 0.9 g |
| Polyoxy ethylene sorbitan mono oleate | 0.4 g |
| Sodium metabisulfite | 0.1 g |
| Methyl parabane | 0.18 g |
| Propyl parabane | 0.02 g |
| Distilled water for injection | 10.0 ml |

While stirring parabanes, sodium metabisulfite and sodium chloride, they are dissolved in distilled water in about half volume of the specified amount at 80° C. The obtained solution was cooled to 40° C., and active ingredient compounds of the invention, and polyethylene glycol and polyoxy ethylene sorbitan mono oleate were dissolved in the solution. Distilled water for injection was added to the solution to adjust to a final volume, and the solution was sterilized and filtered through a proper filter paper to sterilize, thereby preparing an injection.

What is claimed is:

1. A carbostyril derivative or a salt thereof of formula (1):

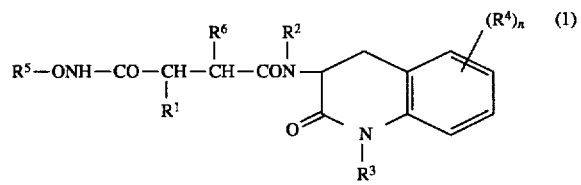

wherein R$^1$ is a hydrogen atom or a group —A—R$^{1a}$, wherein A is a lower alkylene group, and R$^{1a}$ is selected from the group consisting of a hydrogen atom, an amino group, a phthalimido group, a thienylthio group, a lower alkanoylthio group, a mercapto group, a phenyl group which may possess one to three groups selected from the group consisting of a halogen atom, a hydroxy group, a lower alkyl group, a lower alkoxy group, a carboxy group, a lower alkoxycarbonyl group and a lower alkylenedioxy group as a substituent, a carboxy group, a lower alkoxycarbonyl group, a phenylthio group, and a lower alkylthio group;

$R^2$ is a hydrogen atom or a lower alkyl group;

$R^3$ is selected from the group consisting of a hydrogen atom, a hydroxy group, a lower alkoxy group, a lower alkoxy-lower alkoxy group, a lower alkoxy-lower alkoxy-lower alkoxy group, a lower alkoxy-lower alkoxy-lower alkoxy-lower alkoxy group, and a group —B—$R^{3a}$ wherein B is a lower alkylene group, a lower alkenylene group or a lower alkynylene group, and $R^{3a}$ is selected from the group consisting of a hydrogen atom, a hydroxy group, a lower alkoxy group, a lower alkyoxy-lower alkoxy group, a phenyl group which may possess one to three groups selected from the group consisting of a halogen atom, a cyano group, a hydroxy group, a lower alkyl group, a lower alkoxy group, a carboxy group and a lower alkoxycarbonyl group as a substituent, a thienyl group which may possess a halogen atom as substituent, a phthalimido group, a carboxy group, a lower alkoxycarbonyl group, a group —CO—N($R^{3b}$)—$R^{3c}$ wherein $R^{3b}$ is a hydrogen atom or a lower alkyl group, and $R^{3c}$ is a hydrogen atom, a lower alkyl group or a lower alkoxy group, and a group —N($R^{3b}$)—$R^{3c}$ wherein $R^{3b}$ and $R^{3c}$ are as defined above and may form a saturated heterocyclic ring with five or six members which may further possess one hetero atom selected from the group consisting of a nitrogen atom, an oxygen atom and a sulfur atom;

$R^4$ is selected from the group consisting of a hydrogen atom, a halogen atom, a hydroxy group, a lower alkyl group, a lower alkoxy group, and a lower alkylenedioxy group;

$R^5$ is selected from the group consisting of a hydrogen atom, a benzoyl group, a lower alkanoyl group, and a phenyl-lower alkyl group;

$R^6$ is an alkyl group with 1 to 12 carbon atoms, a lower alkoxy-lower alkyl group, or a phenyl-lower alkyl group which may possess a lower alkylenedioxy group as a substituent on the phenyl ring; and n is 1 or 2, or its salt.

2. A carbostyril derivative or its salt as claimed in claim 1, wherein $R^2$ is a hydrogen atom and $R^5$ is a hydrogen atom.

3. A carbostyril derivative or its salt as claimed in claim 1, wherein $R^5$ is a benzoyl group, a lower alkanoyl group, or a phenyl-lower alkyl group.

4. A carbostyril derivative or its salt as claimed in claim 2, wherein $R^4$ is selected from the group consisting of a hydrogen atom, a halogen atom, a lower alkoxy group, and a lower alkylenedioxy group; and $R^6$ is an alkyl group with 1 to 12 carbon atoms.

5. A carbostyril derivative or its salt as claimed in claim 2, wherein $R^6$ is a lower alkoxy-lower alkyl group, or a phenyl-lower alkyl group which may possess a lower alkylenedioxy group as a substituent on the phenyl ring.

6. A carbostyril derivative or its salt as claimed in claim 4, wherein $R^1$ is a hydrogen atom or a group —A—$R^{1a}$ wherein A is a lower alkylene group; and $R^{1a}$ is selected from the group consisting of a hydrogen atom, a phthalimido group, a thienylthio group, a lower alkanoylthio group, and a phenyl group which may possess one to three groups selected from the group consisting of a halogen atom, a hydroxy group, a lower alkyl group, a lower alkoxy group, a carboxy group, a lower alkoxycarbonyl group and a lower alkylenedioxy group as a substituent.

7. A carbostyril derivative or its salt as claimed in claim 4, wherein $R^1$ is a group —A—$R^{1a}$ wherein A is a lower alkylene group, and $R^{1a}$ is selected from the group consisting of an amino group, a mercapto group, a carboxy group, a lower alkoxycarbonyl group, a phenylthio group, and a lower alkylthio group.

8. A carbostyril derivative or its salt as claimed in claim 4, wherein $R^3$ is a hydrogen atom, or a group —B—$R^{3a}$ wherein B is a lower alkylene group, a lower alkenylene group or a lower alkynylene group, and $R^{3a}$ is selected from the group consisting of a hydrogen atom, a lower alkoxy group, a lower alkoxy-lower alkoxy group, a carboxy group, and a group —CO—N($R^{3b}$)—$R^{3c}$ wherein $R^{3b}$ is a hydrogen atom or a lower alkyl group, and $R^{3c}$ is a hydrogen atom, a lower alkyl group or a lower alkoxy group.

9. A carbostyril derivative or its salt as claimed in claim 8, wherein $R^1$ is a hydrogen atom or a group —A—$R^{1a}$ wherein A is a lower alkylene group, and $R^{1a}$ is selected from the group consisting of a hydrogen atom, a phthalimido group, a thienylthio group, a lower alkanoylthio group, and a phenyl group which may possess one to three groups selected from the group consisting of a halogen atom, a hydroxy group, a lower alkyl group, a lower alkoxy group, a carboxy group, a lower alkoxycarbonyl group and a lower alkylenedioxy group as a substituent.

10. A carbostyril derivative or its salt as claimed in claim 9, wherein $R^3$ is a group —B—$R^{3a}$ wherein B is a lower alkylene group, and $R^{3a}$ is a lower alkoxy group or a lower alkoxy-lower alkoxy group.

11. A carbostyril derivative or its salt as claimed in claim 10, wherein $R^1$ is a hydrogen atom or a group —A—$R^{1a}$ wherein A is a lower alkylene group, and $R^{1a}$ is a hydrogen atom.

12. A carbostyril derivative or its salt as claimed in claim 9, wherein $R^3$ is a hydrogen atom, or a group —B—$R^{3a}$ wherein B is a lower alkylene group, and $R^{3a}$ is a hydrogen atom, a carboxy group, or a group —CO—N($R^{3b}$)—$R^{3c}$ wherein $R^{3b}$ is a hydrogen atom or a lower alkyl group, and $R^{3c}$ is a hydrogen atom, a lower alkyl group or a lower alkoxy group.

13. A carbostyril derivative or its salt as claimed in claim 12, wherein $R^1$ is a hydrogen atom or a group —A—$R^{1a}$ wherein A is a lower alkylene group, and $R^{1a}$ is a hydrogen atom.

14. A carbostyril derivative or its salt as claimed in claim 9, wherein $R^3$ is a group —B—$R^{3a}$ wherein B is a lower alkenylene group or a lower alkynylene group, and $R^{3a}$ is selected from the group consisting of a hydrogen atom, a lower alkoxy group, a lower alkoxy-lower alkoxy group, a carboxy group, and a group —CO—N($R^{3b}$)—$R^{3c}$ wherein $R^{3b}$ is a hydrogen atom or a lower alkyl group, and $R^{3c}$ is a hydrogen atom, a lower alkyl group or a lower alkoxy group.

15. A carbostyril derivative or its salt as claimed in claim 4, wherein $R^3$ is selected from the group consisting of a hydroxy group, a lower alkoxy group, a lower alkoxy-lower alkoxy group, a lower alkoxy-lower alkoxy-lower alkoxy group, and a lower alkoxy-lower alkoxy-lower alkoxy-lower alkoxy group.

16. A carbostyril derivative or its salt as claimed in claim 15, wherein $R^1$ is a hydrogen atom or a group —A—$R^{1a}$ wherein A is a lower alkylene group, and $R^{1a}$ is selected from the group consisting of a hydrogen atom, a phthalimido group, a thienylthio group, a lower alkanoylthio group, and a phenyl group which may possess one to three groups selected from the group consisting of a halogen atom, a hydroxy group, a lower alkyl group, a lower alkoxy group, a carboxy group, a lower alkoxycarbonyl group and a lower alkylenedioxy group as a substituent.

17. A carbostyril derivative or its salt as claimed in claim 16, wherein $R^1$ is a hydrogen atom or a group —A—$R^{1a}$ wherein A is a lower alkylene group, and $R^{1a}$ is a hydrogen atom.

18. A carbostyril derivative or its salt as claimed in claim 17, wherein $R^3$ is a lower alkoxy group.

19. A carbostyril derivative or its salt as claimed in claim 4, wherein $R^3$ is a group —B—$R^{3a}$ wherein B is selected from the group consisting of a lower alkylene group, a lower alkenylene group and a lower alkynylene group, and $R^{3a}$ is selected from the group consisting of a hydroxy group, a phenyl group which may possess one to three groups selected from the group consisting of a halogen atom, a cyano group, a hydroxy group, a lower alkyl group, a lower alkoxy group, a carboxy group and a lower alkoxycarbonyl group as a substituent, a thienyl group which may possess a halogen atom as a substituent, a phthalimido group, a lower alkoxycarbonyl group and a group —CO—N($R^{3b}$)—$R^{3c}$ wherein a group —N($R^{3b}$)—$R^{3c}$ forms a saturated heterocyclic ring with five or six members which may further possess one hetero atom selected from the group consisting of a nitrogen atom, a oxygen atom and a sulfur atom.

20. A method of preparing a carbostyril derivative of formula (1):

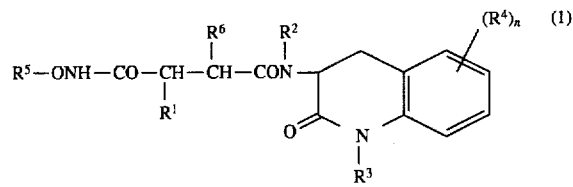

wherein $R^1$ is a hydrogen atom or a group —A—$R^{1a}$ wherein A is a lower alkylene group, and $R^{1a}$ is selected from the group consisting of a hydrogen atom, an amino group, a phthalimido group, a thienylthio group, a lower alkanoylthio group, a mercapto group, a phenyl group which may possess one to three groups selected from the group consisting of a halogen atom, a hydroxy group, a lower alkyl group, a lower alkoxy group, a carboxy group, a lower alkoxycarbonyl group and a lower alkylenedioxy group as a substituent, a carboxy group, a lower alkoxycarbonyl group, a phenylthio group, and a lower alkylthio group;

$R^2$ is a hydrogen atom or a lower alkyl group;

$R^3$ is selected from the group consisting of a hydrogen atom, a hydroxy group., a lower alkoxy group, a lower alkoxy-lower alkoxy group, a lower alkoxy-lower alkoxy-lower alkoxy group, a lower alkoxy-lower alkoxy-lower alkoxy-lower alkoxy group, and a group —B—$R^{3a}$ wherein B is a lower alkylene group, a lower alkenylene group or a lower alkynylene group, and $R^{3a}$ is selected from the group consisting of a hydrogen atom, a hydroxy group, a lower alkoxy group, a lower alkyoxy-lower alkoxy group, a phenyl group which may possess one to three groups selected from the group consisting of a halogen atom, a cyano group, a hydroxy group, a lower alkyl group, a lower alkoxy group, a carboxy group and a lower alkoxycarbonyl group as a substituent, a thienyl group which may possess a halogen atom as substituent, a phthalimido group, a carboxy group, a lower alkoxycarbonyl group, a group —CO—N($R^{3b}$)—$R^{3c}$ wherein $R^{3b}$ is a hydrogen atom or a lower alkyl group, and $R^{3c}$ is a hydrogen atom, a lower alkyl group or a lower alkoxy group, and a group —N($R^{3b}$)—$R^{3c}$ wherein $R^{3b}$ and $R^{3c}$ are as defined above and may form a saturated heterocyclic ring with five or six members which may further possess one hetero atom selected from the group consisting of a nitrogen atom, an oxygen atom and a sulfur atom;

$R^4$ is selected from the group consisting of a hydrogen atom, a halogen atom, a hydroxy group, a lower alkyl group, a lower alkoxy group, and a lower alkylenedioxy group;

$R^5$ is selected from the group consisting of a hydrogen atom, a benzoyl group, a lower alkanoyl group, and a phenyl-lower alkyl group;

$R^6$ is an alkyl group with 1 to 12 carbon atoms, a lower alkoxy-lower alkyl group, or a phenyl-lower alkyl group which may possess a lower alkylenedioxy group as a substituent on the phenyl ring; and n is 1 or 2, which comprises the step of reducing or saponifying a compound of the formula (1-A):

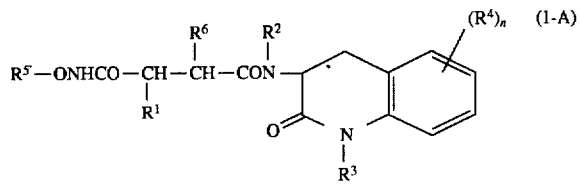

to provide a compound of the formula (1-B):

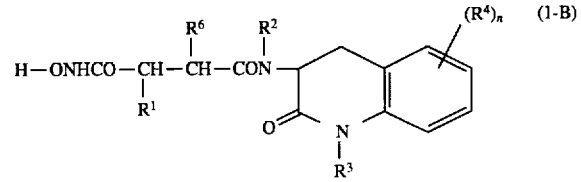

wherein in the above formulas, $R^1$, $R^2$, $R^3$, $R^4$, $R^6$ and n are the same meanings as defined above in formula (1), and $R^{5'}$ is a benzoyl group, a lower alkanoyl group or a phenyl-lower alkyl group.

21. An extracellular matrix metalloproteinases inhibitor composition comprising a pharmacologically effective amount of a carbostyril derivative defined in claim 1 or its salt and a pharmacologically-acceptable carrier.

22. A carbostyril derivative or its salt as claimed in claim 2, wherein $R^4$ is a lower alkylenedioxy group and n is 1.

23. A carbostyril derivative or its salt as claimed in claim 22, wherein $R^1$ is a hydrogen atom, $R^3$ is a lower alkyl group and $R^6$ is an alkyl group with 1 to 12 carbon atoms.

24. A carbostyril derivative or its salt as claimed in claim 23, wherein $R^3$ is a methyl group or an ethyl group, and $R^6$ is a lower alkyl group.

25. A carbostyril derivative or its salt which is selected from the group consisting of:

3S-[4-(N-hydroxyamino)-2R-isobutylsuccinyl]amino-1-methyl-6,7-methylenedioxy-3,4-dihydrocarbostyril;

1-ethyl-3S-[4-(N-hydroxyamino)-2R-isobutylsuccinyl] amino-6,7-methylenedioxy-3,4-dihydrocarbostyril;

1-ethyl-3S-[4-(N-hydroxyamino)-2R-pentylsuccinyl] amino-6,7-methylenedioxy-3,4-dihydrocarbostyril;

3S-[4-(N-hydroxyamino)-2R-pentylsuccinyl]amino-1-methoxy-3,4-dihydrocarbostyril; and 3S-[4-(N-hydroxyamino)-2R-isobutylsuccinyl]amino-1-methoxymethoxy-3,4-dihydrocarbostyril.

26. A carbostyril derivative that is 1-ethyl-3S-[4-(N-hydroxyamino)-2R-isobutylsuccinyl]amino-6,7-methylenedioxy-3,4-dihydrocarbostyril or its salt.

27. A carbostyril derivative or a salt thereof selected from the group consisting of 3S-[4-(N-hydroxyamino)-2R-isobutylsuccinyl]amino-1-methoxy-3,4-dihydrocarbostyril, 3S-[4-(N-hydroxyamino)-2R-isobutyl-3S-acetylthiomethylsuccinyl]amino-3,4-dihydrocarbostyril, 3S-[4-(N-hydroxyamino)-2R-isobutyl-3S-methylsuccinyl]amino-1-methoxy-3,4-dihydrocarbostyril, 3S-[4-(N-hydroxyamino)-2R-isobutylsuccinyl]amino-1-methoxymethyl-3,4-dihydrocarbostyril, 1-carboxymethyl-3S-[4-(N-hydroxyamino)-2R-isobutyl-3S-methylsuccinyl]amino-3,4-dihydrocarbostyril, 3S-[4-(N-hydroxyamino)-2R-isobutylsuccinyl]amino-1-methoxyethoxymethyl-3,4-dihydrocarbostyril, 3S-[4-(N-hydroxyamino)-2R-heptylsuccinyl]amino-1-methoxy-3,4-dihydrocarbostyril, 7-chloro-3S-[4-(N-hydroxyamino)-2R-isobutylsuccinyl]amino-1-methoxymethyl-3,4-dihydrocarbostyril, 3S-[4-(N-hydroxyamino-2R-isobutylsuccinyl]amino-1-methoxyethyl-3,4-dihydrocarbostyril, 3S-[4-(N-hydroxyamino)-2R-isobutylsuccinyl]amino-1-methoxyethyl-6,7-methylenedioxy-3,4-dihydrocarbostyril, and 3R-[4-(N-hydroxyamino)-2R-isobutylsuccinyl]amino-1-methoxyethyl-6,7-methylenedioxy-3,4-dihydrocarbostyril.

* * * * *